(12) United States Patent
Gleich et al.

(10) Patent No.: US 11,883,248 B2
(45) Date of Patent: Jan. 30, 2024

(54) IDENTIFYING SYSTEM FOR IDENTIFYING A MEDICAL TOOL LIKE A SURGICAL INSTRUMENT

(71) Applicant: KONINKLIJKE PHILIPS N.V., Eindhoven (NL)

(72) Inventors: Bernhard Gleich, Hamburg (DE); Jürgen Erwin Rahmer, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 32 days.

(21) Appl. No.: 17/541,669

(22) Filed: Dec. 3, 2021

(65) Prior Publication Data
US 2022/0175487 A1    Jun. 9, 2022

(30) Foreign Application Priority Data

Dec. 3, 2020 (EP) .................................... 20211539

(51) Int. Cl.
*A61B 90/90* (2016.01)
*G16H 40/40* (2018.01)
*G06K 7/04* (2006.01)

(52) U.S. Cl.
CPC ................ *A61B 90/90* (2016.02); *G06K 7/04* (2013.01); *G16H 40/40* (2018.01)

(58) Field of Classification Search
CPC .......... A61B 90/90; A61B 2017/00477; A61B 2017/00725; A61B 2090/376;
(Continued)

(56) References Cited

U.S. PATENT DOCUMENTS 5,565,847 A    10/1996 Gambino
6,144,300 A    11/2000 Dames
(Continued)

FOREIGN PATENT DOCUMENTS

EP    2349047 A    10/2000
EP    3583896 A1   12/2019
(Continued)

OTHER PUBLICATIONS

Schrott A.G. et al., "Magnetic Arrays and Their Resonant Frequencies for the Production of Binary Codes", IEEE Transactions on Magnetics, vol. 34, No. 5, pp. 3765-3771, Sep. 1998.
(Continued)

*Primary Examiner* — Seung H Lee
(74) *Attorney, Agent, or Firm* — Sherry Austin

(57) ABSTRACT

The invention relates to a passive medical identification device 1 to be used for identifying a medical tool such as, for example, a surgical instrument, if the medical tool is equipped with the identification device. The identification device comprises a casing 2, a magnetic object 3 arranged within the casing such that it is rotatable out of an equilibrium orientation by an external magnetic torque, and a restoring torque provider 4 such as, for example, a further magnetic object providing a restoring torque forcing the magnetic object back into the equilibrium orientation. The magnetic object 3 rotationally oscillates upon excitation by an external magnetic torque, thereby generating a response magnetic signal which is transduced into an induction signal that can provide a fingerprint specific for the respective identification device. Accordingly, the identity of the identification device and hence of the medical tool equipped with the identification device can be determined based on the induction signal.

21 Claims, 19 Drawing Sheets

(58) Field of Classification Search
CPC .... A61B 2090/3954; A61B 2090/3966; A61B 90/39; G06K 7/04; G16H 40/40
See application file for complete search history.

(56) References Cited

U.S. PATENT DOCUMENTS

2009/0212768 A1    8/2009  Llandro
2020/0360106 A1   11/2020  Ghanam
2020/0397530 A1*  12/2020  Gleich ..................... G01K 7/36

FOREIGN PATENT DOCUMENTS

WO    WO2018051129 A1    3/2018
WO    WO2019243098 A1   12/2019

OTHER PUBLICATIONS

Hayward T.J. et al., "Towards Magnetic Suspension Assay Technology", AIP Conference Proceedings 1025, 111, Jun. 2008.
Baszynski et al., "Electromagnetic Navigation in Medicine—Basic Issues, Advantages and Shortcomings, Prospects of Improvement", Journal of Physics: Conference Series, vol. 238 (2010) 012056.
Xiang, Q. et al., "Fast Numerical Algorithm for a High-Precision 6D Electromagnetic Positioning Navigation System", Turkish Journal of Physics, vol. 38, pp. 165-173, 2014.

* cited by examiner

IDENTIFYING SYSTEM FOR IDENTIFYING A MEDICAL TOOL LIKE A SURGICAL INSTRUMENT

FIELD OF THE INVENTION

The invention relates to an identifying system for identifying a medical tool equipped with a passive medical identification device, i.e. for instance, a surgical instrument equipped with a passive medical identification device. The invention relates also to the passive medical identification device, a holding device for holding at least two of the passive medical identification devices in a passive medical combination identification device, and the passive medical combination identification device comprising the holding device and at least two of the passive medical identification devices. Moreover, the invention relates to a medical tool equipped with the passive medical identification device and/or the passive medical combination identification device, a set of different passive medical identification devices for equipping different medical tools with different passive medical identification devices, a use of the passive medical identification device and/or the passive medical combination identification device for providing the medical tool with an identity, an identifying method and a computer program for identifying a medical tool equipped with the passive medical identification device and/or the passive medical combination identification device. The invention relates also to a manufacturing method for manufacturing the passive medical combination identification device.

BACKGROUND OF THE INVENTION

It is known to equip medical tools such as, for example, surgical instruments with radio-frequency identification (RFID) elements, in order to allow to identify these objects. However, the RFID elements need relatively large antennas and hence are relatively large, which make them unsuitable for identifying relatively small objects.

SUMMARY OF THE INVENTION

It is an object of the present invention to provide an identifying system for identifying a medical tool equipped with a passive medical identification device and to provide the passive medical identification device such that it can be relatively small. Moreover, it is an object of the present invention to provide a holding device for holding at least two of the passive medical identification devices in a passive medical combination identification device and to provide the passive medical combination identification device comprising the holding device and at least two of the passive medical identification devices. Furthermore, it is an object of the present invention to provide a medical tool such as, for example, a surgical instrument equipped with the passive medical identification device and/or the passive medical combination identification device, a set of different passive medical identification devices for equipping different medical tools with different passive medical identification devices, a use of the passive medical identification device and/or the passive medical combination identification device for providing the medical tool with an identity, an identifying method and a computer program for identifying a medical tool equipped with the passive medical identification device and/or the passive medical combination identification device. It is a further object of the present invention to provide a manufacturing method for manufacturing the passive medical combination identification device.

In a first aspect of the present invention a passive medical identification device to be used for identifying a medical tool, if the medical tool is equipped with the identification device, is presented, wherein the identification device comprises:
  a casing,
  a magnetic object being arranged within the casing such that it is rotatable out of an equilibrium orientation if an external magnetic torque is acting on the magnetic object,
  a restoring torque provider being configured to provide a restoring torque to force the magnetic object back into the equilibrium orientation if an external magnetic torque has rotated the magnetic object out of the equilibrium orientation, in order to allow for a rotational oscillation of the magnetic object excited by the external magnetic torque, the rotational oscillation generating a response magnetic signal,
  the casing, magnetic object and the restoring torque provider being arranged such that at least one property of the response magnetic signal is suitable to be used by an identification system to extract identification data from an induction signal.

Since the magnetic object is arranged within the casing such that it is rotatable out of an equilibrium orientation by an external magnetic torque acting on the magnetic object and since the restoring torque provider is configured to provide a restoring torque to force the magnetic object back to the equilibrium orientation if the external magnetic torque has rotated the magnetic object out of the equilibrium orientation, in order to allow for a rotational oscillation of the magnetic object excited by the external magnetic torque, a response magnetic field is generated by the rotational oscillation and the response magnetic field can be transduced into an induction signal by an excitation and induction signal coil system of an identifying system. In particular, the excitation and induction signal coil system can comprise i) first coils configured to generate the magnetic field providing the magnetic torque for rotating the magnetic object of the identification device out of its equilibrium orientation and to thereby excite the rotational oscillation of the magnetic object, the rotational oscillation inducing the response magnetic field, and ii) second coils configured to transduce the response magnetic field into the induction signal. The induction signal can provide a fingerprint which is specific for the respective identification device such that the identity of the identification device and hence of the medical tool, which is equipped with the identification device, can be determined based on the induction signal. The restoring torque provider could also be regarded as being a restoring torque providing unit that is configured to provide the restoring torque.

Generally, a passive identification device is basically a device which is able to store in some form of identification data and which has output unit for generating a response signal to an excitation electromagnetic signal. A reading device sends the excitation electromagnetic field which powers the identification device leading to the response signal, wherein the reading device transduces the response signal into identification data. It should be noted that storage and the response signal could be either analog or digital. An example of an analog signal is when the signal could vary between a minimum and maximum value and the range is divided into a predetermined number of intervals, each interval being associated with a digital value. Identification data should be construed broadly as covering both data suitable for unique identification, for example a predetermined value or a random value, or data describing the properties of the tool being identified. Thus, the identification data could refer to, for example, a property of the tool, a manufacturer of the tool, a name of the tool, et cetera.

It is noted that WO 2019/243098 A1 and EP 3 583 896 A1 refer to devices in a completely different field, i.e. both documents disclose a micromechanical oscillator for sensing purposes, i.e. the output of the device is correlated to a parameter of the environment of the device or to the location and orientation of the device. These documents do not suggest any other use of such an oscillator beyond or how it could be adapted beyond such use. In particular, these documents do not propose how the disclosed devices could be adapted for being used for identification purposes, i.e. how identification data could be stored in the device and how the identification data could be extracted from the device.

The identification device can be relatively small, for instance, smaller than 1 mm. In particular, in at least one spatial direction the identification device is smaller than 1 mm. In an example embodiment the identification device is smaller than 1 mm in at least two orthogonal spatial directions. Moreover, in an embodiment in each spatial direction the identification device is smaller than 1 mm, i.e. it can be placed completely within an imaginary sphere having a diameter of 1 mm. In a preferred embodiment, the casing of the identification device is cylindrical and the outer diameter of the cylinder is smaller than 1 mm, further preferred smaller than 0.5 mm and even further preferred smaller than 0.3 mm. Moreover, the identifying system can read out the identification device from a relatively large distance which is, for instance, larger than 30 cm.

It is noted that the term "external magnetic torque" refers to a magnetic torque caused by an external magnetic field generator being outside of the identification device. In some embodiments, the external magnetic field generator is also outside of a subject, if the identification device is arranged within the subject. The excitation and induction signal coil system might generate the external magnetic field and hence also be regarded as including the external magnetic field generator.

In some embodiments, the magnetic object is rotatable around a virtual rotational axis centrally traversing the magnetic object, wherein the magnetic object is rotationally symmetric with respect to the virtual rotational axis. In particular, the magnetic object is a magnetic sphere or a magnetic cylinder.

The restoring torque provider can be arranged within the casing together with the magnetic object. In an example embodiment the restoring torque provider comprises a torsional spring mechanism and/or a further magnetic object for providing the restoring torque. Thus, in an example embodiment the restoring torque provider might comprise a further magnetic object for providing the restoring torque. In an example embodiment the magnetic object is attached to one end of a filament, wherein another end of the filament is attached to the casing, wherein the filament is configured to prevent that the magnetic object touches the further magnetic object due to their magnetic attraction and to allow the magnetic object to rotationally oscillate. In some embodiments, the further magnetic object is stationarily attached to the casing. However, the further magnetic object can also be arranged within the casing such that it is rotationally oscillatable relative to the casing. In particular, the further magnetic object can be attached to one end of a filament, wherein another end of the filament can be attached to the casing. In a preferred embodiment the further magnetic object is rotatable around a virtual rotational axis centrally traversing the further magnetic object, wherein the further magnetic object is rotationally symmetric with respect to the virtual rotational axis. Also the further magnetic object might be a magnetic sphere or a magnetic cylinder. Moreover, the virtual axes of the magnetic object and the further magnetic object are aligned with each other in some embodiments.

These techniques allow to provide a restoring torque and hence a rotational oscillation of the magnetic object such that the overall identification device can be relatively small, the induction signal comprising the fingerprint can be provided as desired and the construction of the identification device can still be relatively simple.

In an example embodiment in which the further magnetic object is present, the casing and/or the filament is elastic such that the distance between the magnetic object and the further magnetic object is changeable depending on the magnetic attraction between the magnetic object and the further magnetic object. The change of the distance between the magnetic object and the further magnetic object depends on the degree of elasticity or softness of the casing and/or the filament, wherein this change of distance also leads to a change of the resonant frequency which can be determined based on the induction signal. This change of the resonant frequency can hence be measured and used for identifying the respective identification device. Also how fast this distance and hence the resonant frequency changes, i.e. the time constant, can be used for identifying the respective identification device.

For instance, the casing and/or the filament might comprise rubber, particularly silicone rubber, a polymer and/or a metal. In an example embodiment the casing comprises a rubber hose which might be a silicone rubber hose. The casing and/or filament might also be structured such as, for example, a bellow for providing the elasticity or softness. For ease of manufacturing the casing might also comprise a polymer coating such as, for example, a parylene coating and/or a metal coating for providing the elasticity or softness. These materials can be extremely thin and therefore provide the necessary elasticity or softness especially if the material is structured such as, for example, a bellow. Metal coatings are especially preferred for long term stability of the identification device. The polymer or metal coatings might be provided as coatings on a rubber part, wherein the rubber part might be, for instance, the rubber hose. However, the filament might also comprise rubber as a coating on a polymer or metal part. For instance, the rubber hose might form a coating of a polymer or metal base.

In an example embodiment the casing is filled with a fluid. If the casing is filled with fluid, the viscosity of the fluid can have a damping effect for the rotational oscillation of the magnetic object, which can be used for encoding and therefore allows for a further improved identification of the respective identification device. In some embodiments, the viscosity of the fluid with which the casing is filled is relatively low, for instance, below the 1 mPas of water. If the fluid is a liquid, it may be based on a light hydrocarbon as pentane with mixtures of other hydrocarbons such as, for example, decane to generate several viscosities down to the approximately 230 µPas of pure pentane. If the fluid is a gas, it might be hydrogen offering a viscosity of 8 µPas at atmospheric pressure and/or neon offering a viscosity of 30 µPa at atmospheric pressure. Again mixtures, i.e. in this case gas mixtures, can be used for providing a range of different viscosities. For instance, hydrogen and/or neon can be mixed with gases having intermediate viscosity values such as, for example, nitrogen. It is also possible to have different identification devices with different internal pressures within the respective casing. These different internal pressures can be used, for instance, in order to have identification devices spanning from having liquid pentane inside the casing to having no or almost no viscosity inside the casing. The different viscosities can lead to different dampings of the rotational oscillation of the magnetic object and hence to different changes of the resonant frequency which can be determined based on the induction signal.

In an example embodiment the casing comprises an inner casing wall and an outer casing wall, wherein a space between the inner casing wall and the outer casing wall is filled with a fluid. In this case, the viscosity of the fluid can have an effect on the time constant associated with a change in length of the casing, and therefore also a change in a distance between the magnetic object and the further magnetic object. Preferably, the inner casing wall is softer or more elastic than the outer casing wall. In particular, the casing might be structured such as, for example, a bellow within a housing, wherein the housing is filled with a fluid not entering the bellow, in which case the bellow might be viewed as the inner casing wall and the housing might be viewed as the outer casing wall. The fluid present between the inner casing wall and the outer casing wall preferably has a higher viscosity than the fluid which might be present in the casing. Choosing fluids with different viscosities can lead to different time constants associated with the change in distance between the magnetic object and the further magnetic object, which can allow for a further improved identification of the respective identification device.

In an example embodiment the magnetic object is attached to each of respective one ends of at least two filaments, wherein respective other ends of the at least two filaments are attached to the casing, wherein the filaments are configured to prevent that the magnetic object touches the further magnetic object due to their magnetic attraction and to allow the magnetic object to rotationally oscillate. Thus, an identification device might be distinguished from another identification device with respect to the number of filaments. For instance, the identification devices might comprise either one or two filaments. Whether a respective identification device has one or two filaments can be determined, for example, by measuring the sensitivity of the resonant frequency of the respective identification device to an external magnetic field, particularly to an external temporally constant magnetic field, i.e. a DC magnetic field. In particular, if only a single filament is used, the sensitivity of the resonant frequency to the external magnetic field is relatively high, whereas this sensitivity is relatively low for an identification device having two filaments attaching the rotating magnetic object to the casing. Thus, also this sensitivity can be used for identifying the respective identification device.

The at least two filaments can be made of different materials and/or have different thicknesses. By using different materials and/or different thicknesses the sensitivity of the resonant frequency to the external magnetic field can be further varied. This allows to distinguish between more identification devices and hence leads to a further improved identification of identification devices based on the sensitivity of the resonant frequency to the external magnetic field.

In an example embodiment the identification device is configured such that the further magnetic object is rotatable out of an equilibrium orientation if an external magnetic torque is acting on the further magnetic object, wherein the restoring torque provider is configured to also provide a restoring torque to force the further magnetic object back into the equilibrium orientation if an external magnetic torque has rotated the further magnetic object out of the equilibrium orientation, in order to allow for a rotational oscillation of the further magnetic object excited by the external magnetic torque, wherein the rotational oscillations of the magnetic object and the further magnetic object have the same resonant frequency and a phase difference of 180 degrees. This reduces, optimally even cancels, the torque on the casing. The restoring torque provider can use the magnetic object for providing the restoring force for the further magnetic object. In particular, in an example embodiment the magnetic object forms a first magnetic dipole, the further magnetic object forms a second magnetic dipole, and the magnetic object and the further magnetic object are arranged such that in the equilibrium orientation the first and second magnetic dipoles point in opposite directions. In an example embodiment the magnetic object and the further magnetic object are directly connected to each other via a torsion spring such that in this case the restoring torque provider comprises the torsion spring.

In some embodiments the magnetic object and/or the further magnetic object is a permanent magnet.

In some embodiments, the casing is cylindrical. If the casing is cylindrical, it can be relatively easily introduced into a tubular medical device such as, for example, a guidewire.

In some embodiments the identification device is configured to fulfill at least one condition of i) a Q factor of at least 100, ii) a dynamic dipole moment of at least 0.5 $\mu Am^2$, and/or iii) a resonant frequency of at least 100 Hz. It has been found that, if at least one of these conditions is fulfilled, the accuracy of determining the identity of the identification device can be further increased.

In some embodiments the identification device is radiopaque. This allows to visualize the identification device also by using an x-ray imaging system such as, for example, a computed tomography system, an x-ray fluoroscopy system, an x-ray C-arm system, et cetera.

In some embodiments the casing and the magnetic object comprise a restriction element for restricting the maximally possible rotation of the magnetic object out of the equilibrium orientation. Both, the casing and the magnetic object, or only one of the casing and the magnetic object, can comprise such a restriction element. The maximally possible rotation, which could also be regarded as being a maximum angle of oscillation, can differ between different identification devices and therefore also be used to identify the respective identification device. In an example embodiment the casing and the magnetic object each comprise a protrusion which get in touch and prevent a further rotation of the magnetic object out of the equilibrium orientation, if the maximally possible rotation of the magnetic object out of the equilibrium orientation has been reached. For instance, the casing can comprise an inner stopper and the oscillating magnetic object can comprise a nose, which get in touch and prevent a further rotation of the magnetic object out of the equilibrium orientation, if the maximally possible rotation of the magnetic object out of the equilibrium orientation has been reached.

The stopper can absorb the energy or act as a reflector, maintaining at least a portion of the energy, which could also be used for distinguishing the identification devices from each other. In other words, it can be distinguished between an absorbing stopper type and a reflecting stopper type, wherein this binary distinguishing can be regarding as providing a bit for identifying the respective identification device. The reflecting stopper type retains the energy such that a further resonant excitation leads to a frequency increase that can be detected based on the induction signal, whereas a further resonant excitation in the energy absorption case, i.e. if the absorbing stopper type is used, does not lead to a frequency change of the induction signal. This different behavior can be used for the encoding. It is also possible that different identification devices have stoppers with more degrees of absorption, i.e. not only binary—absorption or no absorption. If different identification devices have different stoppers absorbing different portions of the energy, the frequency of the induction signal changes differently, which can be used for further distinguishing different identification devices and hence for identifying them.

In an example embodiment the identification device comprises a magnetically soft material which could also be named soft magnetic material. The oscillating magnetic object can produce a quite strong varying magnetic field in the vicinity, which can magnetize the magnetically soft material such that it can reach saturation and therefore produce additional harmonics in the induction signal. The type, size, shape, location and orientation of the magnetically soft material relative to the oscillating magnetic object can modify the additional harmonics of the induction signal such that the additional harmonics can be used for identifying the respective identification device. In particular, the magnetic object comprises a magnetically soft material. For instance, the magnetic object can be made of magnetically soft material. In an example embodiment it can be a soft magnetic sphere or cylinder. The soft magnetic object can also be used in addition to, for example, on top, of a hard magnetic object. By using the soft magnetic material, the maximally possible rotation of the magnetic object out of the equilibrium orientation can be increased. Also soft magnetic material can therefore be used, in order to provide different identification devices with different maximally possible rotations, in order to identify the respective identification device. The use of the soft magnetic material can also have the additional benefit of an increased strength of the induction signal. In an example embodiment the casing of the identification device comprises a magnetically soft material. The soft magnetic material can focus the external magnetic field and thereby further increase the sensitivity of the resonant frequency to the external magnetic field. Thus, different identification devices can have different amounts of soft magnetic material and/or can have the soft magnetic material at different positions within the identification device, in order to provide different sensitivities to the external magnetic field. It is of course also possible that at least one of the identification devices does not comprises any soft magnetic material. The kind of soft magnetic material may be chosen from one of the very soft magnetic materials such as, for example, the "Permalloy" type nickel iron alloys or the more modern but harder to process nano-magnetic materials. Particularly if the magnetic material had a small hysteresis such as, for example, for instance, pure nickel or common carbon steels, the resulting frequency hysteresis when applying a DC magnetic field could be used for bit encoding, i.e. for distinguishing between different identification devices. Almost any position of the soft magnetic material at or within the identification device will have an effect on the induction signal.

In some embodiments the soft magnetic material is elongated, wherein the long axis is along the magnetization direction of the soft magnetic material. This can be beneficial in reducing demagnetization.

In an example embodiment the soft magnetic material can be provided as symmetric wires on both sides of the oscillator, i.e. on both sides of the oscillating magnetic object and the restoring torque provider. The symmetric design has the advantage that forces due to the soft magnetic material on the rotating magnetic object are relatively low. This means that the accuracy of determining the identity is not or only little perturbed by the soft magnetic material. If, for instance, the soft magnetic material were located only on one side of the oscillator, the magnetic object may become stuck to the casing. However, in a further embodiment the soft material can also be provided as asymmetric wires on both sides of the oscillator. This can lead to a reduced amount of space required for the wires made of the soft magnetic material. In some embodiments the asymmetric wires have different dimensions that are selected such that forces on the magnetic object caused by the asymmetric wires are cancelled out.

The identification device can comprise a further oscillating element which is mechanically coupled to the magnetic object. The further oscillating element can be indirectly or directly coupled to the magnetic object. For instance, if the magnetic object is attached to one end of a filament and another end of the filament is attached to the casing, the casing can be a springy casing, wherein the further oscillating element such as, for example, an oscillating ring is integrated in a springy part of the casing, thereby providing a restoring force for the oscillation of the further oscillating element. In this case the further oscillating element may be indirectly mechanically and/or magnetically coupled to the magnetic object, such as via the filament and the casing and/or, respectively, via the casing and the restoring torque provider, which might be fixed to the casing. The resonant frequency of the further oscillating element can be used for determining the identity, i.e. the identification data, of the identification device, wherein the resonant frequency of the further oscillating element can be probed by using the initial oscillator formed by the magnetic object and the restoring torque provider.

In a further embodiment the magnetic object and the restoring torque provider form a first oscillator, wherein the identification device comprises a second oscillator formed by a) a further magnetic object being arranged within the casing such that it is rotatable out of an equilibrium orientation if an external magnetic torque is acting on the further magnetic object and b) a further restoring torque provider being configured to provide a restoring torque to force the further magnetic object back into the equilibrium orientation if an external magnetic torque has rotated the further magnetic object out of the equilibrium orientation, in order to allow for a rotational oscillation of the further magnetic object excited by the external magnetic torque. Different identification devices can have the first and second oscillators in different spatial relations relative to each other, in order to generate different induction signals for the different identification devices.

In a further aspect of the present invention a holding device for holding at least two passive medical identification devices, in order to form a passive medical combination identification device comprising the at least two identification devices, is presented. The holding device comprises at least a first holder configured to hold a first identification device, a second holder for holding a second identification device and a positioner configured to position the first holder and the second holder in one of a plurality of positions relative to each other. By using the holding device, several combination identification devices, which cause different induction signals due to the different relative positions of the different single identification devices relative to each other and which hence have different identities, can be manufactured in a relatively simple way, wherein the single identification devices can even be identical. However, the single identification devices used for manufacturing the combination identification device can also be different. The different relative positions refer to different relative orientations and/or relative locations.

Moreover, in an aspect of the present invention a passive medical combination identification device comprising at least two passive medical identification devices and the holding device is presented, wherein the first holder holds a first identification device, the second holder holds a second identification device and the positioner positions the first holder and the second holder in one of a plurality of positions relative to each other. In an example embodiment the combination identification device further comprises a casing, wherein the holding device and the identification devices are positioned within the casing.

In particular, the combination identification device can be regarded as being an N-tuplet identification device that comprises N identification devices according to any of the previously described embodiments and the holding device, which could also be named positioning unit, for holding each of the N identification devices relative to each of the other N−1 identification devices. N is herein understood to be an integer number. In the context of this aspect, the identification devices according to the previously described embodiments could be regarded as singlet identification devices. Instead of comprising N singlet identification devices, an N-tuplet identification device might also comprise N M-tuplet identification devices. Also M is understood to be an integer number, wherein preferably M<N. N-tuplet identification devices have the advantage that they allow to encode a relatively large amount of identification information using well-known basic building blocks.

In an example embodiment the N-tuplet identification is a doublet identification device comprising two identification devices as defined in any of the previously described embodiments, i.e. singlet identification devices, and the holding device, which could also be regarded as being a positioning unit, for positioning a first of the two singlet identification devices relative to the second of the two singlet identification devices. The positioning unit comprise a) the first holder that is adapted to hold the first singlet identification device in a first position, b) a third holder as the positioner, wherein the first holder and the third holder are adapted to be fixed to each other in a second position, and c) the second holder, wherein the second holder and the third holder are adapted such that the third holder can hold the second holder in a third position, and wherein the second holder is adapted to hold the second singlet identification device in a fourth position. The first singlet identification device and the second singlet identification device are preferably held fixed by the first holder and the second holder, respectively. Also the second holder is preferably held fixed by the third holder. The positioning unit is preferably adapted to allow for a relative positioning of the second singlet identification device with respect to the first singlet identification by allowing for different fourth positions for a given first position. For instance, the first position might be regarded as a reference position of the first singlet identification device, such as relative to the first holder, for instance, and the fourth position might be regarded as a position of the second singlet identification device relative to the reference position. In an example embodiment the first holder and the third holder are adapted to be fixed in a configurable relative orientation to each other, the third holder is adapted to hold the second holder at a configurable one of several relative distances to the first holder and the second holder is adapted to hold the second singlet identification device in a configurable orientation relative to the third holder. In this case, the position of the second singlet identification device relative to the first singlet identification device can be determined based on the relative orientation between the first holder and the third holder, the relative distance between the first holder and the second holder and the relative orientation between the third holder and the second holder.

In a further aspect of the present invention a set of several passive medical identification devices is presented, wherein at least two of the identification devices differ from each other with respect to at least one property selected from a list comprising: resonant frequency, magnetic dipole moment, maximum oscillation angle, zero excitation amplitude frequency, oscillation damping, resonant frequency of a further oscillating element of the identification device, amount of change of the resonant frequency depending on an excitation amplitude of an exciting magnetic field, velocity of change of the resonant frequency depending on the excitation amplitude of the exciting magnetic field, sensitivity of the respective resonant frequency to an external magnetic field, generation of harmonics of the induction signal due to soft magnetic material, and/or number of magnetic oscillators.

In some embodiments, the magnetic dipole moment, which might be different from identification device to identification device, is the effective magnetic dipole moment of the oscillating magnetic object.

In some embodiments, the zero excitation amplitude frequency is the frequency of the induction signal at which the excitation amplitude has been extrapolated to a zero excitation amplitude. In an example embodiment the induction signal and hence the frequency of the induction signal is measured for different non-zero excitation amplitudes applied by the excitation and induction signal coil system, in order to measure this frequency depending on the excitation amplitude. This measurement leads to a decaying waveform which can be continued by, for instance, extrapolation or fitting, in order to determine the zero excitation amplitude frequency. In particular, a fit function, which describes the measured dependency, can be fitted to the measured waveform, in order to continue the measured waveform. Also a model can be used for this fitting procedure. This model describes the oscillation of the magnetic object and hence the generation of the induction signal depending on the excitation amplitude.

The velocity of change of the resonant frequency depending on an excitation amplitude of an exciting magnetic field is determined as a time constant in some embodiments.

The external magnetic field used for determining the sensitivity of the resonant frequency to this field is a temporally constant magnetic field, i.e. a DC magnetic field, in some embodiments.

In an example embodiment in at least two of the identification devices the casing and the magnetic object comprise a restriction element for restricting the maximally possible rotation of the magnetic object out of the equilibrium orientation, wherein the restriction elements of at least two of the at least two of the identification devices have different mechanical impact absorption properties. Moreover, in an example embodiment at least two of the identification devices differ from each other with respect to a shape of the magnetic object. By providing different shapes, different identification devices having different effective magnetic dipoles can be provided in a technically relatively simple way. The different shapes could be, for instance, cylindrical or spherical.

In an example embodiment in at least two identification devices of the set of identification devices the magnetic object is attached to one end of a filament at an attachment location on the magnetic object, wherein another end of the filament is attached to the casing, wherein the attachment locations of the at least two identification devices are different. Also this allows to provide different effective magnetic dipole moments in a technically relatively simple way. For instance, for at least some identification devices the attachment location might not be at the equator of the magnetic object, if the magnetic object is a sphere, in order to provide a reduced effective magnetic dipole moment, whereas for other identification devices the attachment location might be at the equator.

In an example embodiment at least two of the identification devices differ from each other with respect to a type, an amount, a size, a shape, an orientation and/or a location of magnetically soft material. For instance, different identification devices can have different amounts of soft magnetic material and/or can have the soft magnetic material at different locations within the identification device and/or with different shapes, in order to provide different sensitivities to the external magnetic field. It is of course also possible that at least one of the identification devices does not comprise any soft magnetic material.

The orientation and/or location of the soft magnetic material can refer to an orientation and/or a location relative to the oscillating magnetic object. For instance, a varying location and/or orientation of the magnetically soft material relative to the oscillating magnetic object can lead to a varying generation of harmonics of the induction signal due to soft magnetic material and can hence be used to identify the respective identification device based on the harmonics of the induction signal.

Moreover, in an example embodiment at least two of the identification devices differ from each other with respect to an amount of soft material of the magnetic object. For instance, one of the identification devices might have a magnetic object made of hard magnetic material, i.e. it might be a permanent magnet, whereas another one of the identification devices might have a magnetic object made of soft magnetic material or a magnetic object comprising a combination of soft and hard magnetic materials, wherein a ratio of soft to hard magnetic material might change from identification device to identification device. In addition or alternatively, a position of the soft magnetic material relative to the hard magnetic material of a magnetic object might be different from identification device to identification device.

In an example embodiment at least two of the identification devices differ from each other with respect to a filling of the casing with a fluid and/or, if the magnetic object is attached to the casing via a filament, a stiffness and/or thickness of the filament. For instance, the casings can be filled with different gases having different viscosities and/or the filaments can be made of different materials, which can lead to different damping properties, particularly to different linear damping constants. Identification devices can therefore be provided such that they have different damping properties.

In an example embodiment the respective restoring torque provider of the respective identification device comprises a further magnetic object for providing the restoring torque, wherein the respective magnetic object is attached to the respective casing by using one or several filaments, wherein the one or several filaments are adapted to prevent that the respective magnetic object touches the respective further magnetic object due to their magnetic attraction and to allow the respective magnetic object to rotationally oscillate, wherein at least two of the identification devices differ from each other with respect to the number of filaments and/or the material of the one or more filaments and/or the thickness of the one or more filaments. The use of the different numbers of filaments, of filaments having different thicknesses and/or of filaments comprising different materials allows to vary the sensitivity of the resonant frequency to the external magnetic field in a technically relatively simple way.

In an example embodiment at least two of the identification devices comprise, besides a first oscillator formed by the respective magnetic object and the respective restoring torque provider, a second oscillator formed by a) a further magnetic object being arranged within the casing such that it is rotatable out of an equilibrium orientation if an external magnetic torque is acting on the further magnetic object and b) a further restoring torque provider being configured to provide a restoring torque to force the further magnetic object back into the equilibrium orientation if an external magnetic torque has rotated the further magnetic object out of the equilibrium orientation, in order to allow for a rotational oscillation of the further magnetic object excited by the external magnetic torque, wherein the at least two identification devices differ from each other with respect to at least one property such as, for example, a distance between the first and second oscillators, an orientation of one of the first and second oscillators relative to the other of the first and second oscillators, and/or a coupling strength between the first and second oscillators. Different distances and different orientations can lead to different induction signals and can hence be used to identify the respective identification device. In particular, the angles, i.e. the relative orientations, and distances can be used in the same way as all measured unique quantities can be used for encoding, wherein the different inductions signals can be directly used, or the orientations and/or distances can be determined based on the generated induction signals and the determined orientations and/or distances can be used, for identifying the respective identification device. For example, if there is a set of identification devices, wherein the identification devices differ from each other with respect to 103 relative orientations and 5 relative distances of the respective oscillators, there are 515 additional possibilities which translates to about 9 bits which can be used for encoding the identification devices.

A relative orientation and/or a relative distance could be determined, for instance, based on known relations between a) induction signal parameters and b) relative orientations and/or relative distances. These relations can be predetermined by calibrating the system, wherein the induction signal can be measured, while a known relative orientation and/or a known relative distance is present. The coupling strength between the first and second oscillators can be binary, i.e. either there is any coupling or no coupling, or different identification devices can have more than two different coupling strengths. The oscillators can couple by way of mechanical coupling and/or by magnetic interactions. In both cases, the strength of the coupling can be modulated, i.e. varied from identification device to identification device, by the mechanical set-up and/or by the addition of soft magnetic material.

As mentioned above, it is possible to distinguish between resonators that couple and that do not. For instance, firstly, both oscillators can be excited, which results in two peaks at two frequencies in the induction signal. Then, an excitation pulse, i.e. an excitation magnetic field, can be used at one of these two frequencies, with relative high magnetic excitation amplitudes where non-linear effects are already expected. In some embodiments, an excitation pulse can be used at one of these two frequencies only. If the resulting induction signal shows a signal pattern of a single oscillator only, i.e., for instance, has a peak only at the one frequency, the two oscillators are not coupled and the coupling strength is zero. However, if the resulting induction signal shows a signal pattern of two resonators, i.e., for instance, two peaks at two frequencies, particularly a beat frequency, the oscillators are coupled and the coupling strength is non-zero. The consideration of the coupling strength can hence provide at least one additional bit which can be used for encoding the identification devices.

In an example embodiment at least two of the identification devices comprise, besides a first oscillator formed by the respective magnetic object and the respective restoring torque provider, a second oscillator formed by a) a further magnetic object being arranged within the casing such that it is rotatable out of an equilibrium orientation if an external magnetic torque is acting on the further magnetic object and b) a further restoring torque provider being configured to provide a restoring torque to force the further magnetic object back into the equilibrium orientation if an external magnetic torque has rotated the further magnetic object out of the equilibrium orientation, in order to allow for a rotational oscillation of the further magnetic object excited by the external magnetic torque, wherein the at least two identification devices have a same respective one of the first and second oscillators and wherein the respective other one of the first and second oscillators differs from identification device to identification device with respect to its spatial relation to the respective one of the first and second oscillators and/or with respect to its construction. The construction of an oscillator refers to, for instance, the number and kind of components, the used materials, the relative positions of the different components, et cetera. Since a respective one of the first and second oscillators is the same for different identification devices, in this embodiment this respective one of the first and second oscillators cannot be used for distinguishing the different identification devices and hence for identifying the different identification devices, but it can be used for measuring a property such as, for example, a temperature, a pressure, et cetera. The cluster of properties measured could be quite broad and could include pH values, ionizing radiation, light radiation, magnetic field, magnetic field strength, chemical concentration such as, for example, moisture and others. It could therefore be regarded as being a measuring oscillator or measurement type oscillator. The respective other one of the first and second oscillators is different or has a different spatial relation to the measuring oscillator for different identification devices and can therefore be used for distinguishing the different identification devices and hence for identifying the different identification devices. This other one could be regarded as being an identifying oscillator or identification type oscillator. Thus, in an example embodiment an identification device comprises a measurement type oscillator that does not provide any additional encoding as it is, for instance, mass produced and always the same. It may, for example, measure the temperature by a temperature dependent frequency shift. In some embodiments, the frequency ranges of both oscillators do not overlap such that it is known which frequency range of the induction signal is for identification and which frequency range of the induction signal is for measurement. A processor that might be used for identifying identification devices might then also be used for temperature measurements. For instance, the processor can be configured to, if the induction signal shows two peaks, determine the locations of the sources of the two peaks and the distance between these two locations, wherein, if this distance is smaller than a predefined threshold, it concludes that the two frequencies belong to a same identification device, wherein one frequency is used for determining the identity of the identification device and the other frequency is used for determining the temperature of the identification device. If there are more than two peaks, corresponding locations can be determined and the locations can be clustered such that peaks caused by nearby locations are assigned to each other, wherein the frequency at one of the peaks of a cluster is used for determining the respective identity and the frequency at another one of the peaks of a same cluster is used for determining the respective temperature. Instead of or in addition to the temperature, a measuring oscillator can also be used for measuring another property such as, for example, pressure.

A set of same, i.e. identical, oscillators can be used for generating different identification devices, which can be distinguished from each other, by arranging them in a respective same identification device in different relative orientation and/or distances with respect to each other. For instance, for each identification device a mold can be provided, in which two oscillators can be placed, wherein the mold can be configured such that it can be chosen between 128 different relative angles between a respective pair of oscillators. This can provide seven bits for encoding the identification devices, without needing to manufacture different oscillators. Each oscillator comprises a magnetic object being arranged within a casing such that it is rotatable out of an equilibrium orientation if an external magnetic torque is acting on the magnetic object and a restoring torque provider being configured to provide a restoring torque to force the magnetic object back into the equilibrium orientation if an external magnetic torque has rotated the magnetic object out of the equilibrium orientation, in order to allow for a rotational oscillation of the magnetic object excited by the external magnetic torque. The respective oscillator might also comprise a respective casing. In some embodiments, the operation of this embodiment can be described as follows: measure position and angles of all identification devices. After measuring the system may select the identification device as a reference identification device based on e.g. the lowest frequency measured. The relative angles and distances of all markers with respect to the reference marker can encode information as described.

In a further aspect of the present invention a use of a passive medical identification device as defined by any of claims 1 to 6 and 8 for providing a medical tool with an identity is presented. Thus, the identification device and/or the combination identification device can be attached to the medical tool such as, for example, a surgical instrument, in order to provide the medical tool with an identity as defined by the identification device.

In another aspect of the present invention an identifying system, which could also be regarded as being a reading system, for identifying a medical tool equipped with a passive medical identification device as defined by any of claims 1 to 6 and 8 is presented. Thus, the identification system is configured to identify a medical tool equipped with an identification device which might be an identification device in accordance with any of claims 1 to 6 or an identification device in accordance with claim 8, i.e. the above mentioned combination identification device, wherein the identifying system comprises:

an excitation and induction signal coil system configured to a) generate a magnetic field providing a magnetic torque for rotating the magnetic object of the identification device out of its equilibrium orientation and for thereby exciting a rotational oscillation of the magnetic object, the rotational oscillation inducing a response magnetic field, and b) transduce the response magnetic field into an induction signal, a processor configured to receive the induction signal and to extract identification data.

The identifying system may also comprise further hardware elements interacting with the excitation and induction signal coil system and/or the processor during operation. For instance, the identifying system might further comprise a memory for storing and providing data, such as calibration data, wherein the processor might be adapted to retrieve the data from the memory. Also, the identifying system, particularly the excitation and induction signal coil system, might comprise a controller, wherein the controller might be adapted to control coils of the excitation and induction signal coil system, particularly the magnetic field generated by the coils.

In an example embodiment the excitation and induction signal coil system comprises a) first coils configured to generate the magnetic field providing the magnetic torque for rotating the magnetic object of the identification device out of its equilibrium orientation and to thereby excite the rotational oscillation of the magnetic object, the rotational oscillation inducing a response magnetic field, and b) second coils configured to transduce the response magnetic field into the induction signal that depends on the identity of the identification device, wherein the first and second coils are separated. The first coils and/or the second coils can be arranged, for instance, in a mat or in a handheld device. The coils can also be arranged in another element such as, for example, a box.

In a further embodiment the excitation and induction signal coil system comprises coils configured to a) generate the magnetic field providing the magnetic torque for rotating the magnetic object of the identification device out of its equilibrium orientation and to thereby excite the rotational oscillation of the magnetic object, the rotational oscillation inducing a response magnetic field, and b) transduce the response magnetic field into an induction signal. Thus, the same coils can be used for generating the magnetic field and for generating the induction signal. Also in this embodiment the coils may be arranged in a mat or in a handheld device. The coils can also be arranged in another element such as, for example, a box.

In an example embodiment the processor is configured to i) determine, based on the induction signal, at least one property of the identification device selected from a list consisting of resonant frequency, effective magnetic dipole moment, maximum oscillation angle, zero excitation amplitude frequency, oscillation damping, resonant frequency of a further oscillating element of the identification device, amount of change of the resonant frequency depending on an excitation amplitude of an exciting magnetic field, velocity of change of the resonant frequency depending on the excitation amplitude of the exciting magnetic field, sensitivity of the respective resonant frequency to an external magnetic field, generation of harmonics of the induction signals, and ii) extract the identification data of the identification device based on the determined at least one property of the identification device.

The processor can comprise assignments between a) the properties and/or characteristics of the induction signal and b) identifiers of medical tools equipped with the identification devices and these assignments can be used together with a respective determined at least one property and/or current characteristics of the induction signal for determining an identifier of a medical tool. The identifier might be, for instance, an alpha-numerical sign.

In another embodiment the processor is configured to determine the resonant frequency of the identification device based on the frequency of the induction signal and to extract the identification data based on the determined resonant frequency. For instance, the processor can comprise or retrieve assignments between a) resonant frequencies and b) identities and be configured to extract the identification data of the identification device depending on the assignments and the determined resonant frequency. In an example embodiment a set of identification devices is provided, of which the resonant frequencies cover a range of about 2 kHz, wherein the identifying system is configured to determine the frequency of the induction signal and hence the resonant frequency with an accuracy of 1 Hz. In this embodiment it is possible to distinguish between about 2000 identification devices, which corresponds to about eleven bits which could be used for the encoding.

In an example embodiment the processor is configured to determine the resonant frequency of the identification device based on a combination of the induction signals generated in different coils of the excitation and induction signal coil system. For instance, the combination might involve a weighted average over the different induction signals More preferably, a model as described below is used to describe the identification device as a resonator by, for instance, a set of differential equations. For specified initial conditions and parameters of the identification device, the model gives the magnetic dipole strength of the identification device over time. Specifying further a location of the identification device in space allows for a determination of expected induction signals generated in the different coils over time based on the evolution of the magnetic dipole strength given by the model. Parameters of the coils, such as their sensitivities, might be known from simulation or calibration, for instance. Comparing the expected induction signals with the induction signals actually measured in the different coils allows for an optimization of the initial conditions and the parameters of the model as well as the position of the identification device, i.e. its location and the orientation of its magnetic dipole strength. The optimization may refer to an optimization with respect to a difference, or weighted difference, between the expected induction signals and the induction signals actually measured in the different coils, i.e. to a process of matching the model output to the voltages measured in the different coils as optimally as possible. In order to reduce the time needed for optimization, it is preferred to estimate, for instance, parameters such as, for example, the resonant frequency and/or the location of the identification device, and to initiate the optimization based on these estimates. The estimates may be obtained, using standard electromagnetic positioning techniques, for instance, based on correlations that can be determined between the induction signals generated in the different coils.

In an example embodiment the processor is configured to determine an effective magnetic dipole moment of the magnetic object of the identification device based on the induction signal and to extract the identification data based on the determined effective magnetic dipole moment. This effective magnetic dipole moment can be used as an independent parameter for identifying the identification device, i.e. it can be used, for instance, independently of the resonant frequency. It has been found that in an example embodiment it can be distinguished between at least 32 different effective magnetic dipole moments, thereby providing at least five bits for encoding the identity of the respective identification device.

The term "effective magnetic dipole moment" refers to the component of the magnetic dipole moment, which really changes during the rotational oscillation of the magnetic object. In particular, the magnetic dipole moment can be decomposed in a component along the rotational axis of the magnetic object, i.e., for instance, along a filament, if the magnetic object is attached to a filament, and in a component being perpendicular to the rotational axis. The component along the rotational axis does not change when the magnetic object rotates and hence does not contribute to the induction signals. The effective magnetic dipole moment could therefore also be described as being the component which is perpendicular to the rotational axis.

In an example embodiment the processor is configured to determine a maximum oscillation angle of the identification device, i.e. of the rotationally oscillating magnetic object, based on the induction signal and to extract the identification data based on the determined maximum oscillation angle. In particular, the processor can be configured to determine a second harmonic of the induction signal and to determine the maximum oscillation angle based on the determined second harmonic. In an example embodiment the identifying system and the identification device are configured such it can be distinguished between at least 32 different maximum oscillation angles, thereby providing five bits for encoding the identity of the respective identification device.

In order to determine the maximum oscillation angle, which may be defined as the maximum angle of the rotating magnetic object relative to its equilibrium position in the casing, a model might be used, which describes the induction signal depending on, inter alia, the maximum oscillation angle, wherein this model might be the well-known differential equation of a dampened pendulum, wherein the gravitational force is replaced by magnetic force, as described below. However, as mentioned above, it is also possible that the processor is configured to determine the maximum oscillation by observing the second harmonic of the oscillation frequency. In particular, the processor can be configured to determine a ratio between a second harmonic and a first harmonic of the induction signal and to determine the maximum oscillation angle based on this ratio. The processor can use known assignments such as, for example, a table between these ratios and maximum oscillation angles, wherein these assignments can be determined by calibration. The calibration can include measuring this ratio for different known maximum oscillation amplitudes. The first and second harmonics can be determined by Fourier transforming the induction signal. Exemplary, the Fourier transform of the time signal of the first harmonic (e.g. base frequency) and the second harmonic (e.g. double frequency) are separated in certain spectrum. Respective contributions from the peak amplitudes are determined.

In an example embodiment the excitation and induction signal coil system is configured to a) generate the magnetic field providing the magnetic torque for rotating the magnetic object of the identification device out of its equilibrium orientation with different amplitudes and for thereby exciting a rotational oscillation of the magnetic object with different excitation amplitudes, the rotational oscillation inducing a response magnetic field, and b) transduce the response magnetic field into the induction signal that depends on the different excitation amplitudes, wherein the processor is configured to determine a dependency of a frequency of the induction signal on the excitation amplitude based on the induction signal, to adapt a dependency model, which is configured to model a dependency of the frequency of the induction signal on the excitation amplitude, to the determined dependency and to determine, as the zero excitation amplitude frequency, the frequency at which the adapted dependency model indicates a zero excitation amplitude. This allows to reliably determine the zero excitation amplitude frequency. In an example embodiment the identifying system and the identification device are configured such the zero excitation amplitude can be determined with an accuracy of 1 Hz over a bandwidth of about 2 kHz. This roughly corresponds to about 2 to the power of 11 such that in this way about 11 bits can be used for encoding the identity of the respective identification device.

In an example embodiment the processor is adapted to determine an oscillation damping property based on the induction signal and to extract the identification data based on the determined oscillation damping property. In particular, the processor is configured to determine a linear oscillation damping property and/or a higher-order oscillation damping property as the oscillation damping property. The linear oscillation damping property refers to the dissipative force such as, for example, a friction force being linear in the velocity of the movement of the magnetic object. The linear oscillation damping property can be defined by, for instance, a corresponding linear damping constant. In some embodiments, the processor is configured to determine the oscillating damping property based on a decay of the amplitude of the induction signal over time.

In order to determine the linear oscillation damping property only, i.e. not also a higher order oscillating damping property, a decay of the amplitude of the induction signals over time can be considered, after an excitation of the rotational oscillation of the magnetic object with a relatively low amplitude of the generated magnetic field has been stopped, which does not generate higher harmonics. In order to determine the higher-order oscillating damping property and optionally also the linear oscillating damping property based on a decay of the amplitude of the induction signals over time, a decay of the amplitude of the induction signals over time can be considered, after an excitation with a relative large amplitude of the generated magnetic field has been stopped, which also generated higher harmonics. The linear and higher order oscillating damping properties can be determined by fitting a given model to the decaying amplitude of the induction signal. In an example embodiment the model is given by the well-known mentioned differential equation of a dampened pendulum, wherein the gravitational force is replaced by magnetic force, for instance as described below. The processor can also be configured to fit an exponential model to the decay of the amplitude of the induction signal over time, in order to determine the linear damping property.

For instance, in an example embodiment the oscillator of the identification device is excited with an amplitude of the generating exciting magnetic field, which is so low that the oscillation can be described by a dampened harmonic oscillator. The rotational oscillation can in this case be described by the following differential equation:

$$\ddot{x}+\gamma\dot{x}+\omega_0^2 x=0 \quad (1),$$

wherein x indicates the angle of the magnetic object relative to its equilibrium angular orientation, γ indicates the linear damping constant and $\omega_0$ the natural frequency, i.e. the resonant frequency, of the identification device without damping. The dots indicate temporal derivative operators. The amplitude of the induction signal is matched with the temporal derivate of x scaled with a scaling factor, wherein the scaling factor, $\omega_0$ and γ are varied until the best possible match is reached. This allows to determine the linear damping constant γ. It is noted that equation (1) applies to the time following excitation, wherein a magnetic force or torque term from the exciting magnetic field would appear on the right hand side of equation (1) during excitation.

In an example embodiment the identifying system and the identification device are configured such it can be distinguished between at least 32 different linear damping constants such that in this way at least about five bits can be used for encoding the identity of the respective identification device.

In an example embodiment the oscillator of the identification device is excited with an amplitude of the generating exciting magnetic field, which is so large that also a higher order, i.e. a non-linear damping, constant is present. This higher order damping constant might be caused by, for instance, a periodic elongation of the filament used for attaching the rotating magnetic object to the casing. In such an example embodiment the rotational oscillation might be described by the following differential equation:

$$\ddot{x}+(\gamma+f(x^2))\dot{x}+\omega_0^2 x=0 \quad (2)$$

In this equation the function $f(\ )$ describes the higher-order damping, wherein the function $f(\ )$ depends on the respective oscillator and can be determined by calibration and/or based on well-known mathematics regarding damped oscillators. In an example embodiment, particularly if the magnetic object is a magnetic sphere attached to the casing via a filament and if a further magnetic sphere is stationarily fixed to the casing as described above, following function can be used $$f(y)=\delta y^2 \quad (3),$$

wherein δ indicates a higher order damping constant. Also in this case the amplitude of the generated inducting signal is matched with the temporal derivate of x scaled with a scaling factor, wherein the scaling factor, $\omega_0$, γ and δ are varied until the best possible match is reached. This allows to determine the linear damping constant γ and also the higher-order damping constant δ. In an example embodiment the identifying system and the identification device are configured such it can be distinguished between at least eight different higher-order damping constants such that in this way at least three further bits can be used for encoding the identity of the respective identification device.

In an example embodiment the identification device comprises a further oscillating element which is mechanically coupled to the magnetic object of the identification device, wherein the processor is configured to determine a resonant frequency of the further oscillating element based on the induction signal and to extract the identification data based on the determined resonant frequency of the further oscillating element. For this determination, in an example embodiment, the excitation and induction signal coil system is configured to a) generate the magnetic field providing the magnetic torque for rotating the magnetic object of the identification device out of its equilibrium orientation with different amplitudes and for thereby exciting a rotational oscillation of the magnetic object with different excitation amplitudes such that it oscillates with different resonant frequencies, wherein the rotational oscillation induces the response magnetic field, and b) transduce the response magnetic field into the induction signal that depends on the different excitation amplitudes, wherein the processor is configured to determine the excitation amplitude, at which the further oscillating element oscillates with its resonant frequency, based on the induction signal and to extract the identification data of the identification device based on the determined excitation amplitude. In some embodiments, the resonant frequency of the identification device without the further oscillating element, i.e. the resonant frequency of the magnetic object and the restoring torque provider, depends on the excitation amplitude. Thus, by modifying the excitation amplitude, the frequency, with which this initial oscillator oscillates, can be modified. For instance, the frequency of the initial oscillator might be shiftable by about 100 Hz by varying the excitation amplitude. Since the initial oscillator is mechanically coupled to the further oscillating element which might be, for instance, a ring integrated in a springy part of the casing, the oscillation of the initial oscillator can excite an oscillation of the further oscillating element, if the initial oscillator oscillates with the resonant frequency of the further oscillating element, wherein this oscillation of the further oscillating element can be detected in the induction signal. Thus, the resonant frequency of the further oscillating element can be determined by measuring the induction signal for different excitation amplitudes. The determined resonant frequency of the further oscillating element can then be used for identifying the respective marker element. In an example embodiment the identifying system and the identification device are configured such it can be distinguished between at least eight different resonant frequencies of the further oscillating element such that in this way at least three bits can be used for encoding the identity of the respective identification device.

In an example embodiment the resonant frequency of the further oscillating element, which might be provided by a springy casing, is detected by modelling the two oscillators and their coupling by using well known oscillation differential equations of the pendulum, wherein the induction signal is proportional to the temporal derivative of the angle of the magnetic object relative to this equilibrium orientation. It is also possible to determine assignments between a) characteristics of induction signals and b) the resonant frequency of the further oscillating element and/or the identity of the respective identification device by calibration and to use these assignments directly for determining the respective resonant frequency and/or identity or for training an artificial intelligence.

In a further embodiment the identification device comprises, besides a first oscillator formed by the respective magnetic object and the respective restoring torque provider, a second oscillator formed by a) a further magnetic object being arranged within the casing such that it is rotatable out of an equilibrium orientation if an external magnetic torque is acting on the further magnetic object and b) a further restoring torque provider being configured to provide a restoring torque to force the further magnetic object back into the equilibrium orientation if an external magnetic torque has rotated the further magnetic object out of the equilibrium orientation, in order to allow for a rotational oscillation of the further magnetic object excited by the external magnetic torque, wherein the processor is configured to determine at least one property of a group consisting of a distance between the first and second oscillators, an orientation of one of the first and second oscillators relative to the other of the first and second oscillators and a coupling strength between the first and second oscillators and to extract the identification data based on the determined property. The coupling of the two oscillators, i.e. of the two oscillating magnetic objects, can be described by a coupling constant, i.e. a corresponding force term. In an example embodiment, this can be described as follows.

The movement of the first oscillator can be described by following differential equation of a dampened pendulum:

$$\ddot{x} + \gamma \dot{x} + \sin(x) = 0 \quad (4).$$

The movement of the second oscillator, before considering the coupling, might be described by following differential equation:

$$\ddot{z} + \eta \dot{z} + w_z^2 z = 0 \quad (5),$$

with $\eta$ indicating a damping constant of the further, second oscillator, $\omega_z$ indicating its natural frequency, i.e. resonant frequency without damping, and z indicating the relative angle of the further magnetic object relative to its equilibrium angular orientation. The coupling strength F, which could also be named coupling force, can be described by following equation:

$$F = k(x + pz) \quad (6),$$

wherein this coupling strength can be added to the differential equations as follows:

$$\ddot{x} + \gamma \dot{x} + \omega_0^2 \sin(x) = F \quad (7) \text{ and}$$

$$\ddot{z} + \eta \dot{z} + w_z^2 z = -F \quad (8)$$

This can be numerically solved and matched to the induction signal, of which the amplitude is proportional to temporal first derivatives of x and z, respectively, which results in the coupling constant k, while p and amplitudes in z are optimized in tandem.

In an example embodiment the processor is configured to determine a) an amount of change of the resonant frequency depending on an excitation amplitude of an exciting magnetic field and/or b) a velocity of change of the resonant frequency depending on an excitation amplitude of an exciting magnetic field, based on the induction signal and to extract the identification data based on the determined a) amount of change of the resonant frequency depending on the excitation amplitude of the exciting magnetic field and/or b) the velocity of change of the resonant frequency depending on the excitation amplitude of the exciting magnetic field. In particular, the excitation and induction signal coil system is configured to a) generate the magnetic field providing the magnetic torque for rotating the magnetic object of the identification device out of its equilibrium orientation with different amplitudes and for thereby exciting a rotational oscillation of the magnetic object with different excitation amplitudes, the rotational oscillation inducing a response magnetic field, and b) transduce the response magnetic field into an induction signal that depends on the different excitation amplitudes, wherein the processor is configured to determine a) the amount of change of the resonant frequency depending on the excitation amplitude of the exciting magnetic field and/or b) the velocity of change of the resonant frequency depending on the excitation amplitude of the exciting magnetic field based on the induction signal. In an example embodiment it is possible to use these parameters, i.e. a) the amount of change of the resonant frequency depending on the excitation amplitude of the exciting magnetic field and/or b) the velocity of change of the resonant frequency depending on the excitation amplitude of the exciting magnetic field based on the induction signal, to distinguish between at least 64 different values, which provides six bits for encoding the identity of the identification devices.

In an example embodiment the processor is configured to determine a sensitivity of a resonant frequency to an external magnetic field based on the induction signal and to extract the identification data based on the determined sensitivity. In particular, the excitation and induction signal coil system is configured to generate a further magnetic field as the external magnetic field, wherein the processor is configured to determine a change of a frequency and/or of a phase of the induction signals, which is a phase relative to the exciting magnetic field, caused by the generation of the further magnetic field for determining the sensitivity of the resonant frequency to the external magnetic field. The external magnetic field is a DC magnetic field in some embodiments. The main frequency of the induction signals corresponds to the resonant frequency of the identification device. Moreover, at resonance the phase of the induction signals should be about 90° relative to the exciting magnetic field. Thus, based on the induction signal the sensitivity of the resonant frequency to the external magnetic field can be determined in a reliably and technically relatively simple way.

The identification devices can have different sensitivities to the external magnetic field. The external magnetic field adds to the local magnetic field and changes the resonant frequency. For instance, an identification device with a symmetric double string design, i.e. with two filaments holding the respective magnetic object, has very low field sensitivity, while a one-string design has very high sensitivity. It is possible to vary continuously between the designs, for example, by using a two-string design and then continuously varying the string thickness of one of the strings, i.e. of one of the filaments.

In an example embodiment the identifying system comprises a location provider configured to provide a location of the identification device, wherein the excitation and induction signal coil system is configured to generate the further magnetic field as the external magnetic field such that it has a predefined strength at the provided location of the identification device, wherein the processor is configured to determine the change of the frequency and/or of the phase of the induction signals relative to the exciting magnetic field caused by the generation of the further magnetic field having the predefined strength at the provided location of the identification device for determining the sensitivity of the resonant frequency to the external magnetic field.

The location provider can be configured to determine the location of the identification device based on the induction signal and/or by using another localization unit. The location provider can also be a receiving unit configured to receive the location information from another unit such as, for example, a location determination device and to provide the received location information. The location provider can also be a storing unit, such as a memory, in which the location information has been stored and from which the location information can be retrieved for providing the same. The location provider could also be regarded as being a location providing unit that is configured to provide the location.

The location provider and the processor can also be integrated, i.e. the processor can also be configured to determine the location of the identification device, particularly depending on the induction signal.

The read-out procedure, i.e. the determination of the identity of the identification device, can hence involve knowing the location of the identification device and then using the already existing coils or some other field generator of the excitation and induction signal coil system to produce a defined magnetic field at the location of the identification device. The change in frequency or phase, if field generation and frequency detection is not possible simultaneously, is the desired sensitivity. In an example embodiment this allows to distinguish between at least 64 different values, which provides at least six bits for encoding the identity of the identification devices.

In an example embodiment the processor is configured to determine a generation of harmonics of the induction signal due to soft magnetic material of the identification device and to extract the identification data based on the determined generation of harmonics of the induction signal. The respective oscillating magnetic object of the respective identification device can produce quite strong varying magnetic fields in its vicinity. This field can magnetize some magnetically soft material, wherein the magnetically soft material can be soft magnetic needles and/or soft magnetic foils near the oscillating magnetic object within the identification device. In an example embodiment the consideration of the harmonics allows to distinguish between at least 512 different identification devices, which provides at least nine further bits.

Harmonics are generally a non-linear property of the system and they are only seen to a significant fraction, if the excitation amplitude, i.e. the amplitude of the exciting magnetic field, is high enough. In the case of the use of the soft magnetic material the excitation amplitude, where the harmonics generation starts to a significant degree, can be defined more precisely. As long as the soft magnetic material is not in saturation, it does not produce much harmonics over the harmonics that already are there due to the pendulum differential equation as described above. The local field where saturation is reached can be varied by position but most prominently by the cross section of the soft magnetic material. Thus, different identification devices can be distinguished from each other based on the respective excitation amplitude at which the generation of harmonics significantly starts. For instance, it can be determined at which excitation amplitude one or several amplitudes of harmonics in the induction signal exceed one or several thresholds.

The relative strength of the harmonics sensitively depends on the geometry and material type such as, for example, the amount and shape of hysteresis. It is hence possible to provide different identification devices with different relative strengths of harmonics by modifying the geometry and/or the material type of the soft material accordingly. These different relative strengths can therefore also be used to distinguish between different identification devices and hence for encoding the identity of different identification devices. The relative harmonics can be defined, for instance, as a ratio of an amplitude of a certain harmonic to the amplitude at the resonant frequency and/or as a ratio of amplitudes of different harmonics.

The location, orientation, geometry and/or type of the soft magnetic material used in the identification device can also be used to modify the phase angle of the harmonics relative to the oscillation. Thus, the harmonics are complex quantities, wherein not only the amplitude change, but also the phase change, can be used for distinguishing between several identification devices. Particularly, different types of materials having different hysteresis can lead to pronounced phase changes. The phase of a harmonics may be defined relative to the exciting magnetic field, but it can also be defined relative to another signal.

Added DC fields can change the pattern between even and odd harmonics, wherein these different patterns can be used for further distinguishing different identification devices. In some embodiments, these added DC fields are generated by permanent magnetic material at or in the identification device such that the permanent magnetic material influences the soft harmonics generating magnetic material. The permanent magnetic material is hence close to the soft magnetic material, i.e., for instance, adjacent to the soft magnetic material. The permanent magnetic material has the benefit that, if not as hard as FeNdB magnets, an identity code can even be programmed to the identification device by placing it in an appropriate field generator which, for instance, moves the permanent magnetic material, which might be a permanent magnet needle, to certain positions within the identification device. Suitable permanent magnetic materials are hard magnetic materials such as, for example, materials of the barium ferrite type.

It is further preferred that the processor is configured to determine a further property of the identification device and/or of the surrounding of the identification device based on the induction signal. In particular, the processor is configured to determine as the property a property selected from a group consisting of location, orientation, temperature and pressure. Thus, in an example embodiment the identification device does not only provide identity information, but also information about a property such as, for example, the temperature or pressure, wherein the processor is configured to extract the identification data information and the property information. In particular, a first property of the identification device such as, for example, its zero amplitude frequency might be used for providing information about the measured property such as, for example, the measured temperature and a second property of the identification device such as, for example, its magnetic dipole moment might be used for providing its identity. Thus, by determining the first property, for instance, the zero amplitude frequency the measured property such as, for example, the temperature can be provided, wherein known assignments between the zero amplitude frequency and the temperature can be provided, which can be determined by calibration. Moreover, by determining the second property, for instance, the magnetic dipole moment the identity can be provided, wherein known assignments between the magnetic dipole moment and the identity can be provided, which can also be determined by calibration. It is also possible that for different identities different assignments between a) the zero amplitude frequency or another first property and b) the temperature or another property to be measured can be provided.

A distinction between temperature-related effects on an identification device and its identity may be achieved by determining, before performing temperature measurements using the identification device, the identity of the identification device in an environment of which the temperature is known or of which it is known that temperature variations are negligible. Moreover, in contexts where the identifying function of the identification devices is more important than measuring temperature, identifications devices may be provided with additional elements that compensate the effect of temperature changes on the properties of the identification device used for identification.

In another aspect of the present invention a medical tool being equipped with an identification device as defined by any of passive medical identification device embodiments is presented. For instance, the medical tool can be a surgical instrument or another tool, in order to allow to identify the respective surgical instrument or other tool.

In a further aspect of the present invention an identifying method for identifying a medical tool equipped with an identification device as defined by any of of passive medical identification device embodiments is presented, wherein the identifying method comprises:

generating a magnetic field providing a magnetic torque for rotating the magnetic object of the identification device out of its equilibrium orientation and for thereby exciting a rotational oscillation of the magnetic object, the rotational oscillation inducing a response magnetic field, by an excitation and induction signal coil system, transducing the response magnetic field into an induction signal by the excitation and induction signal coil system, receiving the induction signal and extracting identification data by a processor.

In another aspect of the present invention a computer program for identifying a medical tool equipped with an identification device embodiment is presented, wherein the computer program comprises program code unit for causing an identifying system as defined by identification system embodiments to carry out the steps of the identifying method, when the computer program is run on a computer controlling the identifying system.

It shall be understood that the identification device, the holding device embodiment, the combination identification device embodiment, the set of several identification devices embodiment, the use of the identification device embodiment, the identifying system embodiment, the medical tool embodiment, the manufacturing method embodiment, the identifying method embodiment and the computer program embodiment, have similar and/or identical preferred embodiments, in particular, as defined in the dependent claims. In another aspect, a computer-readable medium comprising instructions which, when executed by a computer, cause the computer to carry out the steps of the identifying method.

In some embodiments, an identifying system for identifying a medical tool equipped with a passive medical identification device (1; 101; 201; 301; 401) is disclosed. The system is equipped with a passive medical identification device, which comprises a casing, a magnetic object being arranged within the casing such that it is rotatable out of an equilibrium orientation if an external magnetic torque is acting on the magnetic object, a restoring torque provider being configured to provide a restoring torque to force the magnetic object back into the equilibrium orientation if an external magnetic torque has rotated the magnetic object out of the equilibrium orientation in order to allow for a rotational oscillation of the magnetic object excited by the external magnetic torque, the rotational oscillation generating a response magnetic signal, the casing, magnetic object and the restoring torque provider being arranged such that at least one property of the response magnetic signal is suitable to be used by an identification system to extract identification data from an induction signal. The identifying system also comprises an excitation and induction signal coil system (20, 31) configured to: a) generate a magnetic field providing a magnetic torque for rotating the magnetic object of the identification device out of its equilibrium orientation and for thereby exciting a rotational oscillation of the magnetic object, the rotational oscillation inducing a response magnetic field, and b) transduce the response magnetic field into an induction signal, and comprising a processor configured to receive the induction signal and to extract identification data. In some embodiments, a passive medical identification device is disclosed. The identification device (1; 101; 201; 301; 401) comprises:

a casing (2), a magnetic object (3; 303) being arranged within the casing (2) such that it is rotatable out of an equilibrium orientation if an external magnetic torque is acting on the magnetic object (3; 303), a restoring torque provider (4; 104; 204; 304; 404, 405), wherein the casing, magnetic object and the restoring torque provider being arranged such that at least one property of the response magnetic signal is suitable to be used by an identification system to extract identification data from an induction signal. In some embodiments the passive medical identification device is part of identifying system.

In some embodiments, an identifying system equipped with a passive medical identification device (1; 101; 201; 301; 401) is disclosed, wherein the identifying system comprises:

an excitation and induction signal coil system (20, 31) configured to:

a) generate a magnetic field providing a magnetic torque for rotating the magnetic object (3; 303) of the identification device (1; 101; 201; 301; 401) out of its equilibrium orientation and for thereby exciting a rotational oscillation of the magnetic object (3; 303), the rotational oscillation inducing a response magnetic field, and b) transduce the response magnetic field into an induction signal, and comprising a processor (33) configured to receive the induction signal and to extract identification data.

In some embodiments, a computer-readable medium comprising instructions which, when executed by a computer, cause the computer to carry out the steps of the corresponding method.

In some embodiments, A system comprising the medical identifying system as defined by claim 1 and one or more passive identifying devices is disclosed.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
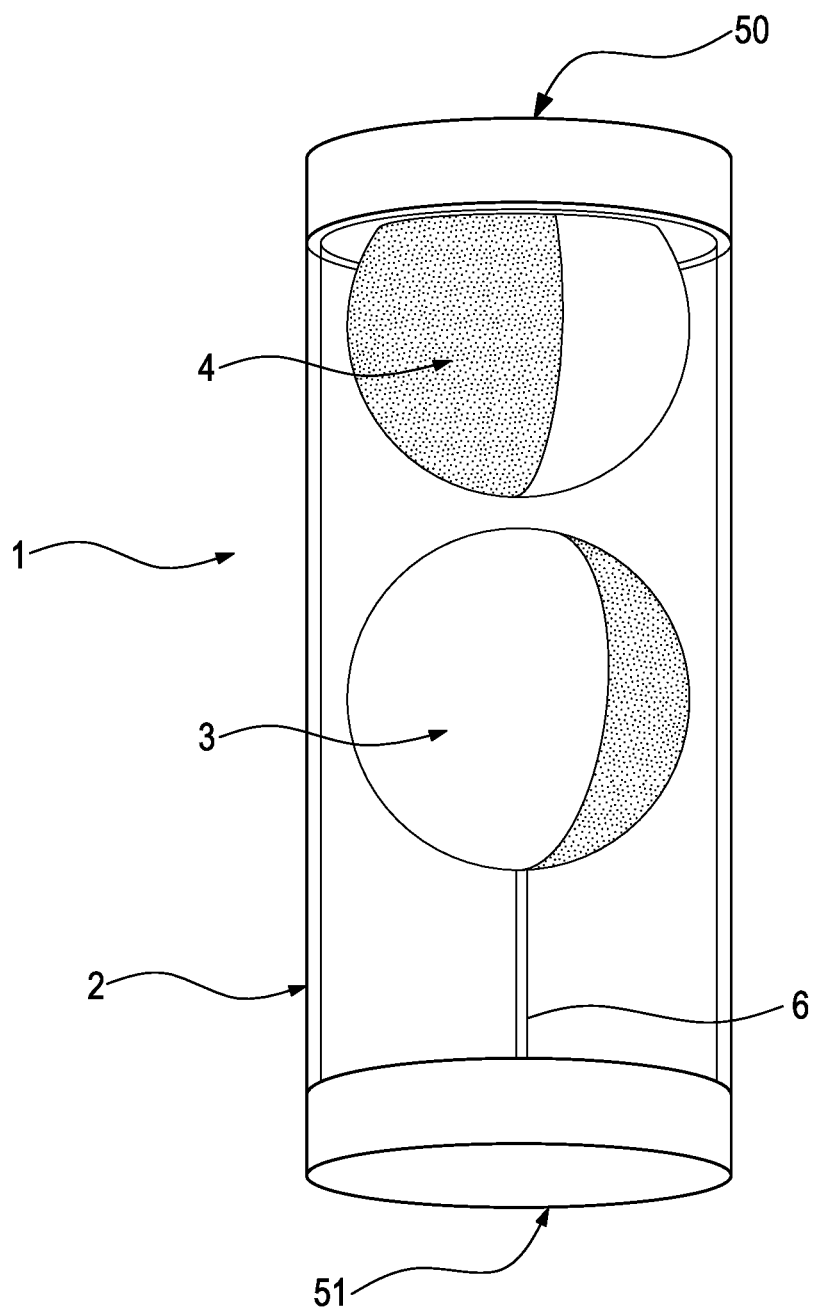
FIG. 1 shows schematically and exemplarily an embodiment of a passive medical identification device, wherein the restoring torque provider comprises a stationary spherical permanent magnet.

FIG. 1 shows schematically and exemplarily an embodiment of a passive medical identification device to be used for identifying a medical tool, if the medical tool is equipped with the identification device. The medical tool is, for instance, a surgical instrument. The identification device 1 comprises a casing 2, a magnetic object 3 being arranged within the casing 2 such that is rotatable out of an equilibrium orientation if an external magnetic torque is acting on the magnetic object 3. The identification device 1 further comprises a restoring torque provider 4 being adapted to provide a restoring torque to force the magnetic object 3 back into the equilibrium orientation if an external magnetic force has rotated the magnetic object 3 out of the equilibrium orientation, in order to allow for a rotational oscillation of the magnetic object 3 excited by the external magnetic torque, wherein the rotational oscillation generates a response magnetic signal. In this embodiment the casing 2 is cylindrical and the magnetic 3 is rotatable around a virtual rotational axis centrally traversing the magnetic object 3, wherein the magnetic object 3 is rotationally symmetric with respect to the virtual rotational axis. In particular, in this embodiment the magnetic object 3 is a magnetic sphere.

The restoring torque provider 4 comprises a further magnetic object 4 for providing the restoring torque. In particular, the magnetic object 3 is attached to one end of a filament 6 wherein another end of the filament 6 is attached to the casing 2. The filament 6 is adapted to prevent the magnetic object 3 from touching the further magnetic 4 due to their magnetic attraction and to allow the magnetic object 3 to rotationally oscillate. In this embodiment the further magnetic object 4 is stationarily attached to the casing 2. The magnetic object 3 forms a first magnetic dipole, the further magnetic object 4 forms a second magnetic dipole and the magnetic object 3 and the further object 4 are arranged such that in the equilibrium orientation the first and second magnetic dipoles point in opposite directions. In some embodiments, the first magnetic object 3 and the second magnetic object 4 are permanent magnets, wherein in the equilibrium orientation a north pole of the magnetic object 3 faces a south pole of the further magnetic object 4 and vice versa.

The casing 2 is cylindrical, wherein the cylindrical casing comprises two end surfaces 50, 51 and wherein the further object is stationarily attached to a first end surface 50 and the end of the filament 6, which is opposite to the end attached to the magnetic object 3, is attached to the second surface 51 of the cylindrical casing 2.

Figure 2:
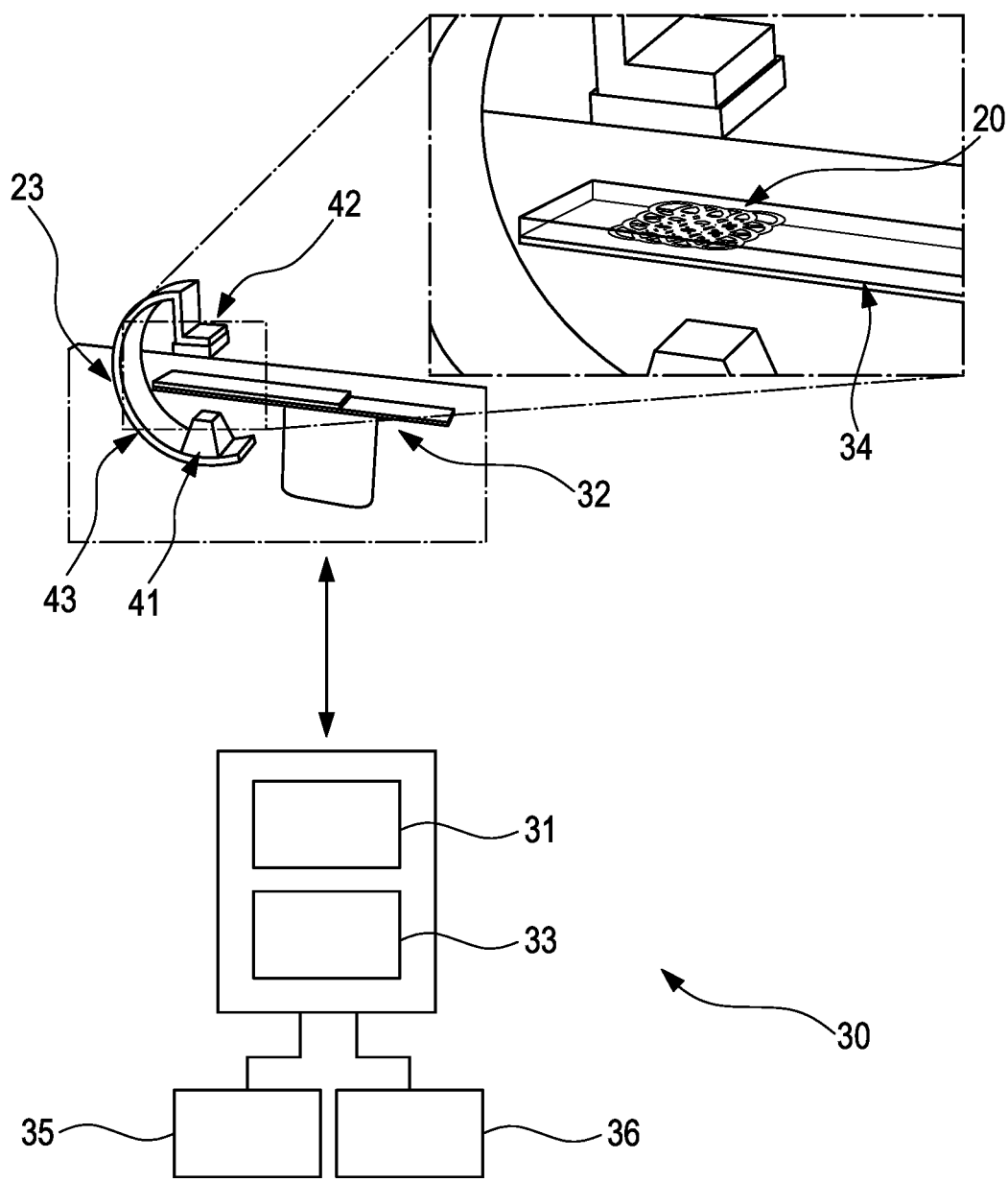
FIG. 2 shows schematically and exemplarity an embodiment of an identifying system for identifying a medical tool equipped with a passive medical identification device together with an imaging system.

The identification device 1 can be attached to the medical tool to be identified, wherein for identifying the identification device and hence the medical tool an identifying system can be used as schematically and exemplarily shown in FIG. 2.

In an example embodiment the identifying system 30 comprises coils 20 adapted to a) generate a magnetic field providing a magnetic torque for rotating the magnetic object 3 of the identification device 1 out of its equilibrium orientation and to thereby excite the rotational oscillation of the magnetic object 3, wherein the rotational oscillation induces a response magnetic field, and b) transduce the response magnetic field into an induction signal.

The identifying system further comprises an identifying controller 31 being configured to control the coils 20 by providing and controlling the current for the coils such that the desired magnetic field is generated and to generate digital induction signals being indicative of the induction influences on the currents within the coils 20 caused by the rotational oscillation of the identification device 1. The coils 20 and the identifying controller 31 magnetically excite the identification device 1 and generate induction signals such that the coils 20 and the identifying controller 31 can be regarded as forming an excitation and induction signal coil system 20, 31.

In this embodiment the coils 20 are arranged in a mat 34 on a support being, in this example, a patient table. However, the coils 20 could also be arranged in or at another part of the identifying system. For instance, the coils 20 may also be arranged in a handheld device such that the identifying system could be carried in a hand.

Although in this embodiment the same coils 20 are used for generating the magnetic field and for generating the induction signals, in other embodiments it is also possible that a) first coils are used for generating the magnetic field providing the magnetic torque for rotating the magnetic object 3 of the identification device 1 out of its equilibrium orientation and for thereby exciting the rotational oscillation of the magnetic object 3 and b) second coils are used for generating the induction signals that depend on the identity of the identification device and hence of the medical tool equipped with the identification device, wherein the first and second coils are separated. Also the first coils and/or the second coils can be arranged in a mat, in a handheld device or in another manner.

For each coil induction signals are generated, which depend on the identity of the identification device 1, wherein a processor 33 of the identifying system 30 is adapted to extract the identification data of the identification device 1 based on the induction signals. The determined identity of the identification device 1 and hence of the medical tool being equipped with the identification device 1 can be output by an output unit 36 which might be an acoustical output unit and/or an optical output unit such as, for example, a display. The identifying system 30 also comprises an input unit 35 such as, for example, a keyboard, a touchpad, a specific button of the system, et cetera, which allows a user to, for instance, start and/or stop an identifying procedure.

In order to distinguish different objects from each other and thereby identify them, different identification devices are provided, which lead to different induction signals. In a calibration procedure for each identification device induction signals can be generated and these induction signals or at least characteristics of these induction signals can be stored. After this calibration has been completed, the processor 33 can use the stored induction signals or the stored characteristics of the induction signals for determining the identity of the respective identification device based on the currently generated induction signals and the stored information. The processor 33 can of course also be adapted to extract the identification data of the respective identification device depending on the induction signals in another way, for instance, based on analytical models, especially functions, which are based on physical considerations and which provide the identity of the respective identification device as an output if as an input the induction signals are given. It is also possible to use artificial intelligence such as, for example, a neural network for providing the identity of the respective identification device depending on the induction signals, wherein the artificial intelligence can be trained by using the stored calibration information.

In an example embodiment, in order to provide different identification devices 1 leading to different induction signals, the casing 2 and/or the filament 6 can be elastic such that the distance between the magnetic object 3 and the further magnetic object 4 is changeable depending on the magnetic attraction between the magnetic object 3 and the further magnetic object 4, wherein different identification devices 1 can have different degrees of elasticity, which might also be regarded as different degrees of softness, of the casing 2 and/or the filament 6. The change of this distance also leads to a change of the resonant frequency of the respective identification device 1 and hence to corresponding changes in the induction signals. Thus, the degree of elasticity or softness of the casing 2 and/or of the filament 6 can be measured by measuring the change in resonant frequency, wherein this change can be used for identifying the respective identification device 1. Also how fast this distance and therefore the resonant frequency changes, i.e. the time constant, is "visible" in the generated induction signals and can hence be used for identifying the respective identification device 1. Different degrees of elasticity or softness can be provided by using, for instance, different kinds of rubber materials, different amounts of rubber material, a bellow-like structure, and/or another elastic material. In an example embodiment, the side walls of the casing 2 comprise or are made of a rubber hose which might be a silicone rubber hose. It is also possible to use a polymer coating such as, for example, a parylene coating and/or a metal coating on, for instance, the rubber hose, wherein these coatings can be different in order to provide different degrees of elasticity or softness.

In an example embodiment the casing 2 is filled with a fluid such that the change of the distance between the magnetic object 3 and the further magnetic object 4 is more stable, which allows for an improved identification of the respective identification device 1. In this embodiment the fluid has a relatively low viscosity being smaller than 1 mPas. Different identification devices can have fluids with different degrees of viscosity, in order to further differentiate the different identification devices from each other. In an example embodiment, the identification devices 1 are filled with a mixture of liquids having different viscosities, wherein the ratio of this mixture changes from identification device to identification device for providing different distances between the magnetic object 3 and the further magnetic object 4. In particular, the identification devices 1 can be filled with different mixtures of hydrocarbons having different viscosities. In an example embodiment pentane is mixed with decane in different ratios, in order to provide different viscosities for different identification devices. The fluid within the casing 2 can also be a gas, wherein a gas mixture can be used for providing different degrees of viscosity such as, for example, a mixture of hydrogen and neon.

The processor 33 can hence be adapted to determine the resonant frequency of the respective identification device 1 based on the frequency of the induction signal and to extract the identification data based on the determined resonant frequency. For instance, the processor 33 can comprise assignments between a) resonant frequencies and b) identities and be configured to extract the identification data of the respective identification device 1 depending on the assignments and the determined resonant frequency.

In an example embodiment a set of identification devices is provided, of which the resonant frequencies cover a range of about 2 kHz, wherein the identifying system is configured to determine the frequency of the induction signals and hence the resonant frequency with an accuracy of 1 Hz. In this embodiment it is possible to distinguish between about 2000 identification devices, which corresponds to about eleven bits which could be used for encoding the identity of the respective identification device.

In FIG. 2 the identifying system 30 is shown together with an imaging system 23 adapted to generated an image of a subject who is arranged on a support 32 such as, for example, a patient table and to whom the surgical procedure is applied. In this embodiment the imaging system 23 is C-arm imaging system for generating two-dimensional and/or three-dimension images of the subject. The C-arm system 23 comprises an x-ray source 41 and an x-ray detector 42 attached to opposing ends of a C-like support structure 43. During the surgical procedure a surgical instrument might be used, which can be equipped with one of the identification devices 1, in order to allow for an identification of the surgical instrument during the surgical procedure and to verify that the correct surgical instrument is used for the respective surgical procedure.

Figure 3:
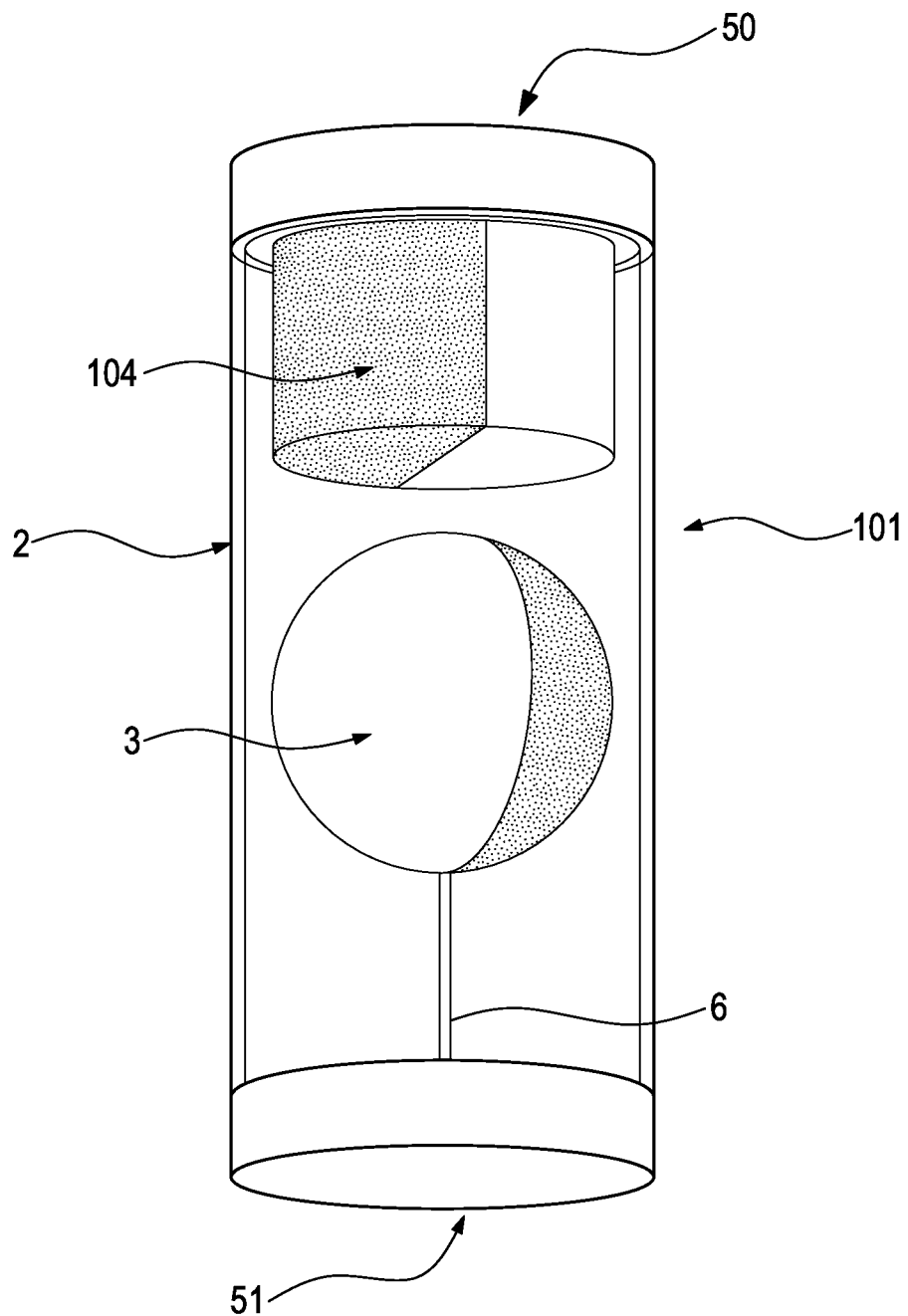
FIG. 3 shows schematically and exemplary a further embodiment of a passive medical identification device, wherein the restoring torque provider comprises a stationary cylindrical permanent magnet.

FIG. 3 shows schematically and exemplarily a further embodiment of an identification device 101 to be identified by the identifying system 30. The identification device 101 is similar to the identification device 1 schematically and exemplarily illustrated in FIG. 1 with the difference that the further magnetic object 104 of the identification device 101 is cylindrical and the further magnetic 4 of the identification device 1 spherical. Also of this embodiment different identification devices 101 generating different induction signals can be provided by using, for instance, different casings 2 having different degrees of elasticity or softness and/or having different fluids with different viscosities filled in the casing 2.

Figure 4:
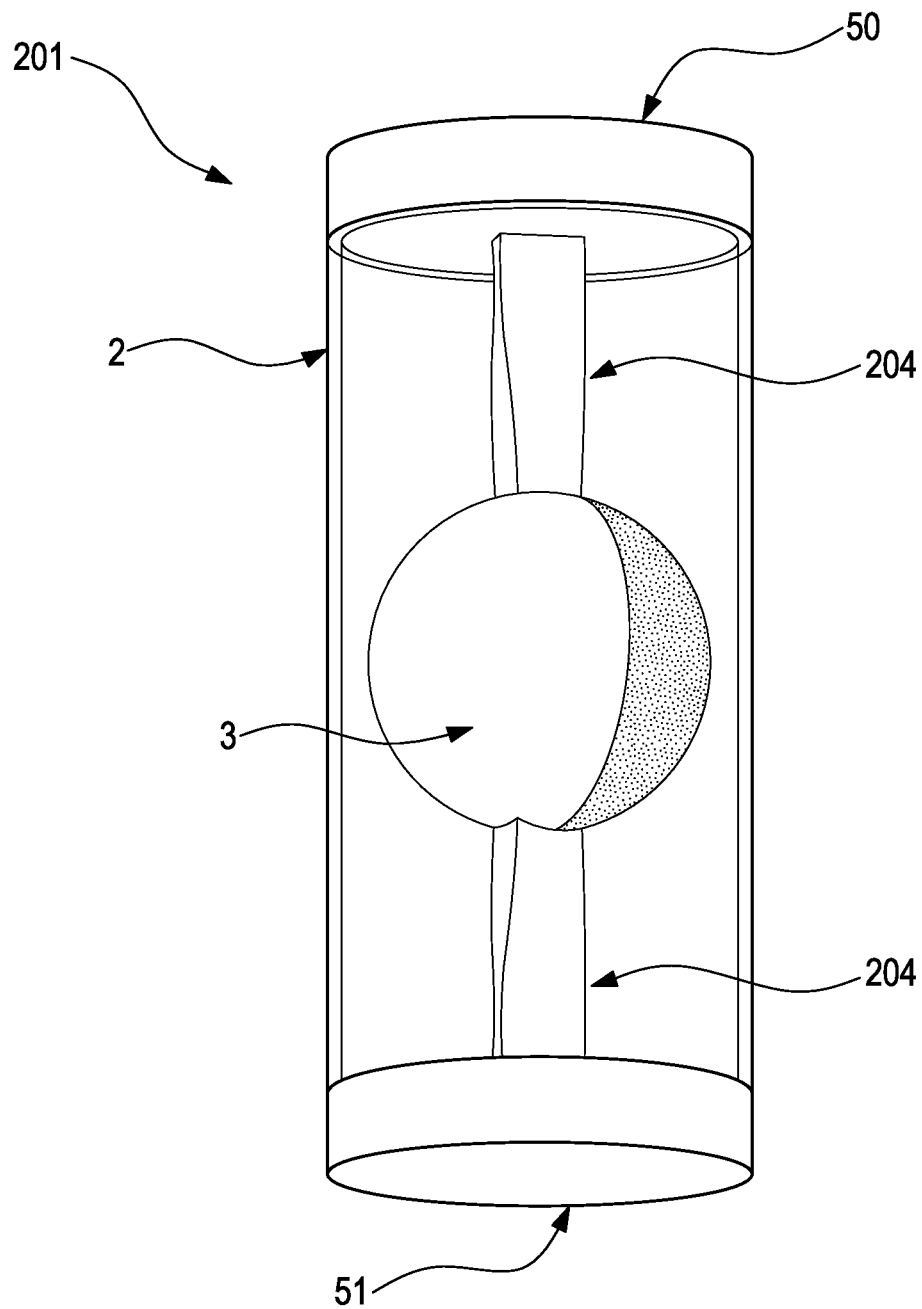
FIG. 4 shows schematically and exemplary a further embodiment of a passive medical identification device, wherein the restoring torque provider comprises a torsional spring mechanism and a rotationally oscillating magnetic object is spherical.

A further embodiment of an identification device 201 is schematically and exemplarily illustrated in FIG. 4. Also in this embodiment the identification device 201 comprises a cylindrical casing 2 and a spherical magnetic object 3 being arranged within the casing 2 such that it is rotatable out of an equilibrium orientation if an external magnetic torque is acting on the magnetic object 3. However, in this embodiment the restoring torque provider 204 differs from the restoring torque provider described above with reference to FIGS. 1 and 3.

The restoring torque provider 204 of the identification device 201 is also configured to provide a restoring torque to force the magnetic object 3 back into the equilibrium orientation if an external magnetic force has rotated the magnetic object 3 out of the equilibrium orientation, in order to allow for a rotational oscillation of the magnetic object 3 excited by the external magnetic torque. Moreover, also in this embodiment the magnetic object 3 is rotatable around a virtual rotational axis centrally traversing the magnetic object 3, wherein the magnetic object 3 is rotationally symmetric with respect to the virtual rotational axis. In particular, also in this embodiment the magnetic object 3 is a magnetic sphere. However, the restoring torque provider 204 comprises a torsional spring mechanism for providing the restoring torque. In particular, the torsional spring mechanism comprises two torsional springs 204, wherein one of these torsional springs 204 attaches the magnetic sphere 3 with the first end surface 50 of the cylindrical casing 2 and the other torsional spring 204 attaches the magnetic sphere 3 to the second end surface 51 of the cylindrical casing 2.

Figure 5:
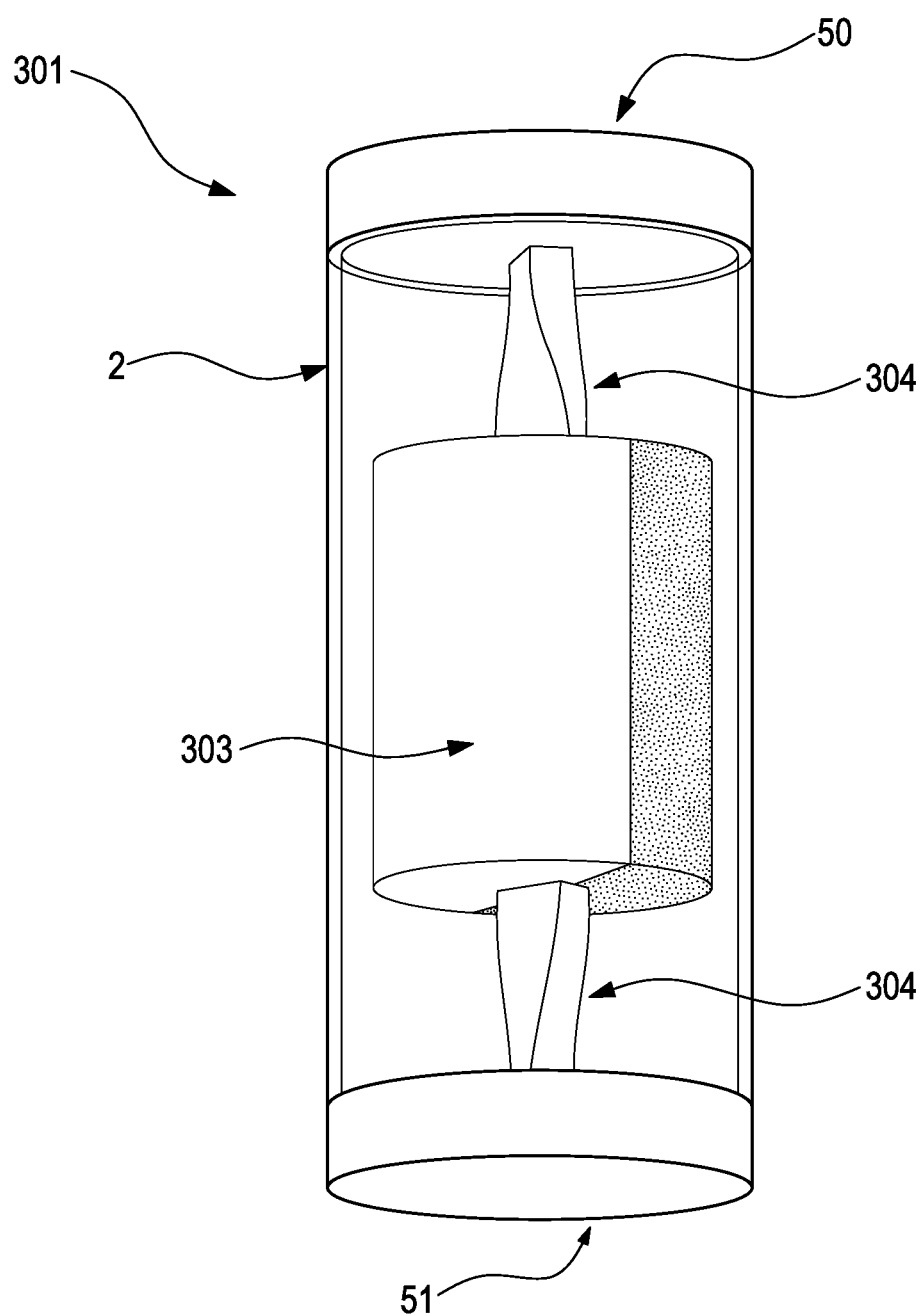
FIG. 5 shows schematically and exemplary a further embodiment of a passive medical identification device, wherein the restoring torque provider comprises a torsional spring mechanism and a rotationally oscillating magnetic object is cylindrical.

FIG. 5 shows schematically and exemplarily a further embodiment of an identification device 301, which is similar to the identification device 201 described above with reference to FIG. 3 with the difference that the identification device 301 comprises a cylindrical magnetic object 303, whereas the identification device 201 comprises a spherical magnetic object 3. Moreover, the torsional springs 304 of the identification device 301 for providing the torsional spring mechanism are shorter than the torsional springs 204 of the identification device 201.

Figure 6:
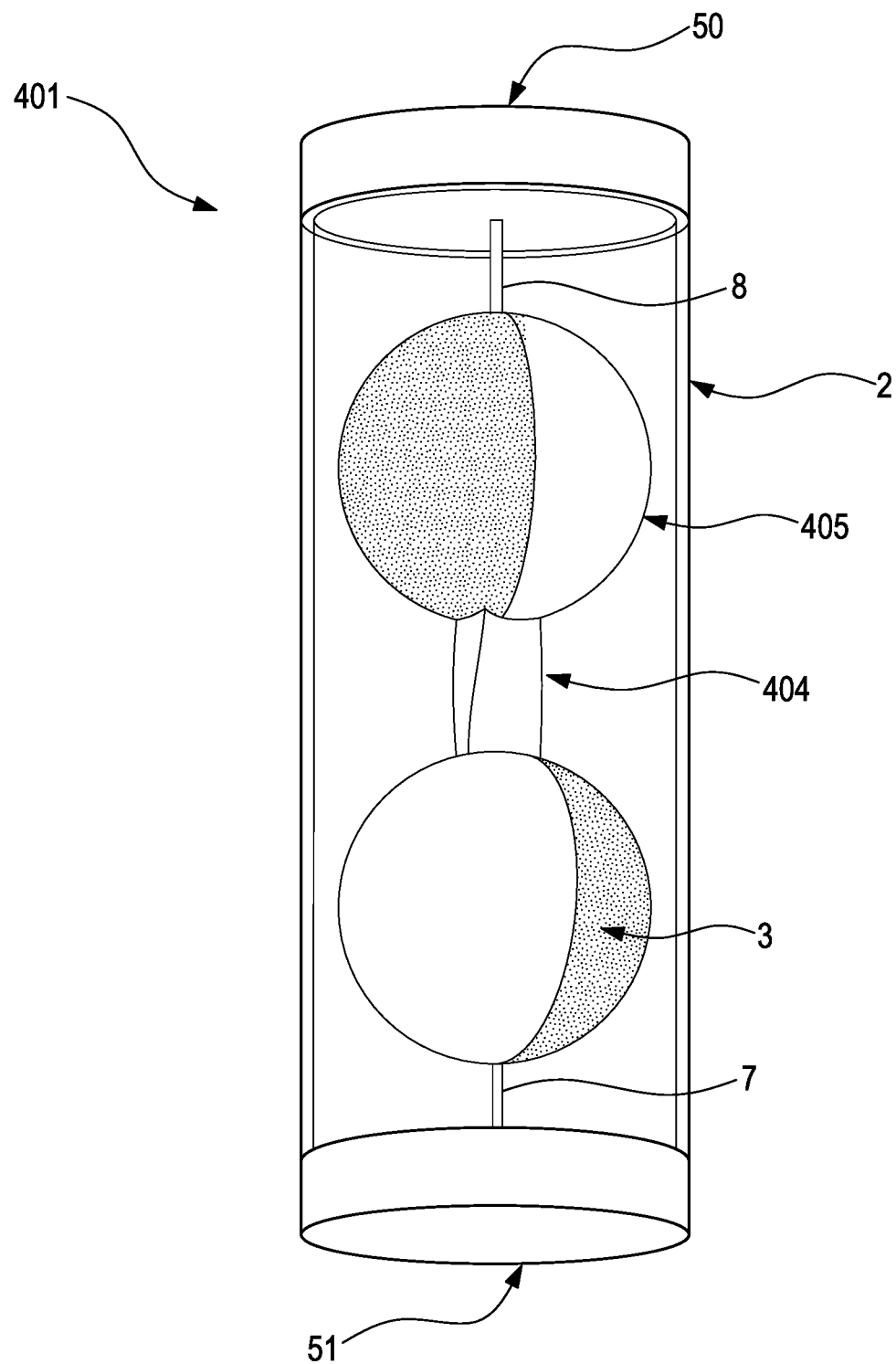
FIG. 6 shows schematically and exemplary a further embodiment of the passive medical identification device, wherein the identification device comprises two rotationally oscillating spherical permanent magnets.

A further embodiment of the identification device 401 is schematically and exemplarily illustrated in FIG. 6. The identification device 401 also comprises a cylindrical casing 2 and a magnetic object 3 being arranged within the casing 2 such that it is rotatable out of an equilibrium orientation if an external magnetic torque is acting on the magnetic object 3. Moreover, also in this embodiment the magnetic object 3 is a magnetic sphere and it is attached to one of two end surfaces 50, 51 via a filament 7. Furthermore, also the identification device 401 comprises a restoring torque provider 404, 405 being configured to provide a restoring torque to force the magnetic object 3 back into the equilibrium orientation if an external magnetic torque has rotated the magnetic object 3 out of the equilibrium orientation, in order to allow for a rotational oscillation of the magnetic object 3 excited by the external magnetic torque. Moreover, also in this embodiment the magnetic object 3 is rotatable around a virtual rotational axis centrally traversing the magnetic object 3, wherein the magnetic object 3, being a magnetic sphere in this embodiment, is of course rotationally symmetric with respect to the virtual rotational axis.

Also in this embodiment the restoring torque provider comprises a torsional spring mechanism 404 for providing the restoring torque, wherein in this embodiment the torsional spring mechanism 404 is provided by a torsional spring connecting the magnetic object 3 and a further magnetic object 405 to each other. Moreover, the restoring torque provider can be regarded as also comprising the further magnetic object 405 for providing the restoring torque, wherein the further magnetic object 405 is also a magnetic sphere. The further magnetic object 405 is arranged within the casing such that it is rotationally oscillatable relative to the casing 2, wherein the further magnetic object 405 is rotatable around a virtual rotational axis centrally traversing the further magnetic object 405. The virtual axes of the magnetic object 3 and the further magnetic object 405, along which the magnetic object 3 and the further magnetic object 405, respectively, are rotatable, are aligned with each other. Moreover, the further magnetic object 405 is attached to one end of a filament 8, wherein another end of the filament 8 is attached to the other of the two end surfaces 50, 51 of the cylindrical casing 2.

In a further embodiment the torsional spring mechanism 404 can also be omitted. Thus, the further magnetic object 405 can also be arranged within the casing 2 such that it is rotationally oscillatable relative to the casing 2, without being directly mechanically connected to the magnetic object 3 via, for instance, a torsional spring mechanism. The further magnetic object 405 is hence rotatable around a virtual rotational axis centrally traversing the further magnetic object 405, wherein the further magnetic object 405 is rotationally symmetric with respect to the virtual rotational axis.

Also the embodiments shown in FIGS. 4 to 6 can have different casings 2 with different degrees of elasticity or softness, in order to allow to distinguish different identification devices of a same embodiment from each other based on the generated induction signals. Moreover, also for these embodiments different fillings of the casings 2 can be provided, which have different viscosities, in order to distinguish different identification devices of a same embodiment based on the generated induction signals.

Figure 7:
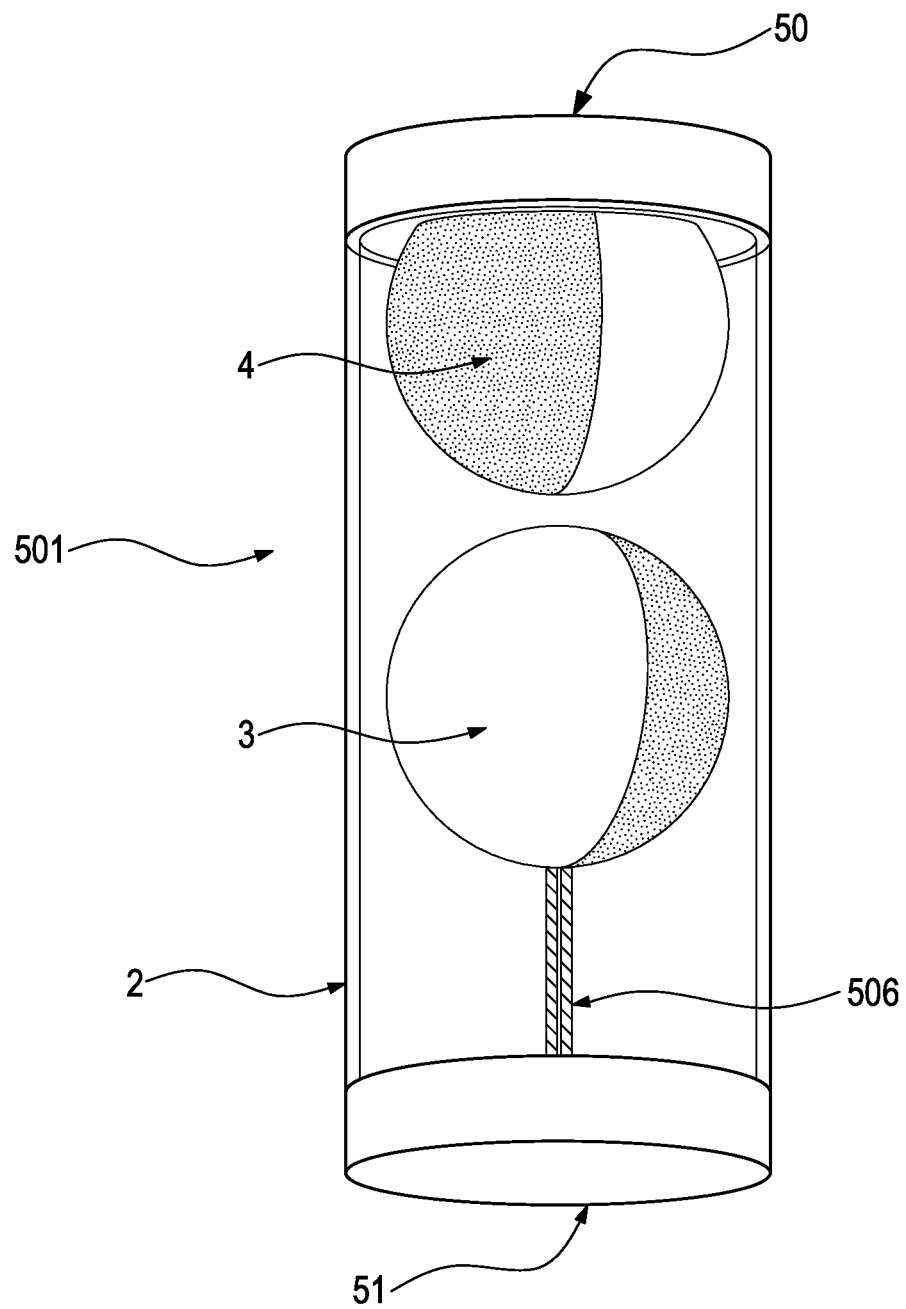
FIG. 7 shows schematically and exemplary a further embodiment of a passive medical identification device, wherein a rotationally oscillating permanent magnet is attached to a casing by using two filaments.

In a further embodiment 501 of the identification device the magnetic object 3 can be attached to the casing 2 by using at least two filaments 506 as illustrated in FIG. 7. Thus, different identification devices can differ from each other with respect to the number of filaments used for attaching the magnetic object 3 to the casing 2. Whether a respective identification device has one or two filaments can be determined, for instance, by measuring the sensitivity of the resonant frequency of the respective identification device 2 to an external field, particularly to an external temporally constant magnetic field, i.e. to a DC magnetic field. For example, if only a single filament is used, the sensitivity of the resonant frequency to the external magnetic field is relatively high, whereas the sensitivity is relative low for an identification device having two filaments. Thus, also this sensitivity can be used for identifying the respective identification device. The materials and/or the thicknesses of the filaments can also vary from identification device to identification device, wherein this variation also leads to a variation of the sensitivity of the resonant frequency to the external magnetic field.

In order to determine the sensitivity of the resonant frequency to the external magnetic field, the excitation and induction signal coil system 20, 31 can be adapted to generate a further magnetic field as the external magnetic field, wherein the processor 33 can be adapted to determine a change of a frequency and/or of a phase of the induction signals, which is a phase relative to the exciting magnetic field, caused by the generation of the further magnetic field. The main frequency of the generated induction signals corresponds to the resonant frequency of the identification device, wherein the resonant frequency can also be found by measuring the phase of the induction signals relative to the exciting magnetic field, because at resonance this phase should be about 90 degrees. Thus, based on the generated induction signals the sensitivity of the resonant frequency to the further magnetic field can be determined, wherein the further magnetic field adds to the local magnetic field and changes the resonant frequency.

In an example embodiment the processor 33 can be configured to determine the location of the identification device based on the induction signals. The processor 33 can hence also be regarded as being a location provider configured to provide a location of the identification device. The excitation and induction signal coil system 20, 31 can be adapted to generate the further magnetic field as the external magnetic field such that it has a predefined strength at the provided location of the identification device, wherein the processor 33 can be adapted to determine the change of the frequency and/or of the phase of induction signals relative to the exciting magnetic field caused by the generation of the further magnetic field having the predefined strength at the provided location of the identification device for determining the sensitivity of the resonant frequency to the external magnetic field. In another embodiment the location provider can be a separate unit, i.e. a unit not being integrated or identical to the processor. This separate location provider can be adapted to determine the location of the identification device based on the induction signals and/or by using other localization units. The separate location provider can also be a receiving unit configured to receive corresponding location information from another unit such as a location determination device and to provide the received location information. The separate location provider can also be a storing unit, such as a memory, in which the location information has been stored and from which the location information can be retrieved for providing the same. The read-out procedure, i.e. the determination of the identity of the identification device, can hence involve knowing the location of the identification device and then using the already existing coils or some other field generator of the excitation and induction signal coil system to produce a defined magnetic field at the location of the identification device. The change in frequency or phase, if field generation and frequency detection is not possible simultaneously, is the desired sensitivity. In an example embodiment this allows to distinguish between at least 64 different values, which provides at least six bits for encoding the identity of the identification devices.

In order to determine the location and also an orientation of an identification device based on the induction signals, for each coil induction signals can be generated, which depend on the location and orientation of the identification device relative to the respective coil. The determination of the location and orientation can use, for instance, the result of a calibration procedure in which for each location and orientation of the identification device relative to the coils 20 the induction signals can be generated and these induction signals or at least characteristics of these induction signals can be stored. After this calibration has been completed, the stored induction signals or the stored characteristics of the induction signals can be used for determining the location and the orientation of the respective identification device based on currently generated induction signals and the stored information. The location and the orientation of the respective identification device can also be determined depending on the induction signals in another way, for instance, based on analytical models, especially functions, which are based on physical considerations and which provide the location and orientation of the respective identification device as an output if as an input the induction signals are given. It is also possible to use artificial intelligence such as a neural network for providing the location, orientation and identity of an identification device depending on the induction signals, wherein the artificial intelligence can be trained by using the stored calibration information.

Figure 8:
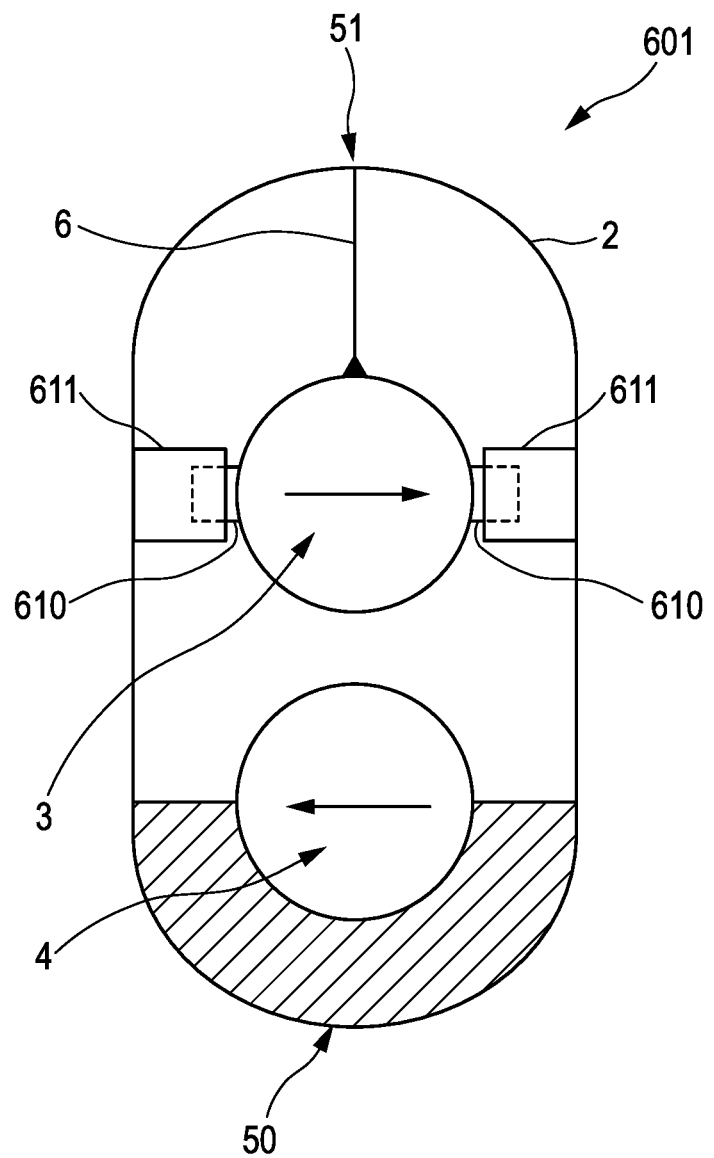
FIG. 8 shows schematically and exemplary a further embodiment of the passive medical identification device, wherein the identification device comprises restriction elements for restricting a maximally possible rotation of a magnetic object out of its equilibrium orientation.

FIG. 8 shows a further embodiment of an identification device 601 comprising a casing 2 with first and second surfaces 50, 51, a rotating magnetic object 3 attached to the casing 2 via a filament 6 and a further magnetic object 4 stationarily attached to the casing 2, particularly to the first surface 50, by using, for instance, glue. In this embodiment the rotating magnetic object 3 is attached to the filament 6 at an attachment location also by using glue. FIG. 8 shows a bulge at the attachment location, which should indicate the glue used for this attachment. However, it is also possible to attach the rotating magnetic object 3 to the filament 6 without having such a bulge. The glue might be a two-components epoxy resin or another type of glue. In the other embodiments the rotating magnetic object might also be attached to a filament by using glue. Moreover, in the other embodiments there might also be a bulge at the attachment location or there might not be such a bulge, i.e. the bulge is optional.

Figure 9:
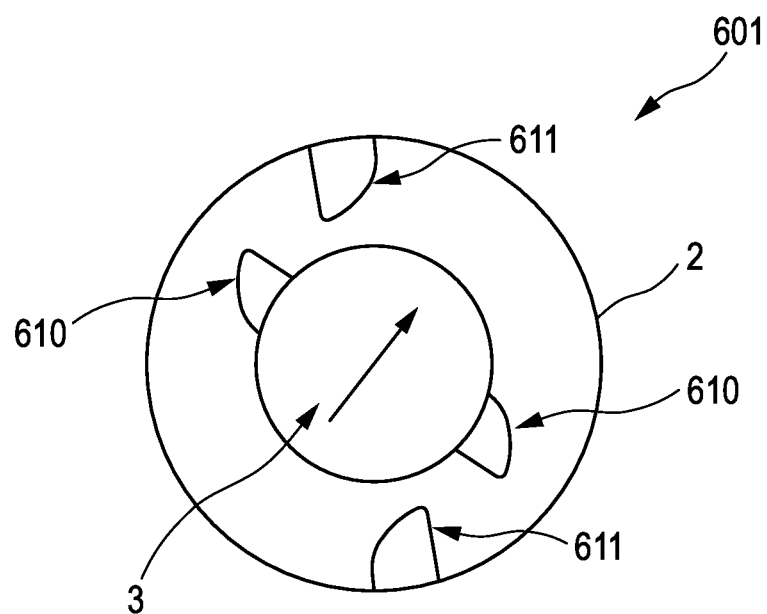
FIG. 9 shows schematically and exemplary a cross sectional view of the embodiment shown in FIG. 8.

In this embodiment the casing 2 and the magnetic object 3 comprise restriction elements 610, 611 for restricting the maximally possible rotation of the magnetic object 3 out of the equilibrium orientation. The maximally possible rotation, which could also be regarded as being a maximum angle of oscillation, can differ between different identification devices and therefore also be used to identify the respective identification device. In this embodiment the casing 2 and the magnetic object 3 each comprise a protrusion 610, 611 which get in touch and prevent a further rotation of the magnetic object 3 out of the equilibrium orientation, if the maximally possible rotation of the magnetic object 3 out of the equilibrium orientation has been reached. In particular, the casing 2 comprises two inner stoppers 611 and the oscillating magnetic object 3 comprises two noses 610 which get in touch with the inner stoppers 611 of the casing 2, if the maximally possible rotation of the magnetic object 3 out of the equilibrium orientation has been reached. In this embodiment the inner stoppers 611 and the noses 610 have an outer curved surface and an opposing outer straight surface, wherein the stoppers 611 and the noses 610 are arranged such that the straight surfaces, i.e. the planar surfaces of the stoppers 611 and the noses 610 get in touch, if the maximally possible rotation of the magnetic object 3 out of the equilibrium orientation has been reached. The straight surfaces of the inner stoppers 611 are perpendicular to the inner surface of the casing 2 and the straight surfaces of the noses 610 are perpendicular to the outer surface of the magnetic object 3, as can be seen in FIG. 9 illustrating a cross section of the identification device 610 shown in FIG. 8.

The processor 33 can be adapted to determine, based on the generated induction signals, the maximum oscillation angle of the respective identification device for identifying the respective identification device. In particular, the processor 33 can be adapted to determine a second harmonic of the induction signals and to determine the maximum oscillation angle based on the determined second harmonic. In an example embodiment a set of identification devices is provided, which have at least 32 different maximum oscillation angles by using, for instance, different positions of the inner stoppers 611 and the noses 610. This provides at least five bits for encoding the identity of the respective identification device.

In an example embodiment the processor 33 can be configured to determine a ratio between a second harmonic and a first harmonic of the generated induction signals and to determine the maximum oscillation angle based on this ratio. The processor 33 can use known assignments such as a table between these ratios and maximum oscillation angles, wherein these assignments can be determined by calibration. The calibration can include measuring this ratio for different known maximum oscillation angles, wherein the first and second harmonics can be determined by Fourier transforming the generated induction signals.

In particular, the processor 33 can be configured to determine a ratio between a second harmonic and a first harmonic of a respective induction signal generated in each of the several coils 20 and to determine the maximum oscillation angle based on the ratios determined for the several coils 20. The known assignments can then correspond to assignments between weighted averages over the ratios determined for the several coils 20 and corresponding maximum oscillation angles. If the assignments are determined by calibration, the calibration can include measuring the several ratios for different oscillation angles and computing corresponding weighted averages. The weights used in the weighted averages, each of which is associated with one of the several coils 20, might be predetermined or adjusted based on an accuracy with which the ratios are determined in the different coils 20, for instance.

In order to determine the maximum oscillation angle of a yet unidentified identification device for identifying the identification device, the several ratios between second harmonics and first harmonics in the respective coils determined for the identification device might be compared to the several ratios assigned to different maximum oscillation angles during calibration, wherein the maximum oscillation angle of the identification device to be identified might be determined to be the one for which the highest similarity is found. The similarity between the ratios determined for the identification device to be identified and the ratios assigned to a given one of the different maximum oscillation angles during calibration might be measured, for instance, in terms of a difference or absolute difference between weighted averages over the respective several ratios, wherein the weights used in the weighted average over the ratios determined for the identification device to be identified preferably correspond to the weights used in the weighted average over the ratios assigned to each of the different maximum oscillation angles during calibration. The similarity between the ratios determined for the identification device to be identified and the ratios assigned to a given one of the different maximum oscillation angles during calibration might also be measured, for instance, in terms of a weighted average over differences or absolute differences between ratios determined for the identification device to be identified and ratios assigned to a given one of the different maximum oscillation angles for corresponding ones of the several coils 20. Also in this case, the weights used in the weighted average, each of which is associated with one of the several coils 20, might be predetermined or adjusted based on an accuracy with which the ratios are determined in the different coils 20.

The processor 33 can also be configured to determine the maximum oscillation angle, which is a maximum angle of the rotating magnetic object 3 relative to its equilibrium orientation in the casing 2, by using a model that describes the generated induction signals depending on, inter alia, the maximum oscillation angle. The processor 33 can be configured to fit this model to the generated induction signals such that a deviation between the generated induction signals and induction signals described by the model are minimized. The model can be, for instance, the above described well known differential equation of a dampened pendulum, wherein the gravitational force is replaced by the magnetic force. Since the model describes the generated induction signals for different maximum oscillation angles, it may also be used for describing the harmonics of the induction signals generated in the several coils 20, particularly the second harmonics or the ratios between the respective second harmonics and first harmonics. Hence, the processor 33 can particularly be configured to fit the model to the second harmonics or ratios between second and first harmonics of the induction signals generated in the different coils such that a respective deviation between the second harmonics or ratios between the second and first harmonics of the generated induction signals and those of the induction signals described by the model are minimized.

Different identification devices can have restriction elements 610, 611 with different impact absorption properties. In particular, the restriction elements 610, 611 can either absorb the energy or act as a reflector, wherein this can add a further bit to the encoding of the identity of the respective identification device. In other words, it can be distinguished between a first identification device comprising absorbing restriction elements and a second identification device comprising reflecting restriction elements, wherein this binary distinguishing can provide a further bit for identifying the respective identification device. It is also possible that different identification devices have stoppers with different degrees of absorption, i.e. not only binary—absorption or no absorption, wherein these different degrees of absorption can be used for distinguishing more identification devices from each other, i.e. for providing more bits for encoding the identity of the respective identification device.

Reflecting restriction elements retain the energy such that a further resonant excitation leads to a frequency increase that can be detected based on the generated induction signals, whereas a further resonant excitation in the energy absorption case, i.e. if the absorbing restriction elements are used, does not lead to a frequency change of the induction signals. If different restriction elements having different degrees of absorption are used in different identification devices, also the frequency changes are different. These frequency changes of the induction signals can be used by the processor 33 to extract the identification data of the respective identification device. In particular, the processor 33 can comprise assignments between frequencies of the induction signals and identifies of the identification devices and use these assignments for determining the identity of the respective identification device based on the frequency of the generated induction signals.

In a further embodiment the identification device can comprise a magnetically soft material. For instance, as schematically and exemplarily illustrated in FIG. 10, an identification device 701 can comprise a magnetically soft needle 710 between the oscillating magnetic object 3 and the further magnetic object 4. The oscillating magnetic object 3 can produce a quite strong varying magnetic field in its vicinity, wherein this varying magnetic field can magnetize the magnetically soft material 710 such that it can reach saturation and therefore produce additional harmonics in the generated induction signals. The type, size, shape, location and orientation of the magnetically soft material relative to the oscillating magnetic object 3 can modify the additional harmonics of the generated induction signals such that, if different identification devices have magnetically soft material of different types and/or with different sizes and/or with different shapes and/or at different locations and/or at orientations relative to the oscillating magnetic object, these identification devices can be distinguished from each other based on the harmonics of the generated induction signals.

Figure 10:
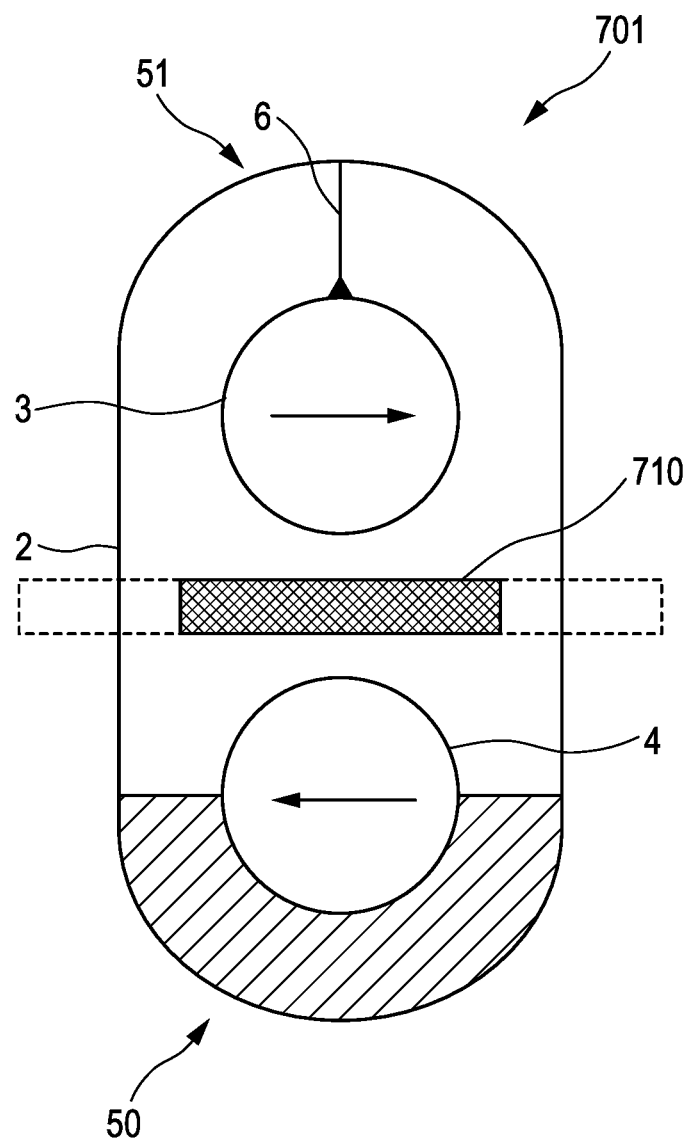
FIG. 10 shows schematically and exemplary a further embodiment of the passive medical identification device, wherein the identification device comprises a needle made of magnetically soft material within a casing of the identification device.

In case the magnetically soft material is provided in the form of a magnetically soft needle 710 as illustrated in FIG. 10, fixing units are preferably provided for fixing the magnetically soft needle 710 with respect to the magnetic object 3. For instance, the magnetically soft needle can be glued to the further magnetic object 4. The glue may be provided by an amount such that the magnetically soft needle 710 is fixed at a predetermined distance from the magnetic object 4 in the direction of the magnetic object 3. This allows to position the magnetically soft needle 710 closer to the magnetic object 3, which leads to a stronger effect of the varying magnetic field produced by the magnetic object 3 on the magnetization of the magnetically soft needle 710 and hence to an earlier saturation. While using glue for fixing the magnetically soft needle 710 already allows for a relatively easy manufacturability of the identification device 701, a more flexible solution may be desired. For instance, fine holes may drilled into the casing 2 opposite to each other, and the magnetically soft needle 710 may be fixed by being inserted into these holes, wherein the magnetically soft needle 710 may be inserted from the outside via one hole first and by then pushing it through to the opposite hole. For facilitating such an insertion process from the outside, the magnetically soft needle 710 may have a length that is greater than an outer diameter of the identification device 701 at the position where the magnetically soft needle 710 is to be inserted, wherein the part or parts of the needle that extends or extend, respectively, outward from the identification device 701 after insertion may be non-magnetic. For instance, the magnetically soft needle 710 may comprise an inner, magnetically soft part that has a length coinciding with the outer diameter of the identification device 701 at the position where the magnetically soft needle 701 is to be inserted, and a non-magnetic part at each side of its inner part that has a length of at least half the diameter, such that the whole magnetically soft needle 710 has a length of at least twice the outer diameter of the identification device 701 at the position where the magnetically soft needle 701 is to be inserted. The non-magnetic part of the magnetically soft needle 701, which is indicated in FIG. 10 by a dashed line, can have any desired length and can also extend into the interior of the identification 701, such that also different lengths of the magnetic part of the soft-magnetic needle 710 can be achieved. After insertion of the magnetically soft needle 710 into the holes of the casing 2, the magnetically soft needle 710 may be further fixed by providing a tight fit, such as a clamping, or glue at the holes. Since, in this way, different needles can be inserted into the identification device 701 in a relatively easy way, a sort of programmability can be achieved.

The processor 33 can be adapted to extract the identification data of the respective identification device based on the harmonics of the generated induction signals in different ways as it will be explained in the following.

Harmonics are generally a non-linear property of a system, which are not seen if an excitation amplitude is relative low, because at relatively low excitation amplitudes the oscillating system behaves substantially linearly. If an identification device comprises soft magnetic material, i.e. magnetically soft material, as long as this soft magnetic material is not in saturation, it does not produce much harmonics over the harmonics that are already there according to, for instance, the above described differential pendulum equation. The excitation amplitude, i.e. the amplitude of the exciting magnetic field, at which the generation of harmonics significantly starts, can be detected by the processor 33 and this respective excitation amplitude can be used for distinguishing between different identification devices. For instance, the processor 33 can be configured to determine at which excitation amplitude of the exciting magnetic field one or several amplitudes of harmonics in the generated induction signals exceed one or several predefined thresholds.

The processor 33 can also be configured to determine relative strengths of the amplitudes of the harmonics and to distinguish between different identification devices based on these relative strengths. For instance, a ratio of an amplitude of a certain harmonic to the amplitude at the resonant frequency and/or a ratio of amplitudes of different harmonics can be used by the processor 33 for distinguishing between different identification devices.

The processor 33 can also be configured to determine the phase angle of the oscillation and to use this phase angle for distinguishing between different identification devices. The harmonics are complex quantities, wherein not only the amplitude of the respective harmonics changes, but also the respective phase changes, wherein these phase changes can be used for distinguishing between different identification devices. The phase is defined relative to the phase of the exciting magnetic field, but the phase of a respective harmonics can also be defined in another way.

The processor 33 might also be configured to estimate the type, size, shape, location and/or orientation of the magnetically soft material relative to the oscillating magnetic object 3 and to use this type, size, shape, location and/or orientation for distinguishing between different identification devices, wherein the type, size, shape, location and/or orientation of the magnetically soft material might be estimated based on the determined relative strengths and/or phase angles of the harmonics.

In an example embodiment the magnetic object 3 comprises a magnetically soft material. For instance, the magnetic object 3 can be made of magnetically soft material. The magnetic object made of magnetically soft material might be a magnetically soft sphere as shown in the figures or a cylinder. It is also possible that a magnetically soft object is used in addition to the magnetic object 3, wherein in this case the magnetic object 3 is made of a magnetically hard material and a permanent magnet. For instance, this additional magnetically soft object can be arranged on top of the magnetic object 3 made of the magnetically hard material. Providing the magnetic object 3 with the magnetically soft material allows for an increased maximally possible rotation of the magnetic object 3 out of its equilibrium orientation, wherein the resulting increased maximum oscillation angle can be detected by the processor 33 and used for identifying the respective identification device as described above.

Figure 11:
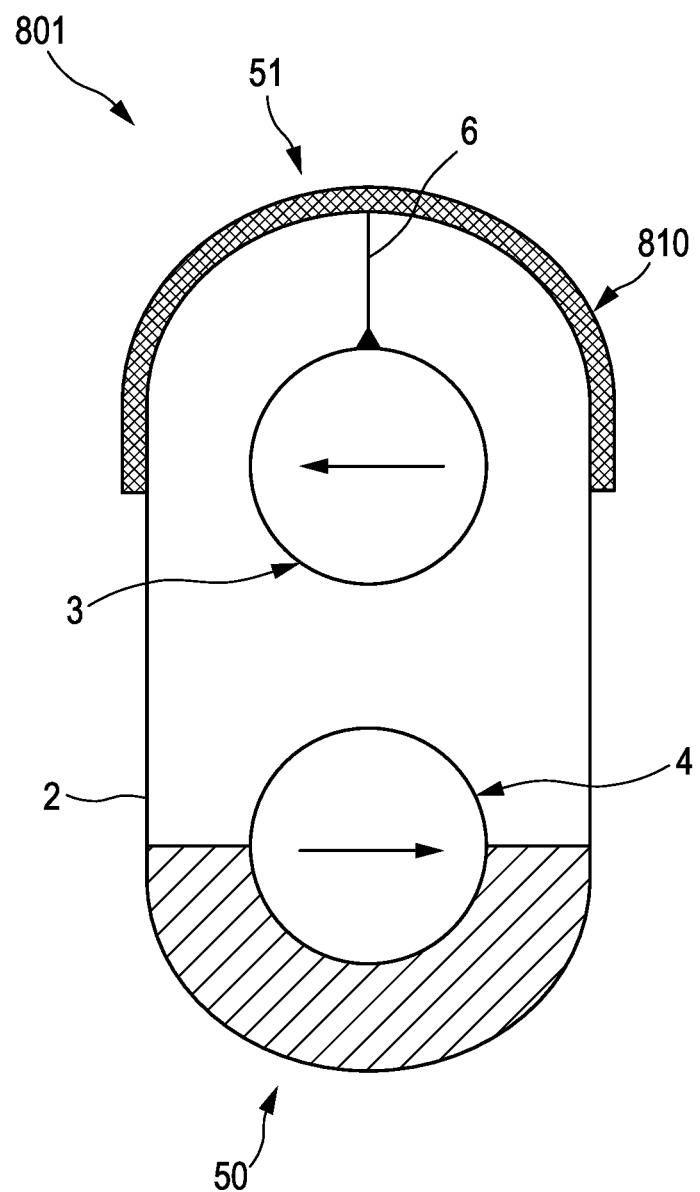
FIG. 11 shows schematically and exemplary a further embodiment of the passive medical identification device, wherein a casing of the identification device is provided with a magnetically soft foil strip on its outside.
Figure 12:
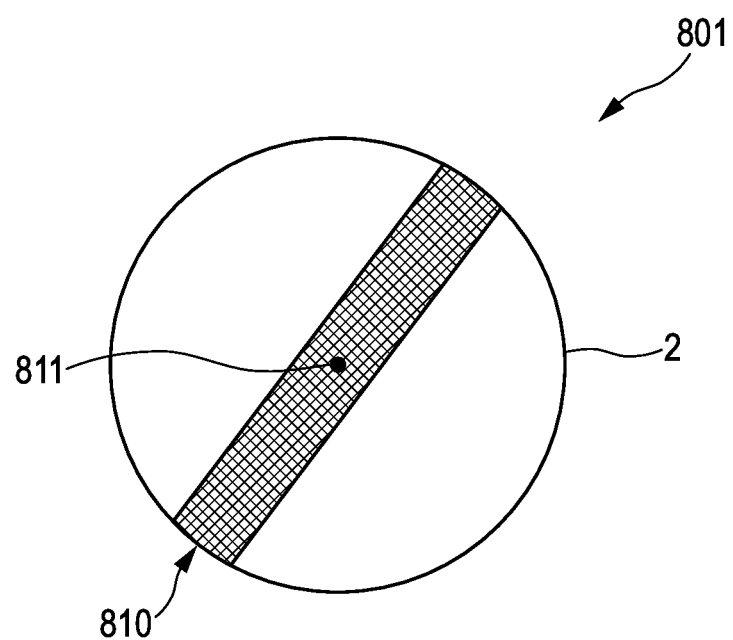
FIG. 12 shows schematically and exemplary a top view on the embodiment shown in FIG. 11.

FIG. 11 shows a further embodiment 801 of an identification device also comprising a rotating magnetic object 3 and a further fixed magnetic object 4 within a casing 2, wherein the magnetic object 3 is attached to the casing 2 via a filament 6. In this embodiment the casing 2 comprises a soft magnetic material 810, i.e. a magnetically soft material 810. The soft magnetic material 810 is in this embodiment a strip arranged on top of the casing 2 such that the strip 810 covers the attachment point 811 of the filament 6 as schematically and exemplarily illustrated in FIG. 12 being a top view of the cross sectional view shown in FIG. 11.

The soft magnetic strip 810 can, such as the soft magnetic needle 710, be magnetically saturated by the varying magnetic field produced by the rotating magnetic object 3, and therefore produce additional harmonics in the generated induction signals. In this case, preferably the orientation of the soft magnetic strip 810 relative to the rotating magnetic object 3, particularly relative to the equilibrium orientation of the magnetic moment of the rotating magnetic object 3, is varied for different identification devices in order to distinguish them from each other based on the different harmonics of the generated induction signals. Since this relative orientation can be relatively easily varied in applying the magnetic strip 810 to the casing 2 and since the effect of the relative orientation on the harmonics of the generated induction signals can be relatively large, a relatively large number of identification devices can be provided that are still sufficiently distinguishable from each other.

The magnetically soft material 810 can focus the external magnetic field and thereby increase the sensitivity of the resonant frequency to the external magnetic field. Thus, different identification devices can be distinguished by providing different amounts of magnetically soft material and/or by providing the magnetically soft material at different locations on the casing 2 or at other places on or within the respective identification device, in order to provide different sensitivities of the resonant frequency to the external magnetic field. It is of course also possible that at least one of the identification devices does not comprise any magnetically soft material. The kind of the magnetically soft material 810 and also of the other magnetically soft materials described with respect to the other embodiments can be a "Permalloy" type nickel iron or a nano-magnetic soft material. The external magnetic field used for determining the sensitivity of the resonant frequency to this field is a temporally constant magnetic field, i.e. a DC magnetic field.

Figure 13:
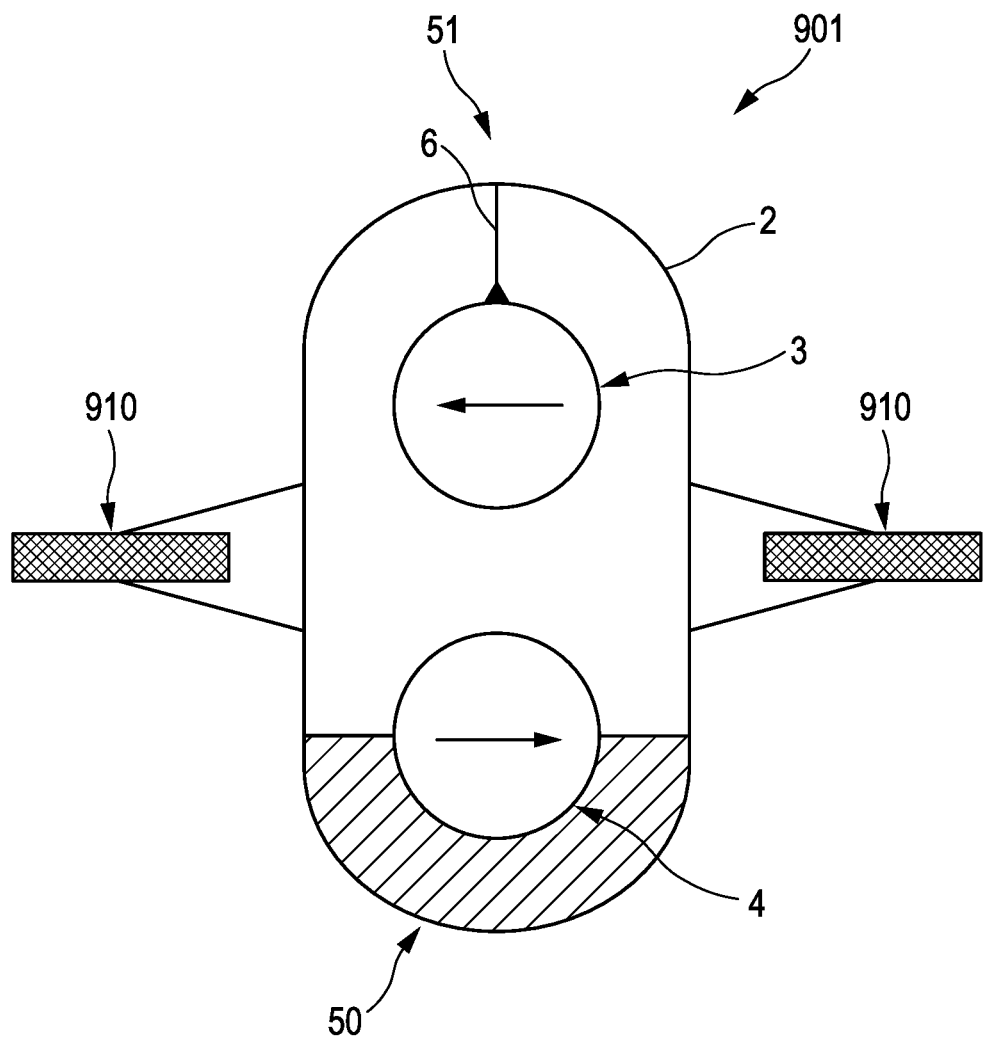
FIG. 13 shows schematically and exemplary a further embodiment of the passive medical identification device, wherein it comprises symmetrically arranged magnetically soft material.

In a further embodiment 901 of the identification device, which is schematically and exemplarily shown in FIG. 13, the magnetically soft material 910 can be provided as symmetric wires on both sides of the oscillating component formed by the rotating magnetic object 3 and the further magnetic object 4, wherein also this arrangement of the magnetically soft material 910 can increase the sensitivity of the resonant frequency with respect to the external magnetic DC field. The symmetric design shown in FIG. 13 has the advantage that forces due to the magnetically soft material 910 on the rotating magnetic object 3 are relatively low. If, for instance, the magnetically soft material were located on one side of the oscillating component only, the magnetic object 3 might be attracted and become stuck to the casing 2. The symmetric wires of soft magnetic material 910 can be fixed to the casing 2 by glue, for instance. As illustrated in FIG. 13, the glue may be provided by an amount such that it stabilizes the symmetric wires against tilting towards the casing 2.

Figure 14:
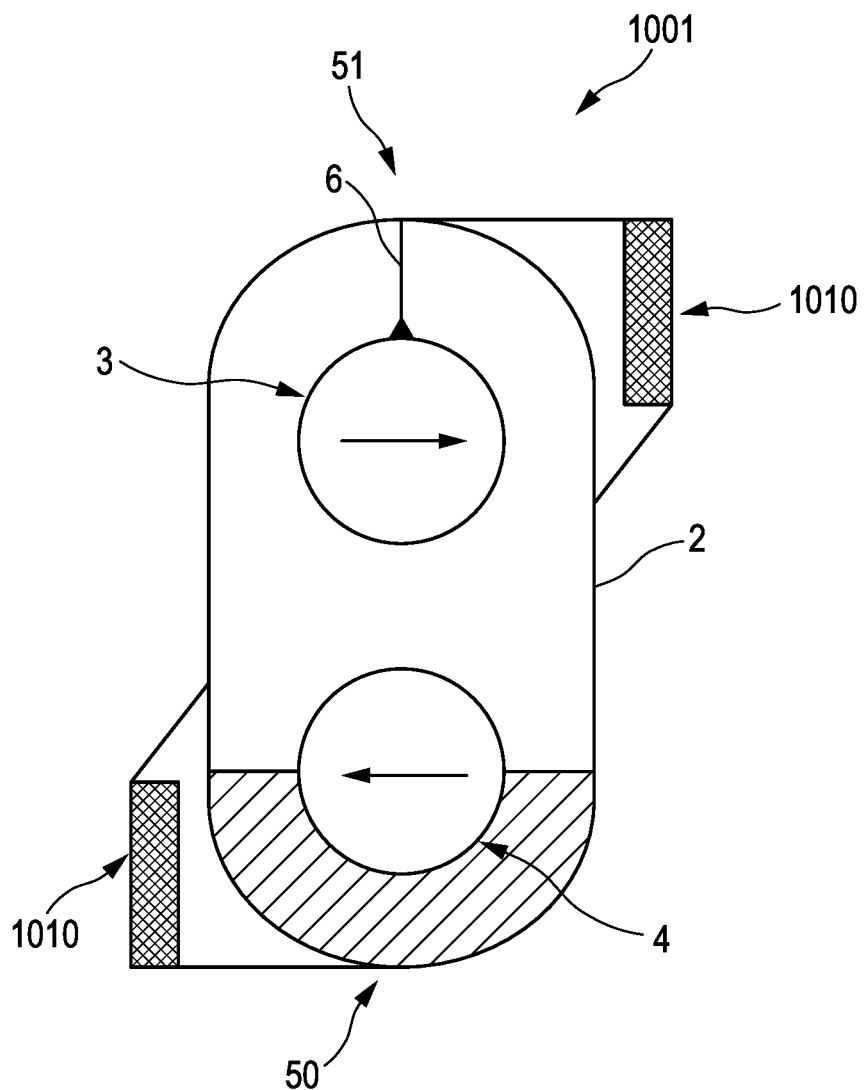
FIG. 14 shows schematically and exemplary a further embodiment of the passive medical identification device, wherein the identification device comprises asymmetrically arranged magnetically soft materials.

FIG. 14 shows schematically and exemplarily a further embodiment 1001 of an identification device, wherein in this embodiment the magnetically soft material 1010 is provided asymmetrically on both sides of the oscillating component formed by the magnetic object 3 and the further magnetic object 4. In some embodiments, the magnetically soft material 1010 is provided as magnetically soft wires. Also the magnetically soft materials 910 illustrated in FIG. 13 can be provided as wires. The asymmetric arrangement of the magnetically soft material 1010 shown in FIG. 14 can lead to a reduced amount of space required for the magnetically soft material 1010. Since, due to the asymmetric arrangement of the magnetically soft material 1010, they have different distances to the magnetic object 3, there can be a magnetic net force caused by the magnetically soft materials 1010 acting on the magnetic object 3. In a preferred embodiment the asymmetrically arranged magnetically soft materials 1010 have within the same identification device 1001 different dimensions, wherein these different dimensions are chosen such that the magnetic net force acting on the magnetic object 3 caused by the magnetically soft material 1010 is reduced and further preferred eliminated. In particular, in a preferred embodiment the magnetically soft material being closer to the magnetic object 3 is smaller than the further magnetically soft material having a larger distance to the magnetic object 3. As illustrated in FIG. 14, also the asymmetrically provided magnetically soft material 1010 can be fixed to the casing 2 by glue, for instance, wherein the glue may be provided by an amount such that it stabilizes the symmetric wires against tilting towards the casing 2.

Figure 15:
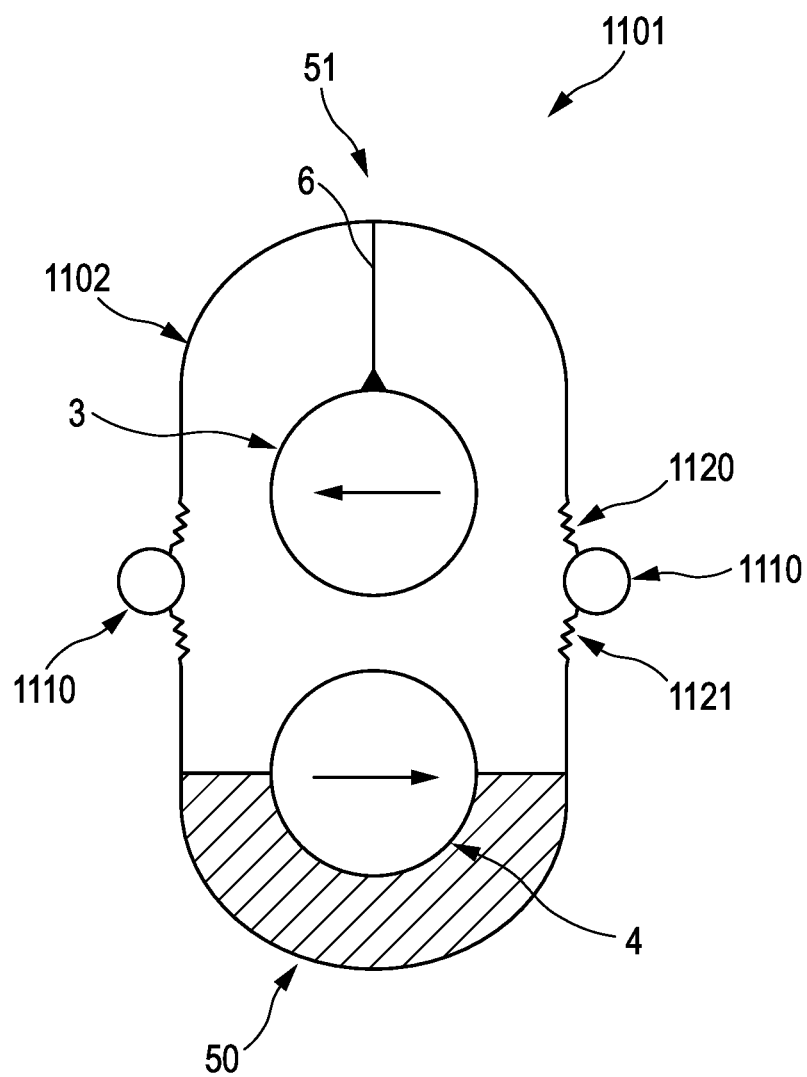
FIG. 15 shows schematically and exemplary a further embodiment of the passive medical identification device, wherein the identification device comprises, in addition to a first oscillator including a rotationally oscillating magnetic object, a further oscillator including an oscillating metal ring.

FIG. 15 shows schematically and exemplarily a further embodiment 1101 of an identification device. In this embodiment the identification device 1101 comprises, besides the magnetic object 3, a further oscillating element 1110 being an oscillating ring. The further oscillating element 1110 is mechanically coupled via a circumferential springy part 1120, 1121 of the casing 1102 to the rest of the casing 1102. In particular, the oscillating ring 1110 is mechanically coupled to the region of the casing 1102 between the circumferential springy part 1120, 1121 and the attachment point of the filament 6 at the casing 1102 via a first circumferential subpart 1120 of the circumferential springy part 1120, 1121, and to the remaining part of the casing 1102 via a second circumferential subpart 1121 of the circumferential springy part 1120 1121. Since the further magnetic object 4 is fixed with glue to the part of the casing 1102 to which the oscillating ring 1110 is mechanically coupled via the second subpart 1121, the oscillating element 1110 is also mechanically coupled to the further magnetic object 4. The filament 6 is preferably thin and/or easily twistable enough to mechanically decouple the magnetic object 3 from all other parts of the identification device 1101 regarding circumferential oscillations, in which case it is preferred that the identification device 1101 is fixed relative to the environment, i.e., for instance, relative to a medical instrument to which the identification device 1101 might be fixed. The magnetic object 3 is then only indirectly coupled magnetically to the other parts of the identification device 1101 via its magnetic coupling to the further magnetic object 4. However, the filament 6 may also be thick enough and/or rigid enough against twists such that it provides a noticeable mechanical coupling between the magnetic object 3 and the part of the casing 1102 to which it is fixed via the filament 6 regarding circumferential oscillations. In some embodiments, the first subpart 1120 and the second subpart 1121 comprise a plurality of bars arranged equidistantly in circumferential direction, each of them fixed with one end to the casing 1102 and with another end to the oscillating ring 1110, wherein the bars allow for a bend such that an oscillation of the oscillating ring 1110 is facilitated in circumferential direction. Accordingly, spring constants can be associated with each of the first subpart 1120 and the second subpart 1121, wherein the spring constants can be tuned by selecting a suitable number of bars, length of the bars, thickness of the bars and/or material of the bars. Instead of bars, also an elastic membrane might be used, for instance.

The first subpart 1120 can be chosen to have a spring constant, which differs from the spring constant of the second subpart 1121. Having different spring constants allows for a wider range of coupling constants and resonant frequencies. For example, for a given resonant frequency, the first subpart 1120 could be made relatively soft. If this is the case, the oscillating ring 1110 may be viewed as a substantially separate inertia provider and the second subpart 1121 has to be relatively soft, providing a relatively low coupling. If the first subpart 1120 is relatively stiff, the oscillating ring 1110 will rotate together with the whole part of the casing to which it is coupled via the first subpart 1120, giving rise to the need of a higher stiffness of the second subpart 1121, which in turn increases the coupling constant. For intermediate stiffness of the first subpart 1120, the whole assembly may have to be viewed as a coupling to a coupled oscillator. This gives rise to more freedoms and more possibilities to encode information, which will be reflected in the model of the identification device 1101.

The springy part 1120, 1121 of the casing 1102, particularly the spring constants of this springy part 1120, 1121, define the resonant frequency of the oscillating ring 1110. Different identification devices 1101 can have oscillating rings 1110 with different resonant frequencies by using a circumferential springy part 1120, 1121 having different spring constants. Thus, it is possible to distinguish different identification devices 1101 based on the resonant frequency of the further oscillating element 1110 of the respective identification device 1101. This resonant frequency can be probed by using the initial oscillator formed by the magnetic object 3 and the restoring torque provider being in this embodiment the further fixed magnetic object 4.

Thus, the excitation and induction signal coil system 20, 31 can be adapted to a) generate the magnetic field providing the magnetic torque for rotating the magnetic object 3 of the identification device 1101 out of its equilibrium orientation with different amplitudes, in order to excite the rotational oscillation of the magnetic object 3 with different excitation amplitudes such that it oscillates with different resonant frequencies, wherein the rotational oscillation generates a response magnetic signal, and b) transduce the response magnetic field into an induction signal that depends on the different excitation amplitudes. Moreover, the processor 33 can be adapted to determine the excitation amplitude, at which the oscillating element 1110 oscillates with its resonant frequency, based on the induction signal and to extract the identification data of the identification device 1101 based on the determined excitation amplitude.

The resonant frequency of the identification device 1101 without the further oscillating element 1110 and the springy part 1120, 1121 of the casing, i.e., the resonant frequency of the magnetic object 3 and the restoring torque provider 4, depends on the excitation amplitude. Thus, by modifying the excitation amplitude of the exciting magnetic field, the frequency, with which the initial oscillator, i.e. the magnetic object 3, oscillates, can be modified. For instance, the frequency of the initial oscillator 3 might be shiftable by about 100 Hz by varying the excitation amplitude of the exciting magnetic field. Thus, the resonant frequency of the initial oscillator 3, 4 can be shifted, wherein, if this resonant frequency meets the resonant frequency of the further oscillating element 1110, the generated induction signals change and this change can be used to extract the identification data of the respective identification device 1101. The processor 33 can be adapted to identify the respective identification device 1101 based on the excitation amplitude at which the change of the induction signals is visible. The identification device 1101 and the identifying system 30 can be configured such that it can be distinguished between at least eight different resonant frequencies of the further oscillating elements 1110 such that in this way at least three bits can be used for encoding the identity of the respective identification device 1101.

The processor 33 can comprise assignments between a) excitation amplitudes of the exciting magnetic field at which the induction signals significantly change and b) resonant frequencies of the further oscillating element 1101 or directly the identities of the identification devices 1101, wherein these assignments and the actually determined excitation amplitude of the exciting magnetic field at which the induction signals significantly change are used for determining the respective resonant frequency of the respective oscillating element 1110 and hence the respective identity. These assignments can be predefined by calibration. Moreover, it can be predefined that the induction signals significantly change, if the change is larger than a predefined threshold. It is also possible that the processor 33 uses artificial intelligence, particularly a neural network, which is trained by using pairs of generated induction signals and resonant frequencies of the further oscillating element 1110 and/or respective identities. The processor 33 can also be adapted to determine the resonant frequency of the further oscillating element 1110 of the respective identification device 1101 by using a model that models the induction signals depending on the resonant frequency of the oscillating element 1110. The generated induction signals correspond to the temporal derivate of the angle of rotation of the magnetic object relative to its equilibrium orientation scaled with a scaling factor, wherein the angle of rotation over time, i.e. the corresponding oscillation of the oscillator formed by the magnetic object 3 and the fixed further magnetic object 4 which is influenced by the oscillation of the oscillating element 1110, can be modelled by using equations such as the above equations (6) to (8), for instance.

In an example embodiment the identification device shown in FIG. 15 can comprise no oscillating ring 1110, wherein the circumferential springy part does not comprise two subparts, but provides a direct mechanical coupling between the part of the casing 1102 to which the magnetic object 3 is fixed via the filament 6 and the remaining, opposite part of the casing 1102. Also in this case the circumferential springy part may comprise a plurality of bars or an elastic membrane.

Figure 16:
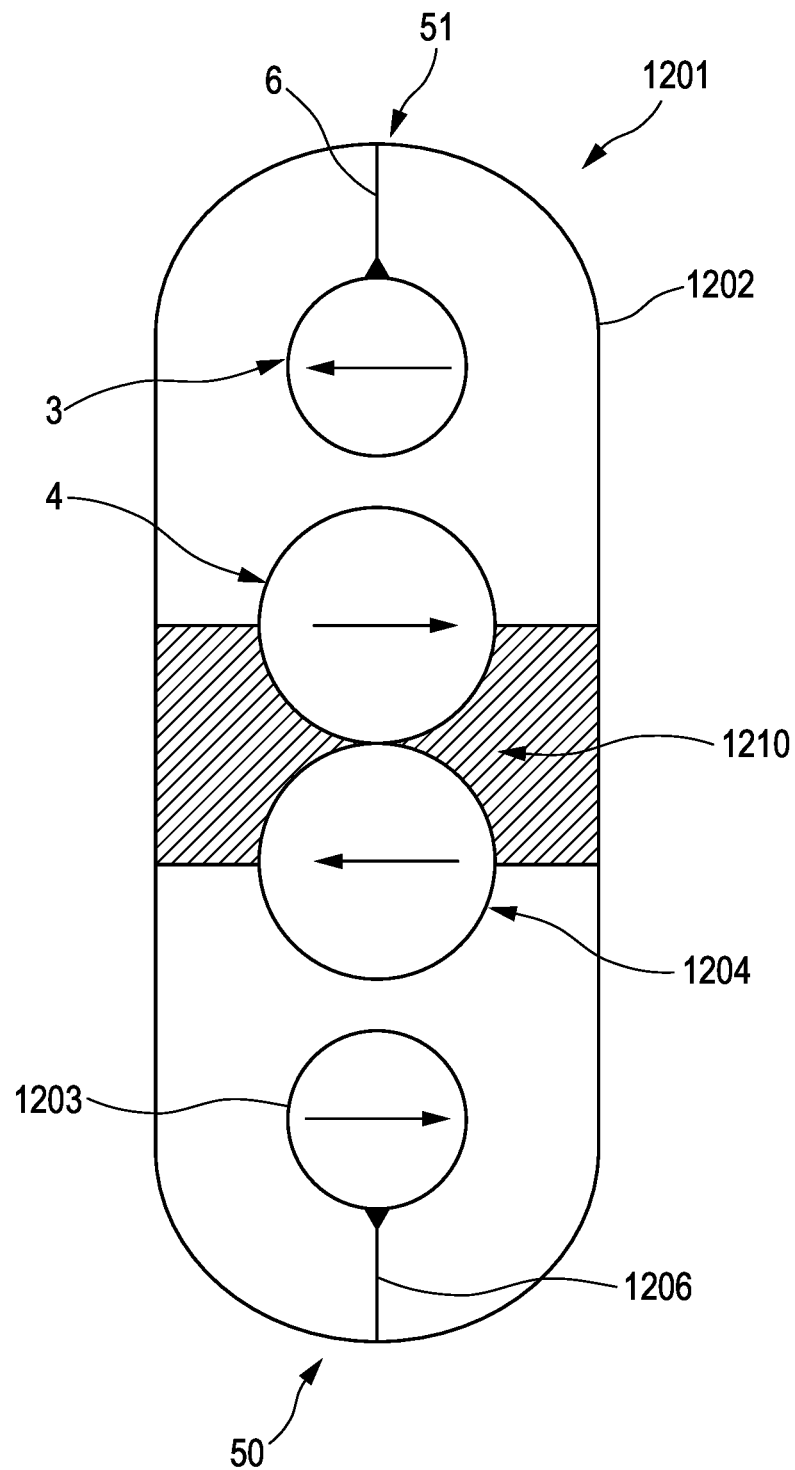
FIG. 16 shows schematically and exemplary a further embodiment of the passive medical identification device, wherein the identification device comprises two magnetic oscillators.

FIG. 16 shows schematically and exemplarily a further embodiment of an identification device. In this embodiment the identification device 1201 comprises a first oscillator formed by the magnetic object 3, which is attached to the casing 1202 via a filament 6, and a restoring torque provider 4 formed by a further magnetic object fixed to the casing 1202 by using a layer 1210 of glue. The layer 1210 of glue is arranged inside and about at half distance between upper and lower ends of the casing 1202. Besides this first oscillator, the identification device 1201 comprises a second oscillator formed by a magnetic object 1203 attached to the casing 1202 via a filament 1206 and formed by a further restoring torque provider 1204 comprising a magnetic object 1204 fixed to the casing 1202 within the layer 1210 of glue. In this embodiment, the first and second oscillators are similar and are arranged at opposing ends within the casing 1202.

In contrast to the previous embodiment, the identification device 1201 of the embodiment shown in FIG. 16 does not comprise a magnetic oscillator that is coupled to a mechanical oscillator, but two magnetic oscillators between which a magnetic instead of a mechanical coupling is provided. The interaction between the two oscillators is therefore a bit different. Hence, also the generated induction signals will be of a different form. In particular, the generated induction signals will no longer result from the oscillation of only a single magnetic oscillator anymore, but can be understood as a superposition of generated induction signals resulting from the first oscillator with generated induction signals resulting from the second oscillator.

Figure 17:
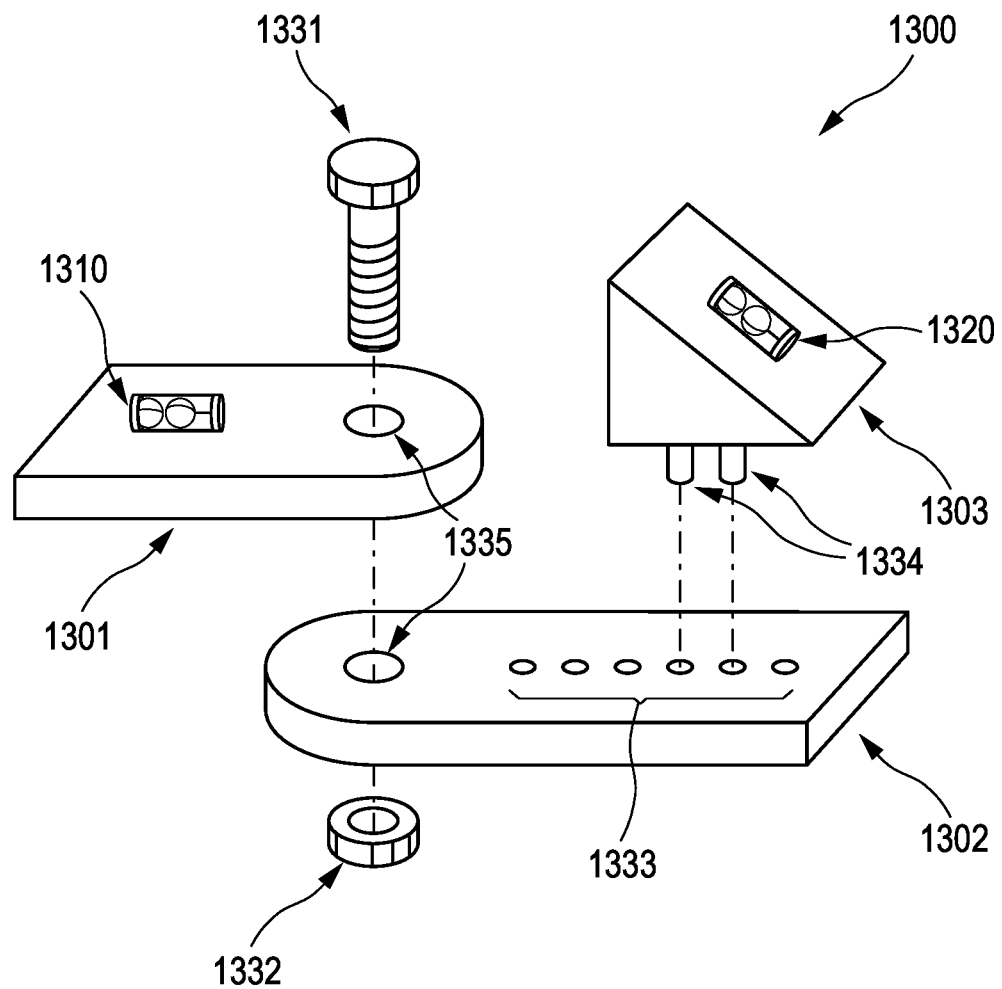
FIG. 17 shows schematically and exemplarily components of a passive medical combination identification device.

FIG. 17 shows schematically and exemplarily components of a combination identification device being, in this embodiment, a doublet identification device comprising a holding device 1300, which could also be named positioning unit 1300, for positioning a first identification device 1310 of the doublet identification device relative to a second identification device 1320 of the doublet identification device and for finally, i.e. after assembling, holding the first and second identification devices 1310, 1320 in their relative position. The positioning unit comprise a first holder 1301, a second holder 1303, and a third holder 1302. The first holder 1301 holds the first identification device 1310 in a first predetermined position, which might be regarded as a reference position, wherein the first identification device 1310 is held fixed by being glued to the first holder 1301. A depression or recess may be provided at a fixed location on the first holder 1301 in which the first identification device 1310 can be held. The first holder 1301 and the third holder 1302, both of which have a similar, plate-like form, each comprise a hole or hinge in an end region of the plate-like form, wherein these holes or hinges 1335 can be used for fixing the first holder 1301 to the third holder 1302 by insertion of a bolt 1331 from one side and securing with a nut 1332 from the opposing side. The third holder 1302 can be ultimately fixed to the first holder in a predetermined relative orientation, or only fixed so as to still allow for subsequent configuration of the relative orientation without being so loose as to risk a change in relative orientation during use of the doublet identification device. The third holder 1302 further comprises six holes 1333 for holding the second holder 1303, wherein each of the holes 1333 is provided at a different distance to the hole or hinge 1335 into which the bolt 1331 is inserted for fixing the first holder 1301 to the third holder 1302. The six holes 1333 are positioned equidistantly in a row. The second holder 1303, which is wedge-shaped, comprises two pegs 1334 protruding from its bottom side, wherein the two pegs 1334 fit into any two adjacent ones of the holes 1333, thus allowing for five different relative distances between the second holder 1303 and the first holder 1301. The pegs 1334 may be inserted into fixed two of the holes 1333, or only inserted so as to still allow for subsequent withdrawal and insertion into different two of the holes 1333 without being so loose as to risk a detachment of the second holder 1303 from the third holder 1302 during use of the doublet identification device. The second holder 1303 holds the second identification device fixed on an inclined surface, wherein second holders 1303 with different inclinations of the inclined surface relative to the third holder 1302, and hence also to the first holder 1301, might be provided. A depression or recess may be provided at a fixed location on the inclined surface of the second holder 1303 in which the second identification device 1320 can be held. Moreover, the second identification device 1320 may be fixed, such as glued, for instance, to the second holder 1303 at a configurable orientation. Its position relative to the first identification device 1310 therefore depends on a) the orientation of the third holder 1302 relative to the first holder 1301, the distance of the second holder 1303 relative to the first holder 1301 at which the pegs 1334 of the second holder 1303 are inserted into the holes 1333 of the third holder 1302, the inclination of the inclined surface of the second holder 1303 and the orientation in which the second identification device 1320 is fixed relative to the inclined surface of the second holder 1303, all of which are configurable to achieve a desired position of the second identification device 1320 relative to the first identification device 1310. Preferably, the desired relative position of the second identification device 1320 with respect to the first identification device 1310 can comprise any desired orientation.

A set of several of the identification devices 1201 can be provided, wherein at least two of these identification devices 1201 differ from each other with respect to a distance between the first and second oscillators and/or an orientation of one of the first and second oscillators relative to the other of the first and second oscillators and/or a coupling strength between the first and second oscillators.

Different distances and different orientations between the first and second oscillators can lead to different induction signals and can hence be used by the processor 33 to identify the respective identification device 1201. The processor 33 can be configured to directly use the different induction signals for determining the respective identity and/or the processor 33 can be configured to firstly determine the respective orientation and/or the respective distance based on the generated induction signals and to then extract the identification data of the respective identification device 1201 based on the determined orientation and/or the determined distance. In an example embodiment the identifying system and the identification devices are constructed such that the identification devices 1201 differ from each other with respect to 103 different relative orientations and 5 different relative distances of the respective oscillators, wherein this translates to 515 additional possibilities to distinguish the different identification devices from each other. This corresponds to about 9 bits which can be used for encoding the identity of the respective identification device.

The processor can be adapted to determine the respective relative orientation and/or the respective relative distance based on known relations between a) induction signals parameters and b) relative orientations and/or relative distances. These relations can be predetermined by calibration, wherein the induction signals can be measured, while a known relative orientation and/or a known relative distance is present. It is also possible that the processor 33 comprises or retrieves assignments between a) induction signals or characteristics of induction signals and b) identities of identification devices having certain structures. Also, these assignments can be predetermined by calibration, wherein the induction signals are measured and parameters of the measured induction signals are determined for an identification device having a known structure. These assignments can be used directly by the processor 33 together with currently measured induction signals for determining the respective identity. These assignments can also be used for training an artificial intelligence such as a neural network, wherein the trained artificial intelligence can be used for determining the identity of the respective identification device.

Generally, due to the different constructions of the different identification devices, each identification device leads to unique induction signals, which can also be regarded as being a fingerprint for the respective identification device, wherein these unique induction signals can be used together with predefined assignments, which might be provided in a table, as a function, as an artificial intelligence or by any other algorithms or devices linking the respective fingerprint induction signals to the respective identity, for determining the identity of the respective identification device.

The coupling strengths between the oscillators in a same identification device 1201 can be binary, i.e. either there is any coupling or no coupling, wherein the different identification devices 1201 can be constructed such that a coupling is present or not. The oscillators of a same identification device can couple by way of mechanical coupling and/or by magnetic interactions. In both cases, the strengths of the coupling can be modulated by the mechanical set-up and/or by the addition of magnetically soft material.

The identifying system can be configured to distinguish between an identification device having coupled oscillators and a further identification device, which does not have coupled oscillators, by firstly exciting both oscillators, which results in two peaks at two frequencies in the generated induction signals. Then, an excitation pulse, i.e. an excitation magnetic field, is used at one of these two frequencies, with relatively high magnetic excitation amplitudes where non-linear effects are already expected. In some embodiments, an excitation pulse is used at one of these two frequencies only. If the resulting induction signals show a signal pattern of a single oscillator only, i.e., for instance, if the resulting induction signals each have a peak only at the frequency of one of the oscillators, the two oscillators are not coupled and the coupling strength is zero. However, if the resulting induction signals show a signal pattern of two oscillators, i.e., for instance, two peaks at two frequencies, particularly a beat frequency, the oscillators are coupled and the coupling strength is non-zero. The consideration of the binary coupling strength can hence provide an additional bit, which can be used for encoding the identities of the identification devices.

The processor 33 can also be configured to determine the coupling strength between the first and second oscillators based on a model, which depends on a coupling constant describing the coupling strength and which can be fitted to the generated induction signals for determining the coupling constant. In an example embodiment the model can be described as follows.

The movement of the magnetic object 3 can be described by equation (4) of a dampened pendulum. The movement of the further magnetic object 1203, before considering the coupling, might be described by equation (5). The coupling strength F, which could also be named coupling force, can be described by equation (6), wherein adding the coupling strength F to equations (4) and (5) leads to equations (7) and (8), respectively. This can be numerically solved and matched to the generated induction signals, of which the amplitudes are proportional to temporal first derivatives of x and z, respectively, which results in the coupling constant k. The coupling constant k and hence the coupling strength can differ from identification device to identification device and used by the processor 33 for determining the identity of the respective identification device.

A set of several identification devices can be provided, which also differ from each other regarding the respective effective magnetic dipole moment of the oscillating magnetic object. For instance, at least two of the identification devices can differ from each other with respect to the shape of the oscillating magnetic object, in order to provide the different effective magnetic dipole moments. The different shapes can be, for instance, cylindrical and spherical.

Moreover, at least two of the identification devices might have different attachment locations of the filament 6 on the magnetic object 3. Since the magnetic object 3 is a magnetic dipole, the different attachment locations are different attachment locations with respect to the magnetic dipole. For instance, as shown in FIG. 1, for at least some identification devices the attachment location might be at the equator of the magnetic object 3, i.e. at the location where a north pole and a south pole of the magnetic object 3 are adjacent to each other, wherein for other identification devices the attachment location might not be at the equator of the magnetic object, wherein in the latter case a reduced effective magnetic dipole moment is provided.

The generated induction signals depend on the respective effective magnetic dipole moment, wherein the processor 33 can comprise assignments between a) induction signals or parameters of induction signals and b) effective magnetic dipole moments or identities of the identification device which are caused, inter alia, by the different effective magnetic dipole moments. These assignments can be predetermined in a calibration procedure. As explained above, also an artificial intelligence can be trained to determine the respective identity based on the respective induction signals which are caused, inter alia, by the different effective magnetic dipole moments. It is also possible that the processor 33 is configured to determine the respective effective magnetic dipole moment of the respective identification device based on the generated induction signals by using a model and to extract the identification data based on the determined effective magnetic dipole moment. The effective magnetic dipole moment can be used as an independent parameter for identifying the respective identification device, i.e. it can be used, for instance, independently of the resonant frequency. In an example embodiment the identifying system can be configured to allow to distinguish between at least 32 different effective magnetic dipole moments, thereby providing at least 5 bits for encoding the identity of the respective identification device.

In order to determine the effective magnetic dipole moment, the processor 33 can be configured to firstly determine the position of the identification device, particularly of the oscillator within the identification device, relative to the coils 20 in which the induction signals are generated, wherein the position refers to the location and the orientation, i.e. it refers to six degrees of freedom. For determining this position, the processor 33 can be configured to provide a model, which describes the generated induction signals depending on the position of an identification device. The processor 33 can be configured to adapt the model, especially the position used by the model, such that the induction signals described by the model fit as good as possible to the really generated induction signals. The model can also be regarded as being a function which describes the induction signals depending on the position of the identification device. The explicit form of the function is not necessarily known. For instance, the function might also be determined by calibration, wherein during a calibration procedure induction signals are measured, while an identification device is arranged at different known positions.

In particular, the model may refer to a simulation model, i.e. a model that uses basic physical relations to describe, depending on the position of the identification device, the generating of magnetic signals by the identification device upon excitation by an excitation field, the propagation of the generated magnetic signals in space and the induction of corresponding induction signals in the coils 20.

The position of the identification device can also be found by identifying the signal of the identification device, which in the simplest case comprises just one dipole component, in the several coils 20. Identifying the signal of the identification device may herein refer to an extracting of the signal originating from the identification device out of all signals induced in the several coils. This may, for instance, refer to a removal of noise and/or, in the simplest case, to picking out a component from the whole signal, wherein the picked-out component corresponds to a spectral region around a spectral peak. The width of the spectral region might be chosen, for instance, depending on the level of noise and/or a spectral distance to an adjacent peak in the signal which might be caused by another identification device. Although the identification device that has caused the peak in the chosen spectral region might not yet have been identified, it can already be fixedly associated with the picked-out signal component in this way, such that the picked-out signal component can then be used for determining the position of the identification device. Since, for any number of different identification devices, each peak in the whole signal can usually be associated uniquely to a different one of the identification devices, a number of positions corresponding to the number of identification devices can be determined, wherein these positions can then be used for identifying the identification devices positioned at the respective positions.

For a given identified signal, the position, i.e. the location and orientation, can be determined by varying, in the simulation model, a simulated signal source, i.e., in the simplest case a dipole, until the relative signal strength measured in the different coils is matched by a simulated relative signal strength. The matching may refer to a matching up to an error term that is to be minimized, wherein the error term might be, for instance, a root mean square error.

The coil sensitivities at each spatial position at each frequency are known beforehand. This can be obtained from simulating the amplifiers and coils, using well known simulation software, or by a calibration step or a mixture of both.

The processor 33 can be further configured to determine the strength of the magnetic dipole moment based on the determined position, known absolute sensitivities of the coils and characteristics of further possible components of the identifying system such as, for example, an amplifier and an analog-to-digital converter. In particular, the processor 33 can be configured to determine the strength of the magnetic dipole moment based on an inversion of all transfer functions of the signal chain, wherein the respective transfer function defines the relation between the input and the output of the respective component.

For the initial determination of the position, i.e. location and orientation, of the identification device, any standard electromagnetic positioning technique may be used. According to these techniques, typically the strengths of the induced signals generated in different coils by a medical tool whose position is to be determined are compared to each other to obtain relative signal strengths, wherein the relative signal strengths determined for the several coils, whose positions and sensitivities are known, allow to deduce a position of the medical tool, i.e., in this case, the identification device. Since only relative signal strengths are used, the actual strength of the signal originating from the medical tool to be positioned, i.e., in this case, the oscillating dipole strength associated with the identification device 3, does not need to be known for positioning. Known techniques for electromagnetic positioning, which might also be used for the initial positioning of the identification device, are exemplarily described in the articles "Electromagnetic navigation in medicine—basic issues, advantages and shortcomings, prospects of improvement" by Baszynski et al., Journal of Physics: Conference Series, volume 238 (2010) 012056, and "Fast numerical algorithm for a high-precision 6D electromagnetic positioning navigation system" by Xiang et al., Turkish Journal of Physics, volume 38, pages 165 to 173 (2014). The dependency of the induced signals generated in a coil at a given position from the oscillating dipole strength and its oscillation frequency, which may be determined from basic physical laws and/or by calibration, might be viewed as defining the transfer function for the respective coil which needs to be inverted for deducing the oscillating dipole strength. The effective dipole moment can be determined from the oscillating dipole moment and the excitation angle.

In an example embodiment as a model the already above described pendulum differential equation is used. Assuming the damping is small, for different (current) oscillation amplitudes, a different frequency is found. For example, if the oscillation frequency at very low amplitudes could be determined (where $x=\sin(x)$ in very good approximation), the true oscillation amplitude can be found for a large amplitude just by determining the ratio of the found frequency and the low amplitude frequency. When knowing the excitation angle and the effective magnetic dipole moment, for all positions, the induced voltage, i.e. the generated induction signals, can be determined. So on the other hand, if the position is known, the effective magnetic dipole moment can be determined.

In order to determine, based on the determined magnetic dipole moment, the effective magnetic dipole moment, the processor 33 can be further configured to determine the oscillation amplitude, i.e. to determine the amplitude with which the magnetic object rotationally oscillates.

For determining the oscillation amplitude, the processor 33 can use a further model which describes the generated induction signals based on the oscillation amplitude. In an example embodiment this model can be the above described well known differential equation of a dampened pendulum, wherein the gravitational force is replaced by magnetic force.

In an example embodiment the effective magnetic dipole moment and the oscillation amplitude, i.e. the maximum angle of the rotationally oscillating magnetic object relative to its equilibrium orientation, are disentangled. Once this is done, the effective dipole moment is known and the oscillation amplitude can be determined even at low excitation angles. Entanglement refers herein to a difficulty or impossibility of distinguishing between the effective dipole moment and the oscillation amplitude, which is particularly present at small oscillation amplitudes, where a growth in oscillating dipole strength and any generated induced signal can equally well be accounted for by a growth in effective dipole moment as a growth in oscillation amplitude. Disentanglement therefore preferably comprises determinations of the dipole strength also for relatively high oscillation amplitudes. "Relatively high" may refer herein to amplitudes in the non-linear regime of the model used for describing the oscillations.

In an example embodiment a model connects the effective magnetic dipole moment m, the oscillation angle x and the oscillating dipole strength d by $$d(t)=m \sin(x(t)) \quad (9),$$

wherein this translates into the following corresponding relation between the effective magnetic dipole moment m, the oscillation amplitude $\hat{x}$ and the dynamic dipole moment d:

$$\hat{d}=m \sin(\hat{x}) \quad (10).$$

Any of the previous two equations may be understood as a definition for the effective dipole moment m. In some embodiments, a vector equation and then a scalar product with a vector defined by the coil sensitivity are used to arrive at these equations.

The oscillating dipole strength d (t) is measured by using the induction signals in the coils in some embodiments. The x(t) can be deduced from the differential equation of the oscillator using $\hat{x}$ as input. The dynamic dipole moment may be defined as the amplitude of d (t) or a Fourier component. Therefore, equation (9) and/or equation (10) can be used to get the unknown quantity if two of the three quantities are known. For example, this may be done via a minimization process as measured data are noisy and models, i.e. the differential equations, may not represent reality fully.

In an example embodiment the processor 33 is configured to determine a zero excitation amplitude frequency based on the generated induction signals and to extract the identification data based on the determined zero excitation amplitude frequency. In particular, in an example embodiment the excitation and induction signal coil system 20, 31 is configured to a) generate the magnetic field providing the magnetic torque for rotating the magnetic object of the identification device out of its equilibrium orientation with different amplitudes and for thereby exciting a rotational oscillation of the magnetic object with different excitation amplitudes, the rotational oscillation inducing a response magnetic field, and b) transduce the response magnetic field into induction signals that depend on the different excitation amplitudes, wherein the processor 33 is configured to determine a dependency of a frequency of the induction signals on the excitation amplitude based on the generated induction signals, to adapt a dependency model, which is configured to model a dependency of the frequency of the induction signals on the excitation amplitude, to the determined dependency and to determine, as the zero excitation amplitude frequency, the frequency at which the configured dependency model indicates a zero excitation amplitude. In an example embodiment the identifying system 30 and the identification device are configured such the zero excitation amplitude frequency can be determined with an accuracy of 1 Hz over a bandwidth of about 2 kHz. This roughly corresponds to about 2 to the power of 11 such that in this way about 11 bits can be used for encoding the identity of the respective identification device.

The zero excitation amplitude frequency is the frequency of the induction signals at which the excitation amplitude has been extrapolated to a zero excitation amplitude. In particular, the induction signals and hence the frequency of the induction signals might be measured for different non-zero excitation amplitudes applied by the excitation and induction signal coil system, in order to measure this frequency depending on the excitation amplitude. This measurement leads to a decaying waveform to which a model can be fitted, in order to determine the zero excitation amplitude frequency.

The model describes the oscillator of the respective identification device and hence the generation of the induction signals. The model can be provided depending on the type of oscillator used in the respective identification device. In a preferred embodiment, the oscillator comprises a) a single rotating magnetic sphere attached to an inner wall of the casing via a filament, which could also be regarded as being a thread, and b) a single fixed magnetic sphere. Moreover, the thickness of the filament can be so small that a generally possible mechanical torque by the filament can be neglected. In this case the oscillation can be modelled in good approximation by the well-known differential equation of a dampened pendulum, wherein the gravitational force is replaced by magnetic force. In some embodiments, the differential equation, i.e. the model, depends on an initial amplitude and an initial velocity of the rotationally oscillating sphere, a coil sensitivity constant relating magnetic moment change to the recorded signal, i.e. to the generated induction signals, at least one damping constant, and the zero amplitude frequency or a parameter which depends on the zero amplitude frequency. The coil sensitivity constant is a three-dimensional vector of which only two parameters need to be optimized. These parameters are optimized until, i.e. are determined such that, the simulated result provided by the model matches the experimental result, i.e. the generated induction signals, as good as possible. One of these optimized parameters is the desired zero amplitude frequency or the parameter being dependent on the zero amplitude frequency, which hence could also be used for determining the zero amplitude frequency.

In an example embodiment the differential equation is defined as follows:

$$\ddot{x}+\gamma\dot{x}+\omega_0^2 \sin(x)=0 \quad (11),$$

wherein x indicates the angle of the magnetic object relative to its equilibrium angular orientation, $\gamma$ indicates the linear damping constant and $\omega_0$ the natural frequency, i.e. the resonant frequency, of the identification device without damping.

In equation (11), which is generally an equation for a harmonic oscillator, a sine has been added to the non-derivative term. In an example embodiment instead of describing everything in terms of abstract frequencies, abstract damping constant and abstract angle, the differential equation (11) can also be formulated in terms of physical properties. So, for example, $\omega_0$ may be expressed as $\omega_0^2 = D/J$ with J being the moment of inertia and D being the "Direktionsmoment" in German, which is defined as M=Dx with M being the torque on the rotating magnetic object. These can be the above mentioned "related parameters" which depend on the zero amplitude frequency.

In an example embodiment the processor 33 can be adapted to determine the sensitivity of the respective resonant frequency to an external magnetic field. In particular, the identifying system 30 can be configured to measure the resonant signal for different external magnetic fields, particularly for different external magnetic DC fields, wherein the processor 33 can be adapted to extract the identification data of the respective identification device based on the change of the resonant frequency depending on the changing external magnetic field.

Different identification devices can also differ from each other with respect to an amount of change of the resonant frequency depending on the excitation amplitude of the exciting magnetic field and/or the velocity of change of the resonant frequency depending on the excitation amplitude of the exciting magnetic field, wherein the velocity can be determined, for instance, as a time constant. Thus, the excitation and induction signal coil system 20, 31 can be configured to a) generate the magnetic field providing the magnetic torque for rotating the magnetic object of the identification device out of its equilibrium orientation with different amplitudes and for thereby exciting a rotational oscillation of the magnetic object with different excitation amplitudes, wherein the rotational oscillation induces a response magnetic field, and b) transduce the response magnetic field into induction signals that depend on the different excitation amplitudes, wherein the processor 33 can be configured to determine a) the amount of change of the resonant frequency depending on the excitation amplitude of the exciting magnetic field and/or b) the velocity of change of the resonant frequency depending on the excitation amplitude of the exciting magnetic field based on the generated induction signals. At higher oscillation amplitudes, which are caused by higher excitation amplitudes of the exciting magnetic field, the average attractive force between the magnetic spheres is reduced, which can lead to a changed resonant frequency. If the casing is soft enough, the resonant frequency alteration will be significant, and, if there is a viscous component in the casing or outside the casing, it will persist for a considerable time.

In an example embodiment the identification device comprises a further magnetic object for providing the restoring torque, wherein the attractive forces between the two magnetic objects depend on an angle α between them, i.e. between the two magnetic dipoles which in this embodiment are in parallel planes. The attractive force $F_a$ can be defined by following equation:

$$F_a = c \cos(\alpha) \quad (12)$$

with c being a constant. When the magnetic object is rotationally oscillating, the average force being the attractive force averaged over time will be smaller than an initial attractive force when the two magnetic dipole moments of the two magnetic objects point in opposing directions. If in an example embodiment the casing is not rigid, but soft, the casing will even change its length, wherein this length change can also contribute to the force change as at a respective angle α the average distance between the magnetic objects is increased, which in turn reduces the constant c. The soft casing will not react immediately as it has a mass that has to be moved and also as there may be a high viscosity medium such as, for example, blood in which the identification device may be placed in. Therefore, the change seen by this effect has a different time constant than the pendulum effect. For very high viscosity of a surrounding medium, it may be necessary to keep the device in a high amplitude oscillation for a long time in a region of several seconds to see the effect, for a lower viscosity of the surrounding medium only a few milliseconds are generally sufficient. Here the "spring" constant, i.e. the ultimate change in resonant frequency at a given oscillation amplitude, and the damping of the movement, i.e. the time constant to reach the ultimate resonant frequency, can be determined. The latter may be determined by, for instance, performing, after each excitation signal, a first determination of generated induced signals at a first time and a second determination of generated induced signals at a second, later time, wherein the first time might be chosen to lie immediately after the excitation and the second time might be chosen to be greater than the first time by a period corresponding to an expected damping time constant, wherein this procedure may be repeated for different expected damping time constants until a satisfactory fit of the model to the measured data can be achieved.

In an example embodiment it is possible to use these parameters, i.e. a) the amount of change of the resonant frequency depending on the excitation amplitude of the exciting magnetic field and/or b) the velocity of change of the resonant frequency depending on the excitation amplitude of the exciting magnetic field based on the generated induction signals, to distinguish between at least 64 different values, which provides at least six bits for encoding the identity of the identification devices.

The identifying system 30 may be configured to determine the amount of change and the velocity, i.e. the time constant, using various high angle excitations and low angle excitations. In particular, in an example embodiment at least two excitation amplitudes, which might be used at different times, might be applied. The identifying system 30 can be configured to start with a short burst of relatively high oscillation amplitudes and it can then be determined whether the resonant frequency changes, wherein, if the resonant frequency does not change, the relatively high excitation amplitude can be used for a longer time. This longer time corresponds, for example, to the longest expected time constant of the change of the resonant frequency, which might be known from previous measurements. Then, a relatively low excitation amplitude can be used and it can be detected how the resonant frequency changes over time. Thus, the time constant can be determined for a relatively large excitation amplitude and for a relatively low excitation amplitude, in order to determine how the time constant and hence the velocity of the change of the resonant frequency depends on the excitation amplitude of the exciting magnetic field.

In an example embodiment the processor 33 is configured to determine an oscillation damping property based on the generated induction signals and to extract the identification data based on the determined oscillation damping property. In particular, the processor 33 is configured to determine a linear oscillation damping property and/or a higher-order oscillation damping property as the oscillation damping property. The linear oscillation damping property refers to the dissipative force such as, for example, a friction force being linear in the velocity of the movement of the magnetic object. The linear oscillation damping property can be, for instance, a corresponding linear damping constant.

In some embodiments, the processor 33 is configured to determine the oscillating damping property based on a decay of the amplitude of the induction signals over time. In order to determine the linear oscillation damping property only, i.e. not also a higher order oscillating damping property, a decay of the amplitude of the induction signals over time can be considered, after an excitation of the rotational oscillation of the magnetic object with a relatively low amplitude of the generated magnetic field, which does not generate higher harmonics, has been stopped. In order to determine the higher-order oscillating damping property and optionally also the linear oscillating damping property based on a decay of the amplitude of the induction signals over time, a decay of the amplitude of the induction signals over time can be considered, after an excitation with a relative large amplitude of the generated magnetic field, which also generated higher harmonics, has been stopped. The linear and higher order oscillating damping properties can be determined by fitting a given model to the decaying amplitude of the generated induction signals. In an example embodiment the model is given by the well-known above mentioned differential equation of a dampened pendulum, wherein the gravitational force is replaced by magnetic force.

In an example embodiment the processor 33 is configured to adapt an exponential model to the decay of the amplitude of the induction signals over time, in order to determine the linear damping property. For instance, in an example embodiment the oscillator of the identification device is excited with an amplitude of the generating exciting magnetic field, which is so low that the oscillation can be described by a dampened harmonic oscillator. The rotational oscillation can in this case be described by equation (1). The amplitude of the generated induction signals are matched with the temporal derivate of x scaled with a scaling factor, wherein the scaling factor, $\omega_0$ and $\gamma$ are varied until the best possible match is reached. This allows to determine the linear damping constant $\gamma$. In an example embodiment the identifying system 30 and the identification device are configured such it can be distinguished between at least 32 different linear damping constants such that in this way about at least 5 bits can be used for encoding the identity of the respective identification device.

In an example embodiment the oscillator of the identification device is excited with an amplitude of the generating exciting magnetic field, which is so large that also a higher order, i.e. a non-linear damping, constant is present. This higher order damping constant might be caused by, for instance, a periodic elongation of the filament used for attaching the rotating magnetic object to the casing. In such an example embodiment the rotational oscillation might be described by the equation (2) in combination with equation (3). Also in this case the amplitude of the generated inducting signal is matched with the temporal derivate of x scaled with a scaling factor, wherein the scaling factor, $\omega_0$, $\gamma$ and $\delta$ are varied until the best possible match is reached. This allows to determine the linear damping constant $\gamma$ and also the higher-order damping constant $\delta$. In an example embodiment the identifying system and the identification device are configured such it can be distinguished between at least eight different higher-order damping constants such that in this way at least three further bits can be used for encoding the identity of the respective identification device.

In order to provide different damping properties, the casings can be filled with different gases or different liquids having different viscosities and/or the filaments can be made of different materials, in order to allow to distinguish different identification devices based on the different damping properties.

In an example embodiment at least two of the identification devices comprise, besides a first oscillator formed by the respective magnetic object and the respective restoring torque provider, a second oscillator formed by a) a further magnetic object being arranged within the casing such that it is rotatable out of an equilibrium orientation if an external magnetic torque is acting on the further magnetic object and b) a further restoring torque provider being configured to provide a restoring torque to force the further magnetic object back into the equilibrium orientation if an external magnetic torque has rotated the further magnetic object out of the equilibrium orientation, in order to allow for a rotational oscillation of the further magnetic object excited by the external magnetic torque, wherein the at least two identification devices have a same respective one of the first and second oscillators and wherein the respective other one of the first and second oscillators differs from identification device to identification device with respect to its spatial relation to the respective one of the first and second oscillators and/or with respect to its construction. The two oscillators can be, for instance, the two oscillator shown in FIG. 16. The construction of an oscillator refers to, for instance, the number and kind of components, the used materials, the relative positions of the different components, et cetera.

Since a respective one of the first and second oscillators is the same for different identification devices, in this embodiment this respective one of the first and second oscillators cannot be used for distinguishing the different identification devices and hence for identifying the different markers, but it can be used for measuring a property such as, for example, a temperature, a pressure, et cetera. It could therefore be regarded as being a measuring oscillator or measurement type oscillator. The respective other one of the first and second oscillators is different or has a different spatial relation to the measuring oscillator for different identification devices and can therefore be used for distinguishing the different identification devices and hence for identifying the different identification devices. This other one could be regarded as being an identifying oscillator or identification type oscillator. Thus, in an example embodiment an identification device comprises a measurement type oscillator that does not provide any additional encoding as it is, for instance, mass produced and always the same. It may, for example, measure the temperature by a temperature dependent frequency shift. For identifying such an identification device, it also comprises an identifying oscillator that encodes a number by, for instance, its resonant frequency.

In some embodiments, the frequency ranges of both oscillators do not overlap such that it is know which frequency range of the induction signals are for identification and which frequency range of the induction signals are for measurement. The processor 33 can be configured to, since the generated induction signals show two peaks, determine the locations of the sources of the two peaks and the distance between these two locations, wherein, if this distance is smaller as a predefined threshold, it concludes that the two frequencies belong to a same identification device, wherein one frequency is used for determining the identity of the identification device and the other frequency is used for determining the temperature of the identification device. If there are more than two peaks, corresponding locations can be determined and the locations can be clustered such that peaks caused by nearby locations are assigned to each other, wherein the frequency at one of the peaks of a cluster is used for determining the respective identity and the frequency at another one of the peaks of a same cluster is used for determining the respective temperature. Instead of or in addition to the temperature, a measuring oscillator can also be used for measuring another property such as, for example, pressure.

The identification devices can be further distinguished from each other by equipping them with additional permanent magnetic material, in order to provide additional magnetic DC fields. The permanent magnetic material can be arranged adjacent to soft magnetic material, if the respective identification device also comprises soft magnetic material, i.e. magnetically soft material. The permanent magnetic material can be moveable within the respective identification device or changed in its magnetization by using an external magnetic field, wherein this allows to program the respective identification device. The permanent magnetic material is a magnetically hard material such as, for example, a material of the barium ferrite type. The added permanent magnetic material can change the induction signals such that it can be used for further distinguishing the different identification devices. In particular, the amplitude of the resonant frequency and possibly present harmonics can differ from identification device to identification device and used for identifying their respective identification device. In an example embodiment the amplitudes of the harmonics are normalized with respect to the amplitude of the resonant frequency and the resulting normalized amplitudes for the different harmonics can be regarded as being a pattern, wherein the processor 33 can be configured to determine the different identification devices based on the different patterns.

The processor 33 can be configured to determine a further property of the identification device based on the generated induction signals, wherein this further property can be, for instance, location, orientation, temperature and/or pressure. Thus, in an example embodiment the identification device does not only provide identity information, but also information about a property such as, for example, the temperature or pressure, wherein the processor 33 is configured to determine the identity information and the property information. For instance, if a property change such as, for example, a temperature change leads to a change of a frequency parameter of the induction signals, wherein this change of the frequency parameter should be used for determining the property, and if in addition parameters of the respective identification device such as, for example, the effective magnetic dipole moment should be used for distinguishing between different identification devices and for hence providing their identity, firstly the position of the identification device might be determined by exciting the rotational oscillation and by analyzing the generated induction signals.

The processor can be configured to determine the position, i.e. the location and the orientation, of the respective identification device based on the relative strength of the induction signals generated in the respective receive coil, wherein it can be ensured that the generated induction signals originate from a respective single identification device by, for instance, only considering a single frequency.

The processor can be further configured to use the location and the strength of the induction signals particularly including the strengths, i.e. the amplitudes, of the harmonics for determining the parameters of the identification device to be used for its identification such as, for example, determining the oscillation amplitude and hence the effective magnetic dipole moment.

After the identification device has been identified, assignments such as, for example, a table or curve between the frequency parameter and the property to be measured such as, for example, the temperature can be provided. These assignments can have been predetermined by calibration. These assignments can be the same for all identification devices or they can be specific for the respective identification device. For instance, for each identification device a respective curve can be provided, which relates the temperature to a zero excitation amplitude frequency, wherein the zero excitation amplitude frequency can be determined and the curve provided for the identified identification device can be used for determining the temperature.

Figure 18:
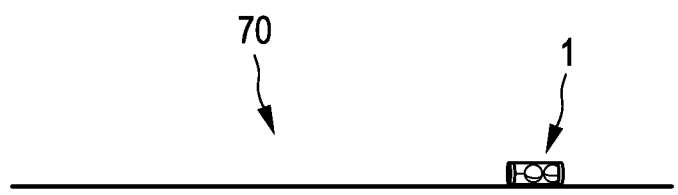
FIG. 18 shows schematically and exemplary an embodiment of a medical device comprising a passive medical identification device.

FIG. 18 shows schematically and exemplarily an attachment of an identification device 1 to a medical instrument 70 such as, for example, a guidewire or a catheter, in order to provide the medical instrument 70 with an identity. The processor 33 can be adapted to determine the identity of the medical instrument 70 by determining the identity of the identification device 1.

Figure 19:
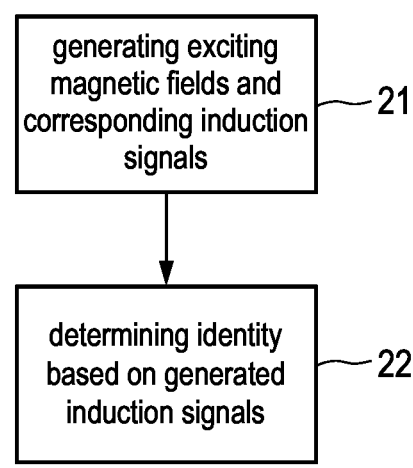
FIG. 19 shows a flowchart exemplarily illustrating an embodiment of an identifying method for identifying a medical tool equipped with a passive medical identification device.

In the following paragraphs, an example embodiment of an identification method for identifying a medical tool such as, for example, the medical instrument 70 equipped with an identification device will exemplarily be described with reference to a flowchart shown in FIG. 19.

In step 21 a magnetic field is generated, which provides a magnetic torque for rotating the magnetic object 3 of the identification device 1 within the subject out of its equilibrium orientation and for thereby exciting a rotational oscillation of the magnetic object 3, the rotational oscillation inducing a response magnetic field. Moreover, in step 21 the response magnetic field is transduced into induction signals, which are caused by the rotational oscillation of the magnetic object 3 and which depend on the identity of the identification device 1. In step 22 the identity of the identification device 1 and thereby also of the medical instrument 70 is determined, i.e. the identification data are extracted, based on the induction signals.

Although in an above described embodiment the identification device has been used to identify a surgical instrument, in other embodiments the identification device can also be attached to other medical tools for identifying these other medical tools.

Although above certain embodiments of identification devices have been described, also other identification devices can be used, which have a casing, a magnetic object and a restoring torque provider being adapted to provide a restoring torque to force the magnetic object back into the equilibrium orientation if an external magnetic torque has rotated the magnetic object out of the equilibrium orientation, in order to allow for a rotational oscillation of the magnetic object excited by the external magnetic torque.

Generally, in order to provide an identification device having a certain resonant frequency, there are several ways to construct it. In particular, differently constructed identification devices can have a same resonant frequency. For instance, in an identification device with two magnetic objects such as, for example, to magnetic spheres, the same frequencies can be the result of two large magnetic objects close together or two small magnetic objects with larger a distance relative to each other. The reason is that the frequency is inversely proportional to the size and proportional to the square root of the magnetic field. The magnetic field of a magnetic object at the location of the other magnetic object is inversely proportional to the third power of the center to center distance. With this it is possible to reduce the frequency of the identification device by increasing the distance between the identification devices. So, with a given size, the frequency has a maximum value if the magnetic objects touch and it is reduced at larger distances. Thus, for instance, the frequency of a large sphere system can be mimicked by a small sphere system just by having a larger distance. Also, the damping constants might be affected such that also other parameters such as, for example, the filament properties might need to be changed, in order to mimic the same frequency with differently constructed identification devices, if desired.

Although in above described embodiments the imaging system is an x-ray C-arm system, other imaging systems can be used such as a C-arm system with an optical camera system, an ultrasound imaging system, for instance, a transesophageal echocardiography (TEE) ultrasound imaging system or an intravascular ultrasound imaging system, et cetera. The identification devices and the identifying system can also be used without any imaging system.

The identification device can also comprise units or algorithms for reducing a possible temperature dependence of the resonant frequency. For instance, the identification device can comprise magnetic material of which the magnetization changes with temperature, in order to thereby change the magnetic field at the location of the magnetic object and hence the resonant frequency with temperature. This magnetic material can be arranged such the change of the resonant frequency with temperature caused by the magnetic material compensates a generally possible change of the resonant frequency due to temperature changes caused by one or several other elements of the identification device. The magnetic material may be located on or adjacent to the further magnetic object. Alternatively or in addition, the magnetic material may be applied to the magnetic object, in order to change its magnetic dipole moment with temperature such that this change of the magnetic dipole moment compensates a generally possible change of the resonant frequency due to temperature changes caused by one or several other elements of the identification device.

The generation of the magnetic field which provides a magnetic torque for rotating the magnetic object of the measurement device out of its equilibrium orientation and for thereby exciting a rotational oscillation of the magnetic object, wherein the rotational oscillation induces a response magnetic field, can be implemented in many different ways. For instance, the excitation can use individual single pulses of a magnetic field, wherein between the pulses the frequency and phase of the induced signal can be measured. From this, the timing of the next short pulse can be computed such that it increases the oscillation amplitude of the magnetic object. As an alternative, the single pulse can be replaced with a pulse train of few pulses with positive and negative amplitudes. This short pulse train still covers a relative broad potential excitation spectrum, the center of which is designed to lay approximately at the expected resonant frequency. The timing of the pulse train is again adjusted so that it increases the oscillation amplitude of the magnetic object. The frequency of the resulting optimized induction signals can be regarded as being the resonant frequency.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures such as, for example, the determination of the identity of the identification device based on the generated induction signals, the control of the excitation of the identification devices by controlling the current within the coils, et cetera, performed by one or several units or devices can be performed by any other number of units or devices. These procedures and/or the control of the identifying system in accordance with the identifying method can be implemented as program code unit or algorithm of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a passive medical identification device to be used for identifying a medical tool such as, for example, a surgical instrument, if the medical tool is equipped with the identification device. The identification device comprises a casing, a magnetic object arranged within the casing such that it is rotatable out of an equilibrium orientation by an external magnetic torque, and a restoring torque provider such as, for example, a further magnetic object providing a restoring torque forcing the magnetic object back into the equilibrium orientation. The magnetic object rotationally oscillates upon excitation by an external magnetic torque, thereby generating a response magnetic signal which is transduced into an induction signal that can provide a fingerprint specific for the respective identification device. Accordingly, the identity of the identification device and hence of the medical tool equipped with the identification device can be determined based on the induction signal.

The invention claimed is:

1. An identifying system for identifying a passive medical identification device,
wherein the passive medical identification device comprises,
a casing:
a magnetic object, wherein the magnetic object is arranged within the casing such that the magnetic object rotatable out of an equilibrium orientation when an external magnetic torque is acting on the magnetic object, and
a restoring torque provider, wherein the restoring torque provider is configured to provide a restoring torque to force the magnetic object back into the equilibrium orientation when the external magnetic torque has rotated the magnetic object out of the equilibrium orientation, in order to allow for a rotational oscillation of the magnetic object excited by the external magnetic torque, wherein the rotational oscillation generates a response magnetic signal, wherein the casing, magnetic object and the restoring torque provider are arranged such that at least one property of the response magnetic signal is suitable to be used by the identifying system to extract identification data from an induction signal,
wherein the identifying system comprises:
an excitation and induction signal coil system configured to:
a) generate a magnetic field providing a magnetic torque for rotating the magnetic object of the passive medical identification device out of its equilibrium orientation and for exciting a rotational oscillation of the magnetic object, wherein the rotational oscillation induces a response magnetic field, and
b) transduce the response magnetic field into an induction signal, and a processor, wherein the processor is configured to receive the induction signal and to extract identification data.

2. The identifying system of claim 1, wherein the identifying system is configured to identify at least two passive medical identification devices, and wherein at least one of the passive medical identification devices has a first coupled oscillator, and wherein the identifying system is configured to distinguish between the at least two passive medical identification devices.

3. The identifying system of claim 2, wherein at least one of the passive medical identification devices has a second coupled oscillator, and wherein the second coupled oscillator is configured for the identifying system to measure at least one of a temperature and a pressure.

4. The identifying system of claim 2, wherein the at least two passive medical identification devices each have one or more coupled oscillators, wherein the one or more coupled oscillators of the first passive medical identification device are arranged at a different angle and/or position than the one or more coupled oscillators of the second passive medical identification device.

5. The identifying system of claim 2, wherein the identifying system further comprises a holding device for positioning a first one of the passive medical identification devices relative to a second one of the passive medical identification devices.

6. The identifying system of claim 1, wherein the processor is configured to:
i) determine, based on the induction signal, at least one property of the passive medical identification device, wherein the at least one property includes at least one selected from a list consisting of resonant frequency, effective magnetic dipole moment, maximum oscillation angle, zero excitation amplitude frequency, oscillation damping, resonant frequency of a further oscillating element of the passive medical identification device, amount of change of the resonant frequency depending on an excitation amplitude of an exciting magnetic field, velocity of change of the resonant frequency depending on the excitation amplitude of the exciting magnetic field, sensitivity of the respective resonant frequency to an external magnetic field, generation of harmonics of the induction signals, and ii) extract the identification data of the passive medical identification device based on the determined at least one property of the passive medical identification device.

7. The identifying system of claim 1, wherein the processor is configured to determine a second harmonic of the induction signal and to determine a maximum oscillation angle based on the determined second harmonic, wherein the second harmonic can be determined by applying a Fourier transform of the induction signal and the maximum oscillation angle is the maximum oscillation angle of the passive medical identification device.

8. The identifying system of claim 1, wherein the excitation and induction signal coil system is configured to:
a) generate the magnetic field providing the magnetic torque for rotating the magnetic object of the passive medical identification device out of its equilibrium orientation with different amplitudes and exciting a rotational oscillation of the magnetic object with different excitation amplitudes, wherein the rotational oscillation induces a response magnetic field, and
b) transduce the response magnetic field into the induction signal, wherein the induction signal depends on the different excitation amplitudes, wherein the processor is configured to determine a dependency of a frequency of the induction signal on the excitation amplitude based on the induction signal, to adapt a dependency model, which is configured to model a dependency of the frequency of the induction signal on the excitation amplitude, to the determined dependency and to determine, as a zero excitation amplitude frequency, the frequency at which the adapted dependency model indicates a zero excitation amplitude.

9. The identifying system of claim 1 wherein the passive medical identification device comprises:
a first oscillator formed by the respective magnetic object and the respective restoring torque provider, and
a second oscillator formed by:
a) a further magnetic object, wherein the further magnetic object is arranged within the casing such that the further magnetic object is rotatable out of an equilibrium orientation when the external magnetic torque is acting on the further magnetic object, and
b) a further restoring torque provider, wherein the a further restoring torque provider is configured to provide a restoring torque to force the further magnetic object back into the equilibrium orientation when the external magnetic torque has rotated the further magnetic object out of the equilibrium orientation, in order to allow for a rotational oscillation of the further magnetic object excited by the external magnetic torque, wherein the processor is configured to determine at least one property from a group consisting of a distance between the first and second oscillators, an orientation of one of the first and second oscillators relative to the other of the first and second oscillators, and a coupling strength between the first and second oscillators, and to extract the identification data based on the determined at least one property.

10. The identifying system of claim 1, wherein the excitation and induction signal coil system is configured to
a) generate the magnetic field providing the magnetic torque for rotating the magnetic object of the passive medical identification device out of its equilibrium orientation with different amplitudes and exciting the rotational oscillation of the magnetic object with different excitation amplitudes, wherein the rotational oscillation induces the response magnetic field, and
b) transduce the response magnetic field into the induction signal, wherein the induction signal depends on the different excitation amplitudes, wherein the processor is configured to determine i) an amount of change of the resonant frequency depending on the excitation amplitude of the exciting magnetic field and/or ii) a velocity of change of the resonant frequency depending on the excitation amplitude of the exciting magnetic field, based on the induction signal.

11. The identifying system of claim 1, further comprising a controller, wherein the controller is adapted to control coils of the excitation and induction signal coil system.

12. The identifying system of claim 1, wherein the identifying system further comprises a location provider configured to determine a location of the passive medical identification device.

13. The identifying system of claim 1, wherein the identifying system is configured to identify at least two passive medical identification devices, wherein the at least two passive medical identification devices are differing in identification of features comprising: resonant frequency, effective magnetic dipole moment, maximum oscillation angle, zero excitation amplitude frequency, oscillation damping, resonant frequency of a further oscillating element of the passive medical identification device, amount of change of the resonant frequency depending on an excitation amplitude of an exciting magnetic field, velocity of change of the resonant frequency depending on the excitation amplitude of the exciting magnetic field, sensitivity of the respective resonant frequency to an external magnetic field, generation of harmonics of the induction signals.

14. An identifying method, wherein the identifying method comprises:
generating a magnetic field providing a magnetic torque for rotating a magnetic object of a passive medical identification device out of its equilibrium orientation and exciting a rotational oscillation of the magnetic object, the rotational oscillation inducing a response magnetic field, by an excitation and induction signal coil system,
transducing the response magnetic field into an induction signal by the excitation and induction signal coil system, and
receiving the induction signal, and extracting identification data from the induction signal, by a processor.

15. The identifying method of claim 14, comprising identifying at least two passive medical identification devices, wherein at least one of the passive medical identification devices has a first coupled oscillator, and wherein method is further configured to distinguish between the at least two passive medical identification devices.

16. The identifying method of claim 15, wherein the passive medical identification device comprises a first oscillator formed by the respective magnetic object and the respective restoring torque provider, and a second oscillator, wherein the method further comprises: determining at least one property from a group consisting of a distance between the first and second oscillators, an orientation of one of the first and second oscillators relative to the other of the first and second oscillators, and a coupling strength between the first and second oscillators, and to extract the identification data based on the determined at least one property.

17. The identifying method of claim 14, wherein the processor is configured to
i) determine, based on the induction signal, at least one property of the passive medical identification device selected from a list consisting of resonant frequency, effective magnetic dipole moment, maximum oscillation angle, zero excitation amplitude frequency, oscillation damping, resonant frequency of a further oscillating element of the passive medical identification device, amount of change of the resonant frequency depending on an excitation amplitude of an exciting magnetic field, velocity of change of the resonant frequency depending on the excitation amplitude of the exciting magnetic field, sensitivity of the respective resonant frequency to an external magnetic field, and generation of harmonics of the induction signal, and
ii) extract the identification data of the passive medical identification device based on the determined at least one property of the passive medical identification device.

18. A tangible non-transitory computer-readable medium comprising instructions which, when executed by a computer, cause the computer to control an identifying system to carry out the method of claim 14.

19. A tangible non-transitory computer-readable medium having stored thereon a computer program for identifying a medical tool equipped with a passive medical identification device, wherein the computer program comprises program code which causes an identifying system to carry out the identifying method of claim 12, when the computer program is run on a computer controlling the identifying system.

20. A system, comprising:
the identifying system of claim 1; and
the passive medical identifying device.

21. A passive medical identification device, comprising:
a casing,
a magnetic object, wherein the magnetic object is arranged within the casing such that the magnetic object is rotatable out of an equilibrium orientation when an external magnetic torque is acting on the magnetic object, and
a restoring torque provider, wherein the restoring torque provider is configured to provide a restoring torque to force the magnetic object back into the equilibrium orientation when the external magnetic torque has rotated the magnetic object out of the equilibrium orientation, in order to allow for a rotational oscillation of the magnetic object excited by the external magnetic torque,
wherein the rotational oscillation generates a response magnetic signal, and
wherein the casing, magnetic object and the restoring torque provider are arranged such that at least one property of the response magnetic signal is suitable to be used by an identifying system to extract identification data from an induction signal.

\* \* \* \* \*